US010595534B2

(12) United States Patent
Cobb

(10) Patent No.: US 10,595,534 B2
(45) Date of Patent: *Mar. 24, 2020

(54) POST-EMERGENCE HERBICIDE

(71) Applicant: Belvedere Foliar LLC, Belvedere, CA (US)

(72) Inventor: David A. Cobb, Belvedere, CA (US)

(73) Assignee: Belvedere Foliar LLC, Belvedere, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/193,312

(22) Filed: Nov. 16, 2018

(65) Prior Publication Data

US 2019/0082698 A1 Mar. 21, 2019

Related U.S. Application Data

(63) Continuation of application No. 15/916,107, filed on Mar. 8, 2018, now Pat. No. 10,182,572.

(60) Provisional application No. 62/469,087, filed on Mar. 9, 2017, provisional application No. 62/609,137, filed on Dec. 21, 2017.

(51) Int. Cl.
| | | |
|---|---|---|
| *A01N 59/00* | (2006.01) | |
| *A01N 59/02* | (2006.01) | |
| *A01N 59/16* | (2006.01) | |
| *A01N 59/14* | (2006.01) | |
| *A01N 37/02* | (2006.01) | |
| *A01N 59/06* | (2006.01) | |
| *A01N 59/26* | (2006.01) | |

(52) U.S. Cl.
CPC ............. *A01N 59/00* (2013.01); *A01N 37/02* (2013.01); *A01N 59/02* (2013.01); *A01N 59/06* (2013.01); *A01N 59/14* (2013.01); *A01N 59/16* (2013.01); *A01N 59/26* (2013.01)

(58) Field of Classification Search
CPC ........ A01N 59/00; A01N 59/02; A01N 59/16; A01N 59/14; A01N 37/02
See application file for complete search history.

(56) References Cited

U.S. PATENT DOCUMENTS

| | | |
|---|---|---|
| 3,023,096 A | 2/1962 | Guth |
| 3,679,392 A | 7/1972 | Strauss et al. |
| 3,681,478 A | 8/1972 | Gutman |
| 3,771,994 A | 11/1973 | McConnell et al. |
| 3,799,758 A | 3/1974 | Franz |
| 3,942,971 A | 3/1976 | Toepfl |
| 3,983,116 A | 9/1976 | Lin |
| 4,137,065 A | 1/1979 | Satomi et al. |
| 4,278,461 A | 7/1981 | Salbeck et al. |
| 4,453,965 A | 6/1984 | Patel |
| 4,456,464 A | 6/1984 | Lee et al. |
| 4,881,967 A | 11/1989 | Semple |
| 4,921,527 A | 5/1990 | Tseng |
| 4,994,101 A | 2/1991 | Young |
| 5,356,862 A | 10/1994 | Zimmerman |
| 5,569,639 A | 10/1996 | Beestman |
| 5,759,226 A | 6/1998 | Herold et al. |
| 5,798,317 A | 8/1998 | Pappas-Fader et al. |
| 5,917,117 A | 6/1999 | Ensley et al. |
| 6,329,323 B1 | 12/2001 | Bettarini et al. |
| 6,436,165 B1 * | 8/2002 | Konzak .................... C05B 15/00 71/33 |
| 6,972,273 B2 | 12/2005 | Sedun et al. |
| 7,811,352 B2 * | 10/2010 | Binder ...................... C05C 3/00 71/6 |
| 8,530,385 B2 | 9/2013 | Yeritsyan et al. |
| 8,946,122 B2 | 2/2015 | Fowler et al. |
| 9,045,720 B2 | 6/2015 | Gioia et al. |
| 10,182,572 B2 * | 1/2019 | Cobb ...................... A01N 59/06 |
| 2003/0096708 A1 | 5/2003 | Agbaje et al. |
| 2005/0178178 A1 | 8/2005 | Lovatt |
| 2007/0293397 A1 * | 12/2007 | Selvig ..................... A01N 63/00 504/117 |
| 2013/0260996 A1 | 10/2013 | Wilson et al. |
| 2014/0342911 A1 * | 11/2014 | Jennings ................ A01N 59/14 504/187 |
| 2014/0357486 A1 | 12/2014 | Akers |
| 2015/0173364 A1 | 6/2015 | Caceres et al. |
| 2015/0239788 A1 * | 8/2015 | Yamashita .............. C05F 11/08 504/101 |
| 2015/0351407 A1 | 12/2015 | Jennings |

FOREIGN PATENT DOCUMENTS

| | | |
|---|---|---|
| WO | WO 99/57959 | 11/1999 |
| WO | WO 2015/119514 | 8/2015 |
| WO | WO 2016/141485 | 9/2016 |
| WO | WO 2017/044644 | 3/2017 |

OTHER PUBLICATIONS

Shafer et al, The foliar absorption of potassium from organic and inorganic potassium carriers, Journal of Plant Nutrition, 9(2), 143-157. (Year: 1986).*
Bukovac et al, Absorption and mobility of foliar applied nutrients, Plant physiology, 428-434. (Year: 1957).*
Mengel, Alternative or complementary role of foliar supply in mineral nutrition, Institute of plant nutrition, 33-38. (Year: 2002).*
Abouziena et al., "Efficacy Comparison of Some New Natural-Product Herbicides for Weed Control at Two Growth Stages", Weed Technology, vol. 23, pp. 431-437, 2009.

(Continued)

*Primary Examiner* — Mina Haghighatian
(74) *Attorney, Agent, or Firm* — Knobbe, Martens, Olson & Bear LLP

(57) ABSTRACT

Some embodiments relate to herbicide compositions and methods of inducing phytoxicity in a plant, by administering an aqueous composition to foliar portions of the plant. This aqueous composition includes at least one nutrient, and at least one adjuvant, and has a pH of about 4 to about 7. In some embodiments, the aqueous composition comprises an organic or mineral acid. In some embodiments, the phytotoxicity is topical. In some embodiments, the phytotoxicity is systemic. Without being limited by theory, the nutrient is absorbed by the plant in excess, thereby killing the plant.

15 Claims, 20 Drawing Sheets

(56) References Cited

OTHER PUBLICATIONS

Berndt, G., "Efficiency of foliar sprays as influenced by the inclusion of surfactants", Research and Development in Agriculture, vol. 4, No. 3, pp. 129-139, 1987.
Borowski et al., "The Effect of Foliar Feeding of Potassium Salts and Urea in Spinach on Gas Exchange, Leaf Yield and Quality", Acta Agrobotanica, vol. 62, No. 1, pp. 155-162, 2009.
Christensen, L., "Foliar Fertilization in vine Mineral Nutrient Management Programs", Soil Environment and Vine Mineral Nutrition, pp. 83-90, 2005.
Czarnota, M., "Using Surfactants, Wetting Agents, and Adjuvants", Greenhouse. Univ. Georgia Coop. Extn., Athens, Georgia. Pub. B-1309. 10 pages, 2013.
Dayan et al., "Natural products in crop protection", Bioorganic & Medicinal Chemistry, vol. 17, pp. 4022-4034, 2009.
Dill et al., "Glyphosate: Discovery, Development, Applications, and Properties", Glyphosate Resistance in Crops and Weeds: History, Development, and Management, Edited by Vijay K. Nandula, John Wiley & Sons, Inc., Copyright 2010.
El-Nour, E., "Can Supplemented Potassium Foliar Feeding Reduce the Recommended Soil Potassium?", Pakistan Journal of Biological Sciences, vol. 5, No. 3, pp. 259-262, 2002.
Elser et al., "Global analysis of nitrogen and phosphorus limitation of primary producers in freshwater, marine and terrestrial ecosystems", Ecology Letters, vol. 10, 8 pages, 2007.
Eutrophication. Wikipedia. accessible on the world wide web at en.wikipedia.org/wiki/Eutrophication, 2016.
Fertilizer, Wikipedia, Retrieved from the world wide web at enwikipedia.org/w/index.php?title=Fertilizer&oldid=681352858, Website page was last modified on Sep. 16, 2015, 16 pages. However, as this document refers to a web page, it may have been available in some form at an earlier point in time.
Forouzesh et al., "Classification of herbicides according to chemical family for week resistance management strategies—an update", Weed Research, vol. 55, No. 4, pp. 334-358, Aug. 2015.
Hager et al.,"Principles of Postemergence Herbicides", Univ. of Ill, Coop. Exten. Serv. Urbana, III, 4 pages, 1997.
Hay, J.V., "Chemistry of sulfonylurea herbicides," Pesticide Science (1990) 29(3):247261. http://onlinelibrary.wiley.com/doi/10.1002/ps.2780290303/abstract (Abstract).
Howard et al,, "Foliar Feeding of Cotton: Evaluating Potassium Sources, Potassium Solution Buffering, and Boron", Agronomy Journal, vol. 90, Nov.-Dec. 1998, 4 pages.
International Search Report and Written Opinion dated May 2, 2018 in Application No. PCT/US2018/020868.
Johnson, B., "Pay attention to timing when applying fertilizer", Ag Alert, Feb. 3, 2016, 2 pages.
Kurtural et al., "Fertilization of Grapevines", Agricultural & Natural Resources, 6 pages, 2008.
Laboski, C., "Understanding Salt Index of Fertilizers", Proc. of the 2008 Wisconsin Fertilizer, Aglime & Pest Management Conference, vol. 47, pp. 37-41.
Marschner, H., "Mineral Nutrition of Higher Plants", Academic Press Limited, Copyright 1986, Table of Contents in 6 pages.
McCauley et al., "Plant Nutrient Functions and Deficiency and Toxicity Symptoms", Nutrient Management Module No. 9, Montana State University, reprinted Jun. 2011, 16 pages.
Mengel, K., "Alternative or Complementary Role of Foliar Supply in Mineral Nutrition", Proc. Int'l Sup. Foliar Nutrition, 2002, vol. 594, pp. 32-47.
Mengel, K., "Dynamics and Availability of Major Nutrients in Soils", Advances in Soil Science, vol. 2, Copyright 1985, pp. 65-131.
Munson et al., "Movement of Applied Potassium in Soils", American Potash Institute, Inc., vol. 11, No. 3, May-Jun. 1963, pp. 193-201.
NACHURS® Bio-K®, website page, accessible on the worldwide web at www.nachurs.com/bio-k/, Copyright 2018. However, as this reference refers to a website, it may have been available in some form at an earlier point in time.
Oosterhuis, D., "Foliar Fertilization: Mechanisms and Magnitude of Nutrient Uptake", Paper for the Fluid Fertilizer Foundation meeting in Scottsdale, Arizona, Feb. 15-17, 2009, 4 pages.
Smith-Fiola, D., Iron-Based Herbicides: Alternative Materials for Weed Control in Landscapes and Lawns, University of Maryland Extension—Solutions in your community, 2014, 4 pages.
U. S. Food and Drug Administration. 2007. Approximate pH of foods and food products. Accessible on the world wide web at www.foodscience.caes.uga.edu/extension/documents/fdaapproximatephoffoodslacf-phs.pdf. However, as this document refers to a web site, it may have been available in some form at an earlier point in time.
Wójcik, P., "Uptake of Mineral Nutrients From Foliar Fertilization (Review)", Journal of Fruit and Ornamental Plant Research, vol. 12, 2004, 23 pages.
Zollinger, R., Spray Adjuvants: The Rest of the Story (reposted from CWSS), UC Week Science, published on Sep. 12, 2014, 4 pages total.
Office Action dated May 16, 2018 in U.S. Appl. No. 15/916,107.
Office Action dated Aug. 13, 2018 in U.S. Appl. No. 15/916,107.
Syverud et al., "Foliar fertilization of soybeans (*Glycine max* L.)", Communications in Soil Science and Plant Analysis,11:6, (1980), 637-651, DOI: 10.1080/00103628009367069.
Parker et al., "Foliage Injury, Nutrient Intake, and Yield of Soybeans as Influenced by Foliar Fertilization", AGron. J., vol. 72 No. 1, Jan. 1980, pp. 110-113.

\* cited by examiner

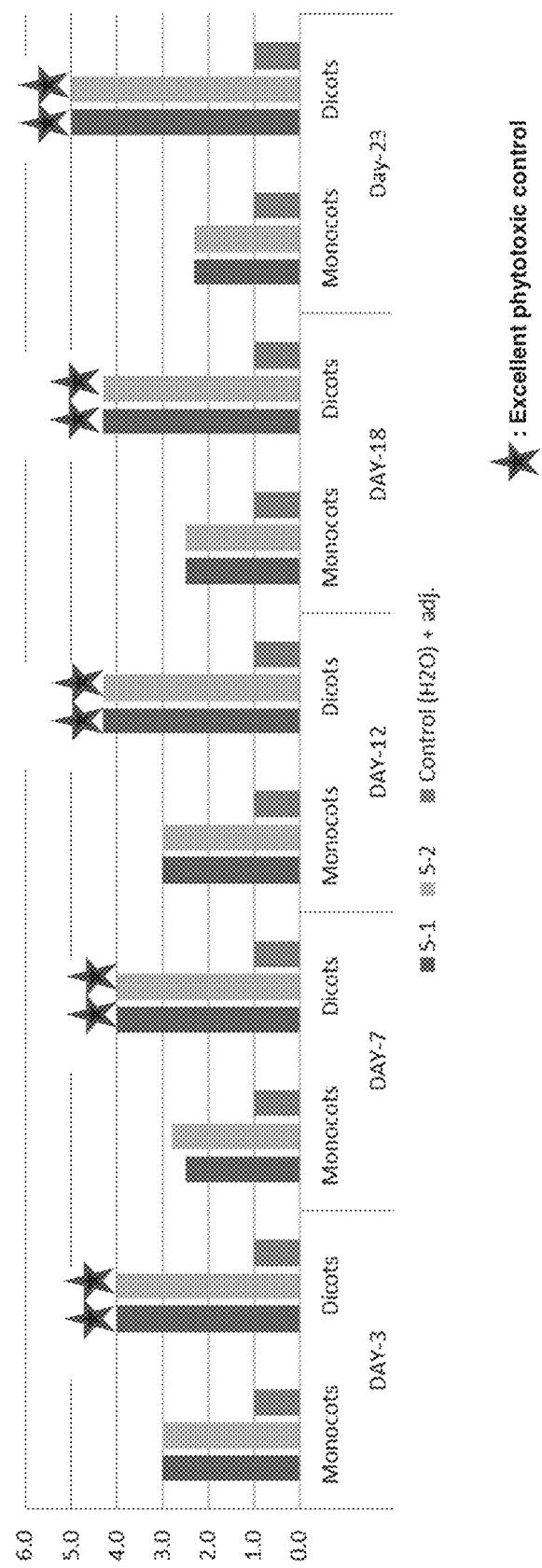

FIG. 7

| Trial Number, Sample # | Notes | Active Nutrient | Solution Formulation | Adjuvants | Active Nutrient: M-Mass/Trial Molarity | Acid Added/L | Solution pH | Days Post Application/Ave. Score. BOLD indicates excellent phytotoxic control (e.g. "severe" or "killed" test) plants. | Plant Species in Trial |
|---|---|---|---|---|---|---|---|---|---|
| T6, S1 | Greenhouse trial | Potassium (K) | K-citrate, plus adjuvants | Buffer-PS | 306.395;2.1 | 0.0 | 7.73 | 11/4.3; 22/4.0 (end) | 21, 22, 26, 19, 3, 14 |
| T6, Control 1 | | None | H20 only | None | None | None | est. 6.5 | 11/1.0 (end) | 21, 22, 26, 19, 3, 14 |
| T7, S2 | Greenhouse trial | Potassium (K) | K-citrate, plus adjuvants | Widespread | 306.395;1.0 | 0.0 | 7.75 | 10/4.2; 20/4.8 (end) | 21, 22, 3, 19, 14, 24 |
| T7, Control 1 | | None | H20 + adjuvants | None | None | None | 7.62 | 10/1.0; 20/1.0 (end) | 21, 22, 3, 19, 14, 24 |
| T7, Control 2 | | None | H20 only | Widespread | None | None | 6.36 | 10/2.3; 20/NR (end) | 21, 22, 3, 19, 14, 24 |
| T13, S1 | Greenhouse trial | Potassium (K) | K-citrate + citric acid as freeze-dried lemon juice, plus adjuvants | Widespread and MSO | 306.395;1.5 | 345g | 5.91 | 11/4.3 (end) | 21, 7, 10 |
| T13, S2 | | Potassium (K) | " | " | 306.395;1.0 | NR | 5.90 | 11/4.0 (end) | 21, 7, 10 |
| T13, Control | | None | H2O + adjuvants | " | None | None | NR | 13/1.0 (end) | 21, 7, 10 |
| T14, S1 | Greenhouse trial. Test 14, 15 and 16 have same actives, diff. adjuvants | Potassium (K) | K-acetate + 30% acetic acid, plus adjuvants | Urea and Widespread | 98.14; 2.0 | 100ml | 5.28 | 1/4.0; 2/4.0; 4/4.0; 7/5.0; 11/4.7; 15/4.8; 22/4.8 (end) | 21,22,10 |
| T14, S2 | | " | " | " | 98.14; 1.5 | 128ml | 5.29 | 1/4.0; 2/4.7; 4/4.0; 7/5.0; 11/4.8; 15/4.8; 22/5.0 (end) | 21,22,10 |

FIG. 7 (cont'd)

| ID | Description | | Treatment | | | Volume | Date | Results | |
|---|---|---|---|---|---|---|---|---|---|
| T14, S3 | " | " | " | " | 98; 1.0 | 64 ml | 5.29 | 2/4.3; 4/4.7; 7/4.5; 11/4.0; 15/4.2; 22/3.7 (end) | 21, 22, 10 |
| T14, Control 1 | | None | H2O + adjuvants | " | None | None | NR | 1/1.0; 2/1.0; 7/1.3; 11/1.3; 15/1.0; 22/1.0 (end) | 21, 22, 10 |
| T14, Control 2 | | None | H2O only | None | None | None | NR | 1/1.0; 2/1.0; 7/1.0; 11/1.0; 15/1.0; 22/1.0 (end) | 21, 22, 10 |
| T15, S1 | Greenhouse trial.Test 14, 15 and 16 have same actives, diff. adjuvants | Potassium (K) | K-acetate + 30% acetic acid, plus adjuvants | Urea, Widespread and MSO | 98:14; 2.0 | 200ml | est'd 5.28 | 1/4.0; 2/4.0; 9/4.7; 10/4.7; 22/5.0 (end) | 21, 22, 10 |
| T15, S2 | | " | " | " | 98:14; 1.5 | 100ml | est'd 5.29 | 2/4.0; 9/4.3; 22/4.7 (end) | 21, 22, 10 |
| T15, S3 | | " | " | " | 98:14; 1.0 | 64ml | est'd 5.29 | 2/4.2; 9/3.7; 22/4.0 (end) | 21, 22, 10 |
| T15, Control 1 | | None | H2O + adjuvants | " | None | None | NR | 2/3.3; 9/1.0; 22/1.0 (end) | 21, 22, 10 |
| T15, Control 2 | | None | H2O only | None | None | None | NR | 2/1.0; 9/1.0; 22/1.0 (end) | 21, 22, 10 |
| T16, S1 | Greenhouse trial.Test 14, 15 and 16 have same actives, diff. adjuvants | Potassium (K) | K-acetate + 30% acetic acid, plus adjuvants | Urea + MSO | 98:14; 2.0 | 200ml | est'd 5.28 | 2/4.0; 5/4.7; 8/4.3; 20/4.3; 33/4.3 (end) | 21, 10, 12 |
| T16, S2 | | " | " | " | 147; 1.5 | 128ml | est'd 5.29 | 2/3.7; 5/4.7; 8/4.3; 20/4.7; 33/4.7 (end) | 21, 10, 12 |
| T16, Control 1 | | None | H2O + adjuvants | " | None | None | NR | 5/1.0; 8/1.0; 20/1.0; 33/NR (end) | 21, 10, 12 |
| T16, Control 2 | | None | H2O only | None | None | None | NR | 5/1.0; 8/1.0; 20/1.0; 33/NR (end) | 21, 10, 12 |

FIG. 7 (cont'd)

| | | | | | | | | |
|---|---|---|---|---|---|---|---|---|
| T22, S1 | Greenhouse trial. | Potassium (K) | K-acetate + succinic acid, plus adjuvants | Urea + Widespread | 98:14; 2.0 | 66g | 5.01 | 1/3.0; 2/3.5; 4/3.9; 5/4.3; 7/4.4 (end) | 22,15,13, 19 |
| T22, S2 | | " | " | " | 98:14; 2.0 | 40g | 5.01 (est'd) | 1/3.0; 2/3.3; 5/4.1; 4/3.3; 5/4.1; 7/4.1 (end) | 22,15,13, 19 |
| T22, Control 1 | | None | H2O + adjuvants | None | None | None | NR | | 22,15,13, 19 |
| T30, S-1 | Greenhouse trial. | Potassium (K) | K-acetate + citric acid, plus adjuvants | Urea + Widespread | 98:14; 2.0 | 150g | 4.05 | 1/1.0; 2/1.0; 4/1.0; 5/1.0; 7/1.0 (end) | 21, 4, 16, 11 |
| T30, S-2 | | " | " | " | 98:14; 1.5 | NR | 4.02 | 1/3.7; 3/3.6; 5/4.0 (end) | 21, 4, 16, 11 |
| T30, S-3 | | " | " | " | 98:14; 1.0 | 70g | 4.02 | 1/3.5; 3/3.6; 5/4.0 (end) | 21, 4, 16, 11 |
| T30, S-4 | | " | " | " | 98:14; 2.0 | 1g | 6.98 | 1/3.4; 3/3.4; 4/4.3 (end) | 21, 4, 16, 11 |
| T30, S-5 | | " | " | " | 98:14; 1.5 | 0.5g | 6.80 | 1/3.4; 3/3.3; 5/3.4 (end) | 21, 4, 16, 11 |
| T30, S6 | | " | " | " | 98:14; 1.0 | <0.5g | 7.03 | 1/3.0; 3/3.0; 5/3.0 (end) | 21, 4, 16, 11 |
| T30, Control 1 | | None | H2O + adjuvants | None | None | None | 4.00 | 1/1.0; 3/1.0; 5/1.0 (end) | 21, 4, 16, 11 |
| T30, Control 2 | | None | H2O + adjuvants | None | None | None | 7.00 | 1/1.0; 3/1.0; 5/1.0 (end) | 21, 4, 16, 11 |
| T31-A, S-1. Test 31 solutions split for 31 A & 31 B | Greenhouse trial. Tests 31-A and 31-B have same actives, diff. adjuvants | Potassium (K) | K-acetate + citric acid, plus adjuvants | Urea + Widespread | 98:14; 2.0 | 50g | 5.01 | 1/3.6; 2/3.6; 3/3.8; 6/4.1; 8/3.8; 31/4.1 (end) | 2, 5, 23, 16, 22 |
| T31-A, S-2 | | " | " | " | 98:14; 1.5 | 29.5g | 5.00 | 1/3.4; 2/3.6; 3/3.6; 6/3.9; 8/3.7; 30/3.9 (end) | 2, 5, 23, 16, 22 |
| T31-A, S-3 | | " | " | " | 98:14; 1.0 | 25.0g | 4.97 | 1/3.2; 2/3.3; 3/3.4; 4/3.5; 8/3.2; 30/4.0 (end) | 2, 5, 23, 16, 22 |
| T31-A, Control "A" | | | H2O + adjuvants | " | 0; 0 | 24g | 5.00 | 1/1.1; 2/1.3; 3/1.0; 6/NR; 8/NR; 30/NR (end) | 2, 5, 23, 16, 22 |

FIG. 7 (cont'd)

| | | | | | | Note: Onion (Plant "2") in Tests 31 A & B was only slightly affected by the formula, all other plants were severely effected or killed. | |
|---|---|---|---|---|---|---|---|
| T31-B, S-1 | Greenhouse trial. Tests 31-A and 31-B have same actives, diff. adjuvants | Potassium (K) | K-acetate + citric acid in sol'n plus adjuvants | Urea + LI-700 | 98:14; 2.0 | 29.5g | 5.01 | 1/3.5; 2/3.8; 3/4.0; 4/4.2; 8/4.3; 30/4.3 (end) | 2, 5, 23, 16, 22 |
| T31-B, S-2 | | | " | " | 98:14; 1.5 | 25.0g | 4.97 | 1/3.5; 2/3.6; 3/3.5; 4/4.1; 8/4.4; 30/4.4 (end) | 2, 5, 23, 16, 22 |
| T31-B, S-3 | | | " | " | 98:14; 1.0 | 24g | 5.00 | 1/3.1; 2/3.4; 3/3.4; 4/3.7; 8/3.6; 30/2.7 (end) | 2, 5, 23, 16, 22 |
| T31-B, Control "B" | | | H20 + adjuvants | | 0; 0 | 24g | 5.00 | 1/1.1; 2/1.3; 3/1.0; 6/NR; 8/NR; 30/NR (end) | 2, 5, 23, 16, 22 |
| | | | | | | | | Note: Onion (Plant #2) in Tests 31 A & B was only slightly affected by the formula, all other plants were severely effected or killed. | |
| T32-A, S-1 Test 32 solutions split for 32 A & 32 B | Greenhouse trial. Tests 32-A and 3B-B have same actives, diff. adjuvants | Potassium (K) | K-acetate + citric acid in sol'n plus adjuvants | Urea + Widespread less than Test 31A | 98:14; 2.0 | 50g | 5.01 (est'd) | 3/3.7; 5/4.3; 9/4.5; 15/4.5 (end) | 18, 17, 6, 2, 22 |
| T32-A, S-2 | | | " | " | 98:14; 1.5 | 29.5g | 5.00 (est'd) | 3/3.7; 5/4.3; 9/4.6; 15/4.6 (end) | 18, 17, 6, 2, 22 |
| T32-A, S-3 | | | " | " | 98:14; 1.0 | 25.0g | 4.97 (est'd) | 3/3.5; 5/3.9; 9/4.3; 15/4.4 (end) | 18, 17, 6, 2, 22 |
| T32-A, | | | H20 + adjuvants | " | 0; 0 | 24g | NR | 3/1.0; 5/NR; 9/NR; 15/NR (end) | 18, 17, 6, 2, 22 |

FIG. 7 (cont'd)

| | | | | | | | |
|---|---|---|---|---|---|---|---|
| Control "A" | | | | | | | |
| T32-B, S-1 | Greenhouse trial. Tests 32-A and 3B-B have same actives, diff. adjuvants | Potassium (K) | K-acetate + citric acid in sol'n plus adjuvants | Urea + Li-700 less than Test 31B | 98.14; 2.0 | 50g | 5.01 (est'd) | 3/3.7; 5/4.1; 9/4.2; 15/4.1 (end) | 18, 17, 6, 2, 22 |
| T32-B, S-2 | | | " | " | 98.14; 1.5 | 29.5g | 5.00 (est'd) | 3/3.7; 5/4.4; 9/4.6; 15/4.6 (end) | 18, 17, 6, 2, 22 |
| T32-B, S-3 | | | " | " | 98.14; 1.0 | 25.0g | 4.97 (est'd) | 3/3.8; 5/4.0; 9/4.3; 15/4.4 (end) | 18, 17, 6, 2, 22 |
| T32-B, Control "B" | | | H20 + adjuvants | " | 0; 0 | 24g | NR | 3/1.0; 5/NR; 9/NR; 15/NR (end) | 18, 17, 6, 2, 22 |
| T41-A, S-1 | Greenhouse trial. Tests 41-A and 41-B have same actives, diff. adjuvants | Nitrogen | Ammonium sulfate + adjuvants | Widespread | 132.14; 2.0 | 0.0 | 5.50 | Monocots: 3/3.0; 7/2.5; 12/3.0; 18/2.5, 23/2.3 (end) Dicots: 3/4.0; 7/4.0; 12/4.3; 18/4.3; 23/5.0 (end) Note: Dicots killed, monocots not. | 2, 22, 10, 3 |
| T41-A, S-1 Control | | | H20 + adjuvants | MSO only | 0; 0 | 0.0 | 7.80 | Mono. and Dicot.:3/1.0; 7/1.0; 12/1.0; 18/1.0; 23/1.0 (end) | 2, 22, 10, 3 |
| 41-B, S-2 | Greenhouse trial. Tests 41-A and 41-B have same actives, diff. adjuvants | Nitrogen | Ammonium sulfate + adjuvants incl. MSO | Widespread + MSO | 264; 2.0 | 0.0 | 5.50 | Monocots: 3/3.0; 7/2.8; 12/3.0; 18/2.5, 23/2.3 (end) Dicots: 3/4.0; 7/4.0; 12/4.3; 18/4.5, 23/5.0 (end) Note: Dicots killed, monocots not. | 2, 22, 10, 3 |
| T41-B, S-2 Control | | | H20 + adjuvants | MSO only | 0; 0 | 0.0 | NR | Mono. and Dicot.:3/1.0; 7/1.0; 12/1.0; 18/1.0; 23/1.0 (end) | 2, 22, 10, 3 |

FIG. 7 (cont'd)

| | | | | | | |
|---|---|---|---|---|---|---|
| T44, S-1 | | Zinc | ZnSO4 | Widespread + MSO | 179.47; 2.0 | 0.0 | 5.10 | 2/2.3; 4/3.1; 5/3.2; 9/3.9; 21/4.6; 27/5.0; 32/5.0 (end) | 6-A, 11-B, 21, 23-B |
| T44, S-2 | | " | " | " | 67; 1.5 | 0.0 | 5.46 | 2/2.7; 4/3.0; 5/2.8; 9/3.5; 21/4.5; 27/4.6; 32/4.8 (end) | 6-A, 11-B, 21, 23-A |
| T44, S-3 | | " | " | " | 45; 1.0 | 0.0 | 5.64 | 2/2.0; 4/2.5; 5/3.0; 9/3.7; 21/4.3; 27/4.4; 32/4.2 (end) | 6-A, 11-B, 21, 23-A |
| T44, Control | | None | None | " | 0.0 | 0.0 | NR | 2/1.0; 4/1.0; 5/1.3; 9/1.3; 21/1.0; 27/1.0; 32/1.0 (end) | 6-A, 11-B, 21, 23-A |
| T47, S-1 | | Potassium (K) | K-acetate + 30% acetic acid plus adjuvants | " | 98; 2.5 | 35.0 | 5.04 | 2/3.8; 5/4.5; 9/4.8; 14/4.9 (end) | 5, 11b, 13, 22b, 23b, |
| T47, S-2 | | " | " | " | 98; 2.0 | 25.0g | 5.05 | 2/3.7; 5/4.0; 9/4.8; 14/4.8 (end) | 5, 11b, 13, 22b, 23b, |
| T47, S-3 | | " | " | " | 98; 1.5 | 18.0 | 5.03 | 2/3.6; 5/4.5; 9/4.4; 14/5.0 (end) | 5, 11b, 13, 22b, 23b, |
| T47, S-4 | | " | " | " | 98; 1.0 | <18 | 5.07 | 2/3.7; 5/4.4; 9/4.8; 14/4.8 (end) | 5, 11b, 13, 22b, 23b, |
| Control | | " | " | " | 0.0 | 0.0 | 7.04 | 2/1.0; 5/1.0; 9/1.0; 14/1.0 (end) | 5, 11b, 13, 22b, 23b, |
| T50, S-1 | Field test on mature weeds. | Potassium (K) | K-acetate + citric acid, plus adjuvants | Canola oil and "Joy" detergent | 98.14; 2.5 | 300g | 5.00 | 3/2.8; 10/2.8 (end) | Mature field weeds |
| T50, S-2 | | " | " | " | 98.14; 2.0 | 300g | 5.00 | 3/3.6; 10/3.6 (end) | Mature field weeds |
| T50, S-3 | | " | " | " | 98.14; 1.5 | 300g | 5.00 | 3/3.5; 10/3.4 (end) | Mature field weeds |
| T50, S-4 Control 1 | | " | " | " | 0; 0 | 0.0 | 7.00 | 3/0.1; 10/0.4 (end) | Mature field weeds |
| T50, S-5 Control 2 | | None | None | None | 0; 0 | 0.0 | 7.00 | 3/0.1; 10/0.1 (end) | Mature field weeds |
| T54, Purslane | Greenhouse trial. | Potassium (K) | K-acetate+ citric acid | Kinetic, DyneAmic, UAN | 98.14; 2.0 | 29g | 5.04 | 4/4.0; 14/5.0; 16/5.0; 18/5.0 (end) | 23A |

FIG. 7 (cont'd)

| | | | | | | | | |
|---|---|---|---|---|---|---|---|---|
| T54, Bmyrd grass 1 | " | " | " | " | " | " | 4/4.5; 14/4.5; 16/5.0; 18/5.0 (end) | 11C |
| T54, Bmyrd grass 2 | " | " | " | " | " | " | 4/4.0; 14/5.0; 16/5.0; 18/5.0 (end) | 11C |
| T54, Feather fingergrass | " | " | " | " | " | " | 4/4.5; 14/5.0; 16/5.0; 18/5.0 (end) | 9A |
| T54, Control | " | None | None | " | 0;0 | " | 4/1.0; 14/1.0; 16/1.0; 18/1.0 (end) | 23A, 11C, 9A |
| T56, S-1 | Greenhouse trial. | Potassium (K) | K-acetate + citric acid, plus adjuvants | Kinetic, urea, and humectant (sucrose) | 98.14; 1.5 | 34g | 5.52 | 3/3.9; 4/4.0; 7/4.3; 10/4.8; 12/5.0; 15/5.0 (end) | 26, 3, 10, 17A |
| T56, Control | " | None | None | None | 0;0 | 0.0 | NR | 3/1.1; 4/1.1; 7/1.1; 10/1.1; 12/1.1; 15/1.1 (end) | 26, 3, 10, 17A |
| T64, S-2 | Greenhouse trial. | Boron (B) | Disodium octaborate tetrahydrate | Kinetic, urea, sucrose | 412.5; 0.5 | 0.0 | est'd 7.78 | 12/4.3; 34/4.6 | 5, 18a, 22, 23b, 26 |
| T64, Control | " | " | None | " | 0;0 | 0.0 | est'd 7.0 | 12/1.0; 34/1.0 | 5, 18a, 22, 23b, 26 |

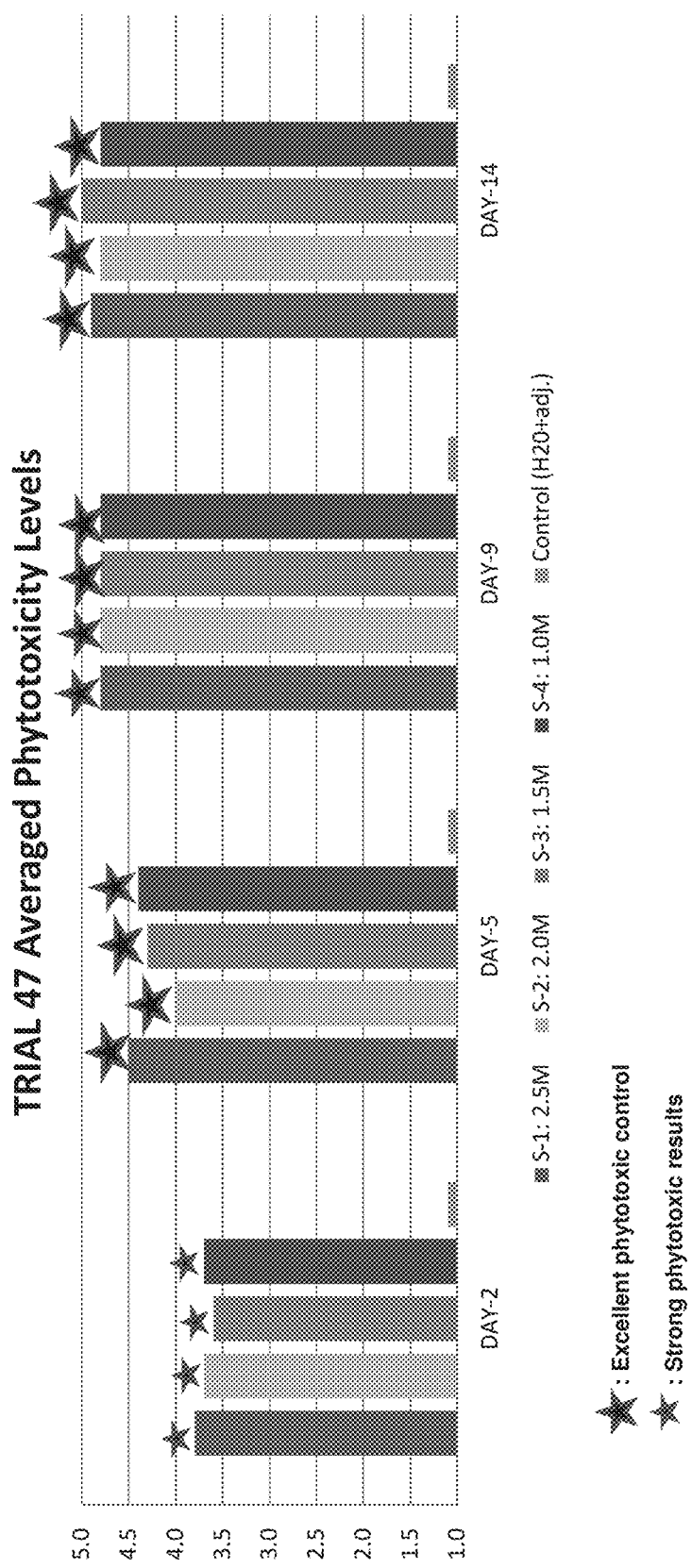

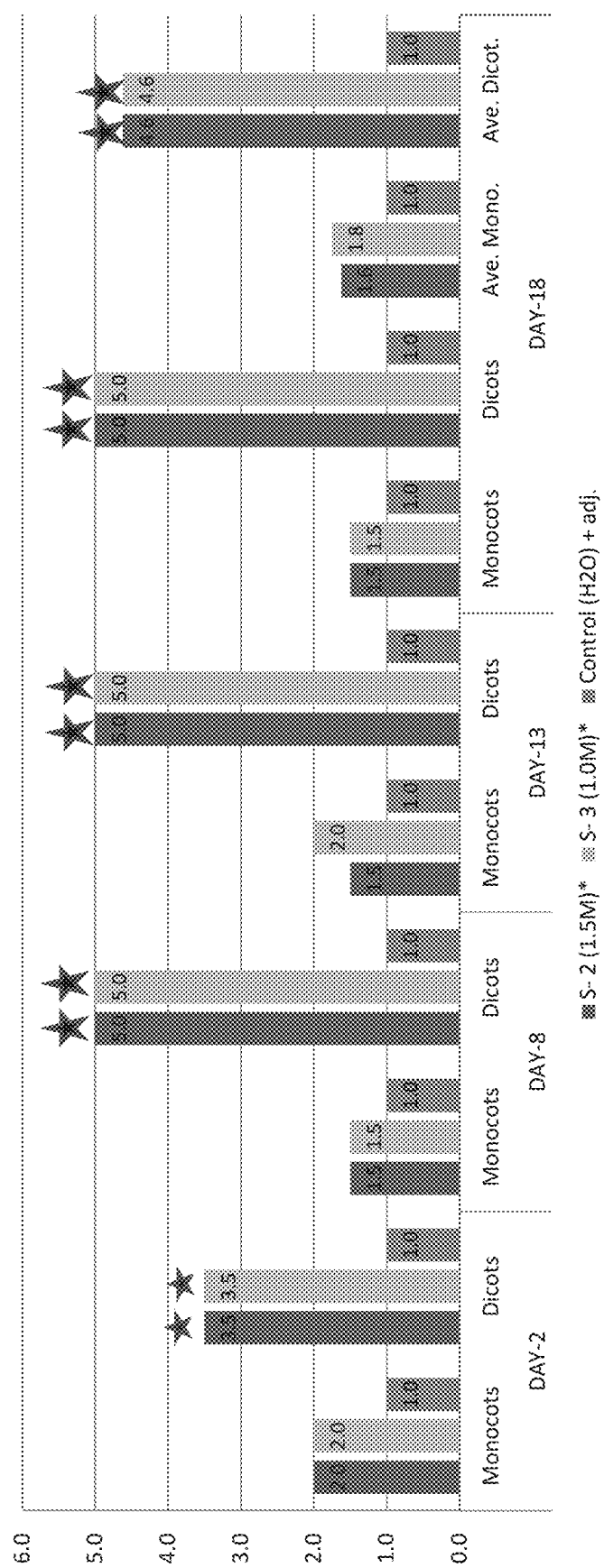

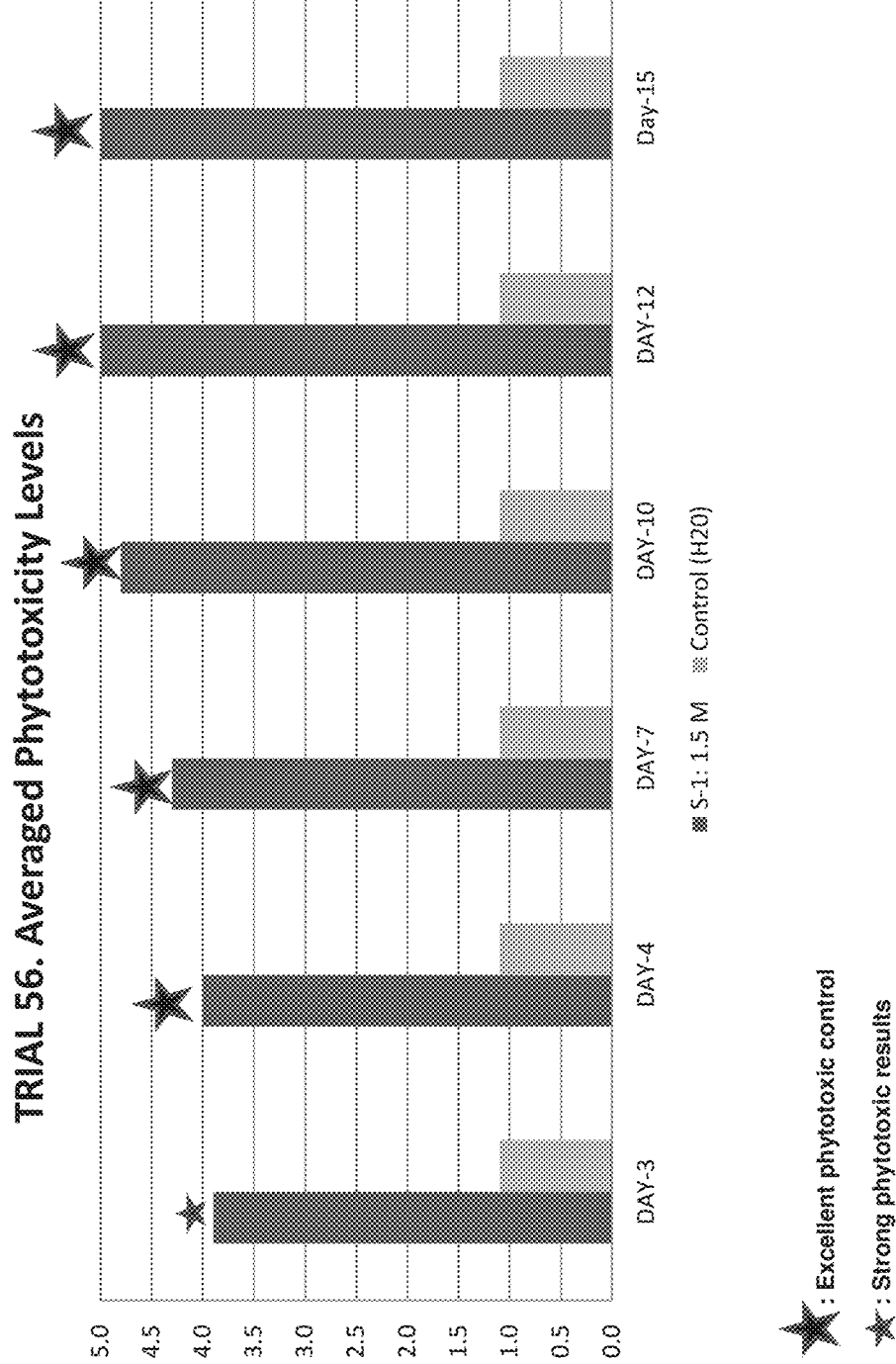

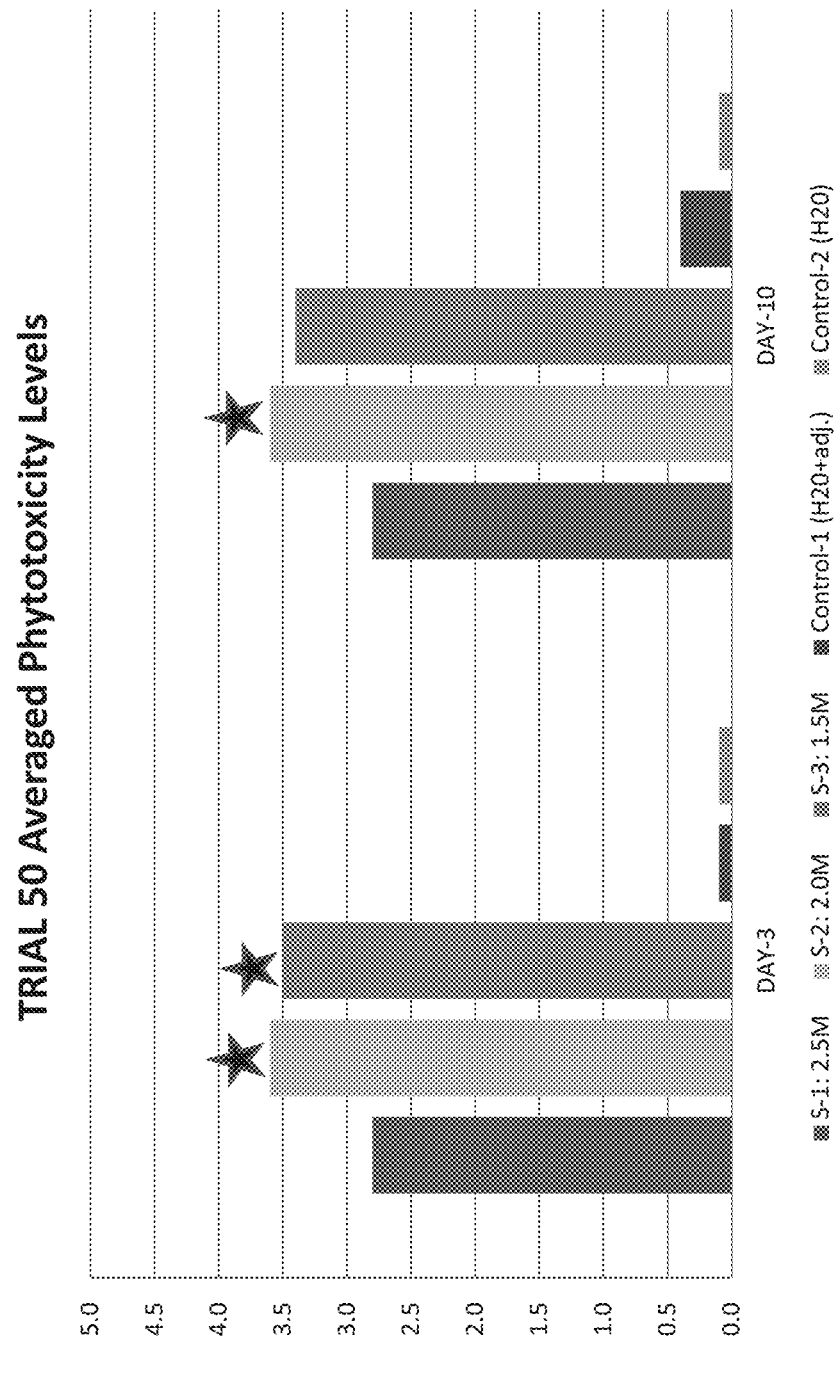

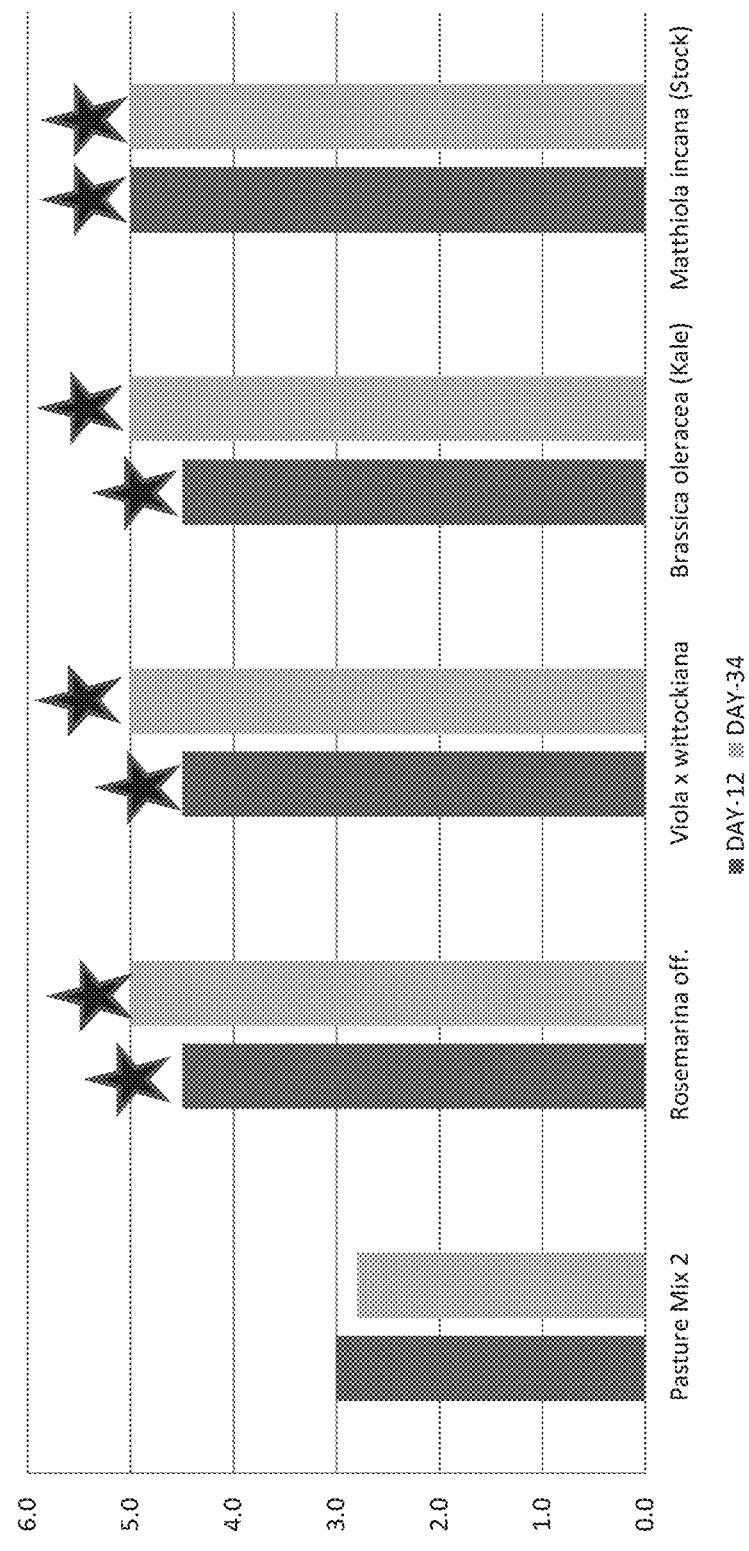

POST-EMERGENCE HERBICIDE

CROSS-REFERENCE TO RELATED APPLICATIONS

The present application is a continuation of U.S. Non-Provisional application Ser. No. 15/916,107, filed Mar. 8, 2018, which claims the benefit of U.S. Provisional Application Nos. 62/469,087, filed Mar. 9, 2017, and 62/609137, filed Dec. 21, 2017 each of which is hereby incorporated by reference in its entirety.

FIELD

Some embodiments relate to a class of post-emergence, non-specific herbicide, comprising a nutrient in aqueous solution, and an adjuvant and a pH of about 4 to about 7. In some embodiments, the post-emergence, non-specific herbicide is systemic. In some embodiments, the post-emergence, non-specific herbicide is topical, for example as a desiccant, or to target specific growths from an established plant.

BACKGROUND

Herbicides comprise a category of agricultural chemicals intended to control or destroy weeds that interfere with the growth and development of cash or ornamental crops, or of vegetation that otherwise require removal for fire safety, aesthetic or other reason. Control of such undesirable vegetation is desirable in farms and orchards; rights-of-way, roadsides, paths and industrial areas; for incidental control of weeds in gardens, parks, and playgrounds (such as school playgrounds); and for other applications typically requiring herbicidal action.

Herbicides can be categorized as having "pre-emergence" action that either prevents germination of weed seeds or kills the emergence seedlings, or "post-emergence" action that kills the unwanted plant as it grows and develops following germination. Post-emergence herbicides that are absorbed into plant tissue and translocate to one degree or another throughout the plant for an herbicidal effect, can be classified as "systemic" herbicides. Systemic herbicides can induce systemic phytotoxicity in a plant, killing or severely damage the entire plant including its roots such that regrowth is either prevented or significantly reduced. Systemic herbicides can be classified as "non-selective" if formulated to kill a wide variety of targeted plant species, or as "selective" if formulated to kill only specifically targeted weeds. Some post-emergence herbicides can also be classified as "topical" herbicides, and can result in topical phytotoxicity, for example as defoliants, or dessicating or killing portions of a plant, for example shoots or growths off of an established plant, such as "suckers" that grow off of an established grape vine.

There currently exists a category of non-systemic post-emergence "burn-down" herbicide that, as a result of the chemical destruction of protective surface tissues kills by severe desiccation and "sun burn". "Commercial and non-organically certified examples of burndown herbicides include glyphosate (e.g., "Roundup" at reduced rates, Monsanto), paraquat dichloride ("Gramazone", Syngenta), and 3,6-dichloro-2-methoxybenzoic acid ("Vanquish", Nufarm). At higher rates Roundup is also an effective "systemic" herbicide that kills both the foliage and roots of the plant and thus can prevent regrowth. Burndown herbicides do not typically kill below-ground tissues and regrowth can occur.

The active ingredients of a variety of herbicides certified as "organic" by the Organic Materials Review Institute ("OMRI") include household vinegar (acetic acid 5-7%), acetic acid (e.g., 30% acetic acid, glacial acetic acid), "citrus oil", lemon oil, clove oil, cinnamon oil, and various combinations of these and similar substances. The active ingredients of OMRI certified proprietary herbicides can include one or a combination of fatty acids, examples of which are caprylic and capric acids ("Suppress", Westbridge Agricultural Products) and pelargonic acid ("Scythe", Dow Agro Sciences). Ammonium nonanoate salt is the active ingredient of the OMRI burndown herbicide "AXXE" (BioSafe Systems). To the best of Applicant's knowledge, all herbicides currently certified by OMRI are "burndown" herbicides, and are represented as non-systemic in their action. Roots or below-ground meristems (typical of grasses) are left unaffected, re-grow, and can require additional treatments for control.

SUMMARY

Some embodiments include a method of inducing phytotoxicity in a plant. The method can comprise administering an aqueous composition to foliar portions of the plant, in which the aqueous composition comprises or consists essentially of at least one nutrient compound selected from the group consisting of a potassium compound, a phosphorus compound, a nitrogen compound, a magnesium compound, a sulfur compound, a calcium compound, and a micronutrient, wherein the nutrient compound comprises a nutrient. The aqueous composition can comprise at least one adjuvant. The pH of the aqueous composition can be about 4 to about 7 (Howard et al., 1998, Mengel, 2002, Marschner, 1995). The nutrient can be absorbed by the plant in excess, so as to induce phytotoxicity in the plant. In some embodiments, the method comprises systemically administering the aqueous solution. In some embodiments, the phytotoxicity comprises killing the plant, and the method comprises systemically administering the aqueous solution, thus killing the plant. In some embodiments, the aqueous composition has systemic "burn-down" activity. In some embodiments, the phytotoxicity is in a portion of the plant, and the method comprises topically administering the aqueous solution, thereby inducing topical phytotoxicity in the plant. In some embodiments, inducing phoytotoxicity in the plant comprises systemic and topical phytotoxicity. In some embodiments, the phytotoxicity comprises desiccation of the plant. In some embodiments, the plant is a crop that matures late in the season and stays green. In some embodiments, the plant is selected from the group consisting of cotton, potatoes, soybeans, or a vegetable for the production of seeds. In some embodiments, desiccation occurs prior to the harvest of a grain crop in proximity to the plant. In some embodiments, the adjuvant comprises a surfactant, a humectant, or both. In some embodiments, the excess nutrient absorbed by the plant causes terminal physiological disruption and killing of the plant. In some embodiments, the excess nutrient absorbed by the plant causes opening of stromata of the plant, thereby desiccating the plant. In some embodiments, the aqueous composition further comprises an organic acid or a mineral acid. In some embodiments, the pH of the composition is about 4.5 to about 5.5. In some embodiments, the concentration of the nutrient in the aqueous composition is about 1 M to about 2 M. In some embodiments, the aqueous composition comprises the organic acid, and the organic acid is selected from the group consisting of acetic acid, citric acid, lactic acid, formic acid, succinic acid, tartaric acid, malic acid, and oxalic acid. The method of any one of claims 6-8, wherein the aqueous composition comprises the mineral acid, for example HCl. In some embodiments, the nutrient compound is selected from the group consisting of: potassium acetate, potassium lactate, potassium formate, potassium citrate, and potassium bitartrate, and wherein the nutrient comprises potassium. In some embodiments, the nutrient compound is selected from the group consisting of: a potassium compound, a phosphorus compound, a nitrogen compound, a sulfur compound, a calcium compound, a micronutrient, and a combination of two or more of the listed items. In some embodiments, the micronutrient does not comprise Fe, for example chelated iron (and as such, the aqueous composition does not comprise Fe, and/or does not comprise chealated iron). In some embodiments, the nutrient compound comprises magnesium sulfate, and wherein the nutrient comprises magnesium. In some embodiments, the nutrient compound comprises ammonium sulfate, and wherein the nutrient comprises nitrogen. In some embodiments, the nutrient compound comprises an ion comprising K, P, N, Mg, S, Ca, or the micronutrient, and an oppositely-charged ion, in which the oppositely-charged ion is not an herbicide in the quantities of the composition. In some embodiments, the nutrient compound does not comprise glyphosate. In some embodiments, the composition is applied as a water-based spray. In some embodiments, the absorption of the nutrient is forestalled for 2-4 days. In some embodiments, the composition has a low point of deliquescence (POD), whereby the composition is retained in semi-liquid state on the foliar portion of the plant for 2-4 days. In some embodiments, the plant is a dicot. In some embodiments, the plant is a monocot. In some embodiments, the plant is a dicot, and the plant is disposed among monocots, for example grass, and the monocots are not killed. In some embodiments, the nutrient compound comprises ammonium sulfate. In some embodiments, the nutrient comprises nitrogen at a concentration of at least 2M in the composition. In some embodiments, the aqueous composition further comprises a solubilizing agent as described herein. In some embodiments, the plant is at least one selected from the group consisting of *Allium ampeloprasum, A. cepa, A. tuberosum, Antirrhinum majus, Brassica oleracea, Calendula officinalis, Calibrachoa* sp., *Celosia* sp., *Cineraria meritima, Chloris aequitrilobia, Cosmos* sp., *Cymbalaria aequitriloba, Echinochloa* sp., *Festuca* sp., *Fragaria×ananassa, Gallium odoratum, Gazania rigens, Lantana camara, Leucanthemum paludosu, Lobelia erinus, Paludosum, Lobularia maritima, Nemophila menziesii discoidalis, Nicotiana* sp., *Pisum sativum, Portulaca oleracia, Rosmarina officinalis, Santivitalia* sp., *Viola hederacea, Viola×wittockiana, Lolium perenne, Dactylis glomerata, Festuca arundinacea, Trifolium subterraneum, Eschscholzia californica, Collinsia heterophyllia, Matthiola incana, Nemophila maculate* and *Linum lewisii*. In some embodiments, the plant is at least one selected from the group consisting of *Allium ampeloprasum, A. cepa, Antirrhinum majus, Brassica oleracea, Calendula officinalis, Calibrachoa* sp., *Celosia* sp., *Cineraria meritima, Cosmos* sp., *Festuca* sp., *Fragaria×ananassa, Gallium odoratum, Gazania rigens, Lantana camara, Leucanthemum paludosu, Paludosum, Lobularia maritima, Nemophila menziesii discoidalis, Nicotiana* sp., *Pisum sativum, Santivitalia* sp., *Viola hederacea, Viola×wittockiana, Lolium perenne, Dactylis glomerata, Festuca arundinacea, Trifolium subterraneum, Eschscholzia californica, Collinsia heterophyllia, Nemophila maculate* and *Linum lewisii*. In some embodiments, the method further comprises a second administration within 14 days of the first administration of the composition. In some embodiments, the rate of application of the composition is 20-40 gallons per acre. In some embodiments, the composition further comprising a burn down herbicide. In some embodiments, the burn down herbicide comprises an organic acid composition selected from the group consisting of: a composition comprising caprylic (octanoic) acid and capric (decanoic) acid; a composition comprising pelargonic (nonanoic) acid and $C_6$-$C_{12}$ fatty acids; and a composition comprising ammonium nonanoate, and an ammonium salt of pelargonic acid. In some embodiments, the composition further comprises a second herbicide, wherein the second herbicide is a non-nutrient herbicide. In some embodiments, the second herbicide comprises an herbicide selected from Table 3.1. In some embodiments, the nutrient comprises a micronutrient, and the plant is positioned in a right-of-way, road-sides, or in the absence of crop or ornamental vegetation. In some embodiments, the nutrient comprises a macronutrient, and wherein the plant is positioned in the presence of a crop or ornamental vegetation. In some embodiments, the nutrient compound does not comprise chelated iron. In some embodiments, the nutrient compound does not comprise iron.

Some embodiments include a kit comprising: a first unit quantity of a nutrient compound selected from the group consisting of: a potassium compound, a phosphorus compound, a nitrogen compound, a magnesium compound, a sulfur compound, a calcium compound, and a micronutrient, in which the nutrient compound comprises a nutrient. The kit can include a second unit quantity of organic, fatty, or mineral acid. The kit can include an adjuvant. In the kit the ratio of the first unit quantity to the second unit quantity is configured to achieve a pH of about 4 to about 7 if the first unit quantity is constituted to a molarity of 0.5-2.5 in water having a pH of about 7. In some embodiments, the first unit quantity is comprises potassium salt and wherein the potassium salt is potassium citrate and the organic acid is glacial acetic acid, and wherein the ratio of K citrate to glacial acetic acid is about 1 mol:0.7-3.5 mol acetic acid. In some embodiments, the nutrient compound is selected from the group consisting of: a potassium compound, a phosphorus compound, a nitrogen compound, a sulfur compound, a calcium compound, a micronutrient, and a combination of two or more of the listed items. In some embodiments, the organic or mineral acid is selected from the group consisting of acetic acid (e.g., 30% acetic acid, glacial acetic acid), citric acid, lactic acid, formic acid, succinic acid, tartaric acid, malic acid and oxalic acid. In some embodiments, the first unit quantity is of the potassium compound, and wherein the potassium compound is selected from the group consisting of: potassium acetate, potassium lactate, potassium formate, potassium citrate, and potassium bitartrate. In some embodiments, the first unit quantity is of the nitrogen compound and wherein and the nitrogen compound is ammonium nitrate. In some embodiments, the first unit quantity is of the magnesium compound and wherein the magnesium compound is magnesium sulfate. In some embodiments, the nutrient compound comprises an ion comprising K, P, N, Mg, S, Ca, or the micronutrient, and an oppositely-charged ion, in which the oppositely-charged ion is not an herbicide if the first unity quantity is constituted to a nutrient concentration of about 0.5 to 2.0M. In some embodiments, the kit does not comprise glyphosate. In some embodiments, the kit further comprises a solubilizing agent as described herein. In some embodiments, the nutrient compound does not comprise chelated iron. In some embodiments, the nutrient compound does not comprise iron.

Some embodiments include an aqueous herbicide composition comprising or consisting essentially of at least one nutrient compound selected from the group consisting of: a potassium compound, a phosphorus compound, a nitrogen compound, a magnesium compound, a sulfur compound, a calcium compound, and a micronutrient, wherein the nutrient compound comprises a nutrient at a concentration of at least about 0.5 M in the aqueous herbicide composition. The composition can comprise an organic or mineral acid. The composition can comprise an adjuvant. The composition can have a pH of about 4 to about 7. In some embodiments, the nutrient concentration is about 0.5M to 2.5M. In some embodiments, the organic or mineral acid is selected from the group consisting of: acetic acid (e.g., 30% acetic acid, glacial acetic acid), citric acid, lactic acid, formic acid, malic acid, succinic acid, tartaric acid, and oxalic acid. In some embodiments, the nutrient compound is selected from the group consisting of: a potassium compound, a phosphorus compound, a nitrogen compound, a sulfur compound, a calcium compound, a micronutrient, and a combination of two or more of the listed items. In some embodiments, the nutrient compound is a potassium salt selected from the group consisting of: potassium acetate, potassium lactate, potassium formate, potassium citrate, and potassium bitartrate. In some embodiments, the nutrient compound is a nitrogen compound and wherein and the nitrogen compound is ammonium sulfate. In some embodiments, the nutrient is magnesium and wherein the magnesium compound is magnesium sulfate. In some embodiments, the nutrient is at a concentration of about 0.5 M-2.5 M. In some embodiments, the nutrient is potassium citrate and the organic or mineral acid is glacial acetic acid, and wherein the ratio of potassium citrate to glacial acetic acid is about 1 mol:0.7-3.5 mol acetic acid. In some embodiments, the nutrient compound comprises: an ion comprising K, P, N, Mg, S, Ca, or the micronutrient, and an oppositely-charged ion, in which the oppositely-charged ion is not an herbicide in the quantities of the composition. In some embodiments, the aqueous herbicide composition does not contain glyphosate. In some embodiments, the adjuvant comprises a surfactant as described herein, In some embodiments, the adjuvant comprises a humectant as described herein. Some embodiments include a container containing 0.5 liters to 10 liters of any of the aqueous herbicide compositions described herein. In some embodiments, the composition further comprises a solubilizing agent as described herein. In some embodiments, the nutrient compound does not comprise chelated iron. In some embodiments, the nutrient compound does not comprise iron.

Some embodiments include a method of preparing an herbicidal composition comprising: contacting a nutrient compound (in which the nutrient compound comprises a nutrient) with water to a nutrient concentration of at least about 0.5 M so as to form an aqueous nutrient solution, The nutrient compound can be selected from the group consisting of a potassium compound, a phosphorus compound, a nitrogen compound, a magnesium compound, a sulfur compound, a calcium compound, and a micronutrient. The method can further comprise adjusting the pH of the aqueous nutrient solution to about 4 to about 7 with an organic or mineral acid, thus preparing the composition. In some embodiments, the nutrient concentration is about 0.5M to 2.5M. in some embodiments, the nutrient compound comprises: an ion comprising K, P, N, Mg, S, Ca, or the micronutrient, and an oppositely-charged ion, in which the oppositely-charged ion is not an herbicide in the quantities of the composition In some embodiments, the nutrient compound does not comprise chelated iron. In some embodiments, the nutrient compound does not comprise iron.

BRIEF DESCRIPTION OF THE DRAWINGS

FIG. 5 depicts the average toxicity scores for the four plants tested in Trial 41, which tested an embodiment of an herbicide composition and method of using the same. The plants were numbered 22, 2, 3, and 10, corresponding to mixed monocotyledonous and dicotyledonous Pasture Blend 2 and *Allium cepa* (Onion "Torpedo Red"), and dicotyledonous *Antirrhinum majus* (Snapdragon) and *Cineraria meritima* (Dusty Miller, "Silver Dust" (Refer to Tables 4A and 4B for plant species identification). Both of the samples S-1 and S-2 were solutions of 2.0 Molar of ammonium sulfate having a pH of 5.5. (Refer to Tables 6A and 6B for trial solutions, details and results). Results of Trial 41: For broadleaf (dicotyledonous) species of Sample S-1 at 2.0 Molar concentration, excellent phytotoxic effects from 4.0 to 5.0 ("severe-to-fatal") resulted from Day 3 through trial conclusion at Day 23. For monocotyledonous grass and liliaceae species of Sample S-2 at 2.0 Molar concentration, an initial moderate effect of 3.0 had decreased to 2.3 ("slight"). Controls sprayed with only water and adjuvant mix showed no effects. Dicots included in the Pasture 2 samples of S-1 and S-2 were all dead by Day 7. However, separate toxicity results for the monocots and dicots present in the Pasture Blend 2 mix were not recorded, and are not presented in FIG. 5.

FIG. 7 summarizes data from Tables 6A and 6B in a concise format for ease of viewing.

FIG. 8 depicts the average toxicity scores for the five plants tested in Trial 47, which tested an embodiment of an herbicide composition and method of using the same. The plants were numbered P2, 5, 11A, 13, and 23A, corresponding to monocotyledonous and dicotyledonous Pasture Blend 2. *Brassica oleracea* (Kale), *Dichondra repens, Fragraria×ananassa* (Strawberry), and *Rosmarina officinalis* (Rosemary) (Refer to Tables 4A and 4B for plant species identification.). Solutions S-1, S-2, S-3, and S-4 correspond to solution of potassium acetate of molarities 2.5, 2.0, 1.5, and 1.0 respectively. The acidity of each test solution was adjusted to approximately pH 5.0 with crystalline citric acid. The adjuvants were canola oil, and JOY liquid detergent. Results of Trial 47 indicates excellent phytotoxic effects of between 4.0 ("severe-to-fatal") and 5.0 ("dead") for all test solution concentrations by Day 5. However, "severe-to-fatal" result were noted on three of the five test species as early as Day 2. This is believed to be too rapid a burn-down reaction to allow optimal absorption of the active ingredient. The test spray for the Controls included the adjuvants. No visible effects were noted for Controls." Results of Trial 47: All molarities yielded excellent controls of between 4.0 to 4.8 at Day 5 through Day 16, the conclusion of test.

FIG. 9 is a graph showing the average toxicity scores for the five plants tested in Trial 46, which tested an embodiment of an herbicide composition and method of using the same. The plants were numbered P2, 5, 11A, and 13, corresponding to Pasture Blend 2, *Brassica oleracea* (Kale), *Dichondra repens, Fragraia×ananassa* Strawberry (Refer to Tables 4A and 4B for plant species identification). Solutions S-1 and S-2 correspond to solutions of Monopotassium phosphate ($KH_2PO_4$) at concentrations of 2.0 molarity (Solution 1) and 1.5 molarity (Solution 2). The unadjusted acidities of the S-1 and S-2 were 4.09 and 4.14 respectively. The adjuvants in Trial 46 were WIDESPREAD silicone surfactant and methylated seed oil (MSO). Results of Trial 46 indicate "severe-to-fatal" results only for broadleaf (dicot) samples from applications of both 2.0 and 1.5 molar test solution at Day 8 through completion of the test at Day 18. There was minimal effect during this period for the same solutions applied to the three grasses in P-2. Controls sprayed with water and adjuvant mixture only showed no effects. These results suggest the possibility of Monopotassium phosphate as a broadleaf herbicide in turf.

FIG. 10 depicts the average toxicity scores for the four plants tested in Trial 56, which tested an embodiment of an herbicide composition and method of using the same. The plants were numbered 3, 10, 18, and 26, corresponding to *Antirrhinum majus* (Snapdragon), *Cineraria maritima* (Dusty miller), *Lobularia maritima* (Alyssum), and *Violax wittockiana* (Viola) (Refer to Tables 4A and 4B for plant species identification). The test solution was Potassium acetate at a concentration 1.5 molar, adjusted to pH 5.52 with crystalline citric acid. The adjuvants in Trial 56 were KINETIC silicone surfactant, urea, and sucrose as a humectant to extend the semi-liquid state of the test solution of plant surfaces. Results of Trial 56, Potassium acetate at 1.5 molarity yielded strong phytotoxic control at Day 3, and excellent phytotoxic control at Day 4 through Day 15 and conclusion of test. When last observed on Day 16, treated plants appeared dead with no regrowth. Controls appeared to be growing normally with no tissue damage apparent.

FIG. 11 depicts the average toxicity scores for the plants tested in Trial 50, which tested an embodiment of an herbicide composition and method of using the same. The herbicide composition comprised K-acetate; molarity 2.5, 2.0, and 1.5. Results of Trial 50: 2.0 and 1.5 molarities yielded strong controls of between 3.5 to 3.6 at Day 3 through Day 10, the conclusion of test. 2.5 molarity resulted in less phytotoxicity than lower molarities.

FIG. 14 is a graph showing the average toxicity scores for the plants tested in Trial 64 in which the herbicide Disodium octaborate tetrahydride (SOLUBOR®); 0.5 molar solution. Results of Trial 64: Excellent phytotoxic control at 0.5 molarity was observed of all broadleaf species in the trial at Days 12 through 34, the conclusion of the trial. Partial control during this period was observed among the grass species in the trial.

DETAILED DESCRIPTION

Figure 1:
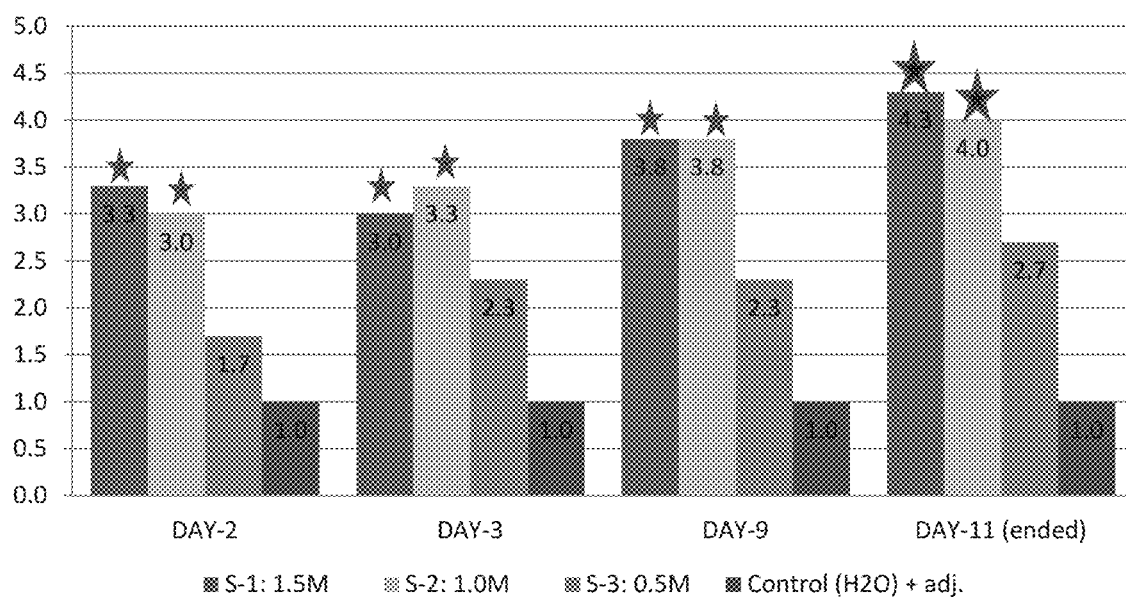
FIG. 1 is a graph showing the average toxicity scores for the three plants tested in Trial 13, which tested an embodiment of an herbicide composition and method of using the same. The plants were numbered 21, 7, and 10, corresponding to Pasture Blend 1, *Calendula officinalis* (Common marigold) and *Cineraria meritima* (Dusty miller "Silver Dust") (Refer to Tables 4A and 4B for plant species identification). Solution 1 (S-1) corresponds to a 1.5 molar solution of potassium acetate, pH 5.91 achieved with citric acid as freeze-dried lemon juice, and the inactive adjuvants urea, WIDESPREAD® silicone surfactant (Loveland Products), and methylated seed oil (MSO). S-2 is a similar solution of 1.0 molarity, pH 5.90. S-3 is a similar solution of 0.5 molarity, pH 5.90. (Refer to Tables 6A and 6B for trial solutions, details and results). Results of Trial 13 indicate an excellent phytotoxic effect) (refer to Table 5 for Toxicity Level codes) of 4.3 ("severe-to-fatal") resulted at Day 11 at a solution of 1.5M, and of 4.0 ("severe") at Day 11 at a solution of 1.0M. Controls sprayed with water and a proprietary adjuvant mixture showed no visible effect by Day 11 when test was concluded.

Embodiments herein include a class of post-emergence, non-selective herbicide to be applied "topically" as a water-based spray. In some embodiments, the herbicide induces systemic phytotoxicity. In some embodiments, the herbicide induces topical phytotoxicity (e.g. as a desiccant). The herbicide of some embodiments comprises a macro-nutrient and/or micro-nutrient in phytotoxic concentrations for the target plant(s), and can be formulated for a pH and viscosity suitable for the target plant to systemically absorb quantities of the macro-nutrient and/or micro-nutrient in physiological excess, including absorption in the roots. Embodiments herein differ significantly from existing post-emergence, systemic, non-selective herbicides, for example by formulation, mode of action, absence of toxic soil residual, toxicity to target plants, and minimal off-target herbicidal effects.

Also unique in some embodiments is the suitability of formulations to qualify for use in "organic" agriculture, and for the preparation of separate formulations either to augment or avoid interference with seasonal fertilization of crops and landscape. To the best of Applicant's knowledge, no such herbicide with these characteristics currently exists in the industry.

There is currently available on the market a class of proprietary "burn-down" herbicides the active ingredients of which are one or a combination of organic acids or salts thereof. These are typically non-selective targeting both grasses and broadleaf weeds. Examples include Suppress®: Westbridge Agricultural Products, EPA Registration Number 51517-9, the active ingredients of which are caprylic (octanoic) acid (47%) and capric (decanoic) acid (32%); Scythe®: Dow AgroSciences, EPA Registration Number 62719-529, the active ingredients of which are pelargonic (nonanoic) acid (57.0%) and "other fatty acids $[C_6-C_{12}]$" (3%); and Axxe®: BioSafe Systems, EPA Registration Number 70299-23, the active ingredient of which is ammonium nonanoate (40%), an ammonium salt of pelargonic acid. Examples of solutions of this category of formulation, which as noted herein, can be useful in conjunction with some embodiments, are as follows:

Aquatic solution of potassium acetate+pelargonic acid.
Aquatic solution of potassium nitrate+pelargonic acid.
Aquatic solution of ammonium nonanoate+citric acid.
Aquatic solution of ammonium sulfate+decanoic acid, et al. . . .

There is currently available on the market a class of proprietary "burn-down" herbicides the active ingredient of which the active product is chelated iron. These products are similar to liquid products formulated to treat iron deficiencies in plants. The iron is bound in a chelating agent (e.g. Fe HEDTA, hydroxyethylenediaminetriacetic acid) that keeps it soluble and readily available for plant uptake, causing iron oxidation. Broadleaf weeds (dicots) absorb Fe HEDTA more easily and in higher quantities than turf grasses (monocots). Broadleaf weeds are impacted almost instantly while the turf remains unharmed, Iron oxidation causes severe tissue damage. Treated plants dry up and die hours after treatment. (Smith-Fiola and Gill, 2014) The primary use of iron based herbicides in for broadleaf control in turf. However, it can also be used for control of individual broadleaf weeds on driveways, sidewalks and paths. Fe HEDTA are considered "burn-down" herbicides. Translocation of iron throughout the plant sufficient to result in systemic herbicidal action is neither expected, nor is it necessarily required in these iron-based burn-down herbicides.

Examples of proprietary chelated iron herbicides include Natria®, Bayer, 67702-26-72155, the active ingredient of which is 26.5% Iron HEDTA; Fiesta®, Engage Agro USA, EPA Registration Number 67702-26-87865, the active ingredient of which is 26.5% Iron HEDTA; and Iron X!® Selective Weed Killer, Gardens Alive, EPA Registration Number 67702-26-56872, the active ingredient of which is 26.5% Iron HEDTA.

The active agents of these "burn down" products are applied to the surface of the plant, but are not efficiently translocated to the oil, stems, roots and other tissues. Consequently, portions of the plant below the soil surface and protected from the "burn down" herbicidal spray typically regenerate the plant over the following weeks or months. This can require re-application of the topical "burn down" herbicide for continued weed control. (Abouziena, et at, 2009, which is hereby incorporated by reference in its entirety)

Without being limited by theory, the herbicidal action of conventional non-systemic post-emergence "burn-down" herbicides results from the destruction of the waxy surface cuticle and underlying epidermis of the plant by the organic (e.g., carboxylic) or mineral acids or their salts, by various oils, or by other agents that cause subsequent severe desiccation. Treatment with this class of herbicide kills only plant tissue receiving the spray. The active materials are not generally absorbed by the plant to a degree sufficient to result in herbicidal action beyond the location of tissue directly receiving the sprayed herbicide. Consequently, any above-surface and all subsurface portions of the weed that were untreated can survive, typically regrow, and the plant must be treated again.

Furthermore, without being limited by theory, for a systemic herbicide to kill the entire plant, it would have to transfer across several surface tissue layers and enter the leaf cell cytoplasm from which it can then be transported throughout the plant. The first layers is commonly a waxy and cutaneous layer at the surface of the leaf, stem, flower or fruit that serve as passive barriers for the control of water loss from within the plant, and provide resistance to disease, ultraviolet radiation, and other stresses potentially damaging to the internal tissues of the plant below the surface tissues. Movement of ions across the waxy and cuticular layers to the cell wall is a nonmetabolic process driven by diffusion and electrochemical potential. (Oosterhuis, 2009; Wojcik, 2004, each of which is hereby incorporated by reference in its entirety).

Beneath the cuticle, the "pavement cells" of the upper epidermis form the next barrier to penetration from outside the plant, followed by the cell walls and plasma membranes of the living cells themselves. Transport of ions across the epidermal layers is driven by diffusion, and also by ion exchange facilitated by ectodesmata, structures within the epidermal wall below the cuticle. These polar pathways allow the continued passage of select nutrient ions across the epidermis and to the plasma membrane. Although this membrane is a barrier to solutes of high molecular weight, it does allow selective transport of smaller nutrient ions into the cytoplasm against the concentration gradient. (Berndt, 1987; Christensen, 2005; Taiz et al., 2015; Wojcik, 2004, each of which is hereby incorporated by reference in its entirety). After entering the cytoplasm, the fate of the interloping ion is determined by multiple physical, chemical, and electrochemical factors. Local inter- and intra-cellular movement or "transport" employs diffusion, active and passive movement utilizing pores or specialized proteins embedded within cell membranes, or other processes. Long distance "translocation" utilizes cells connected into tubules that carry water and nutrient solutions from roots to leaves in the case of xylem tubules, and from leaves to roots, flowers, points of tissue growth, fruits and elsewhere in the case of phloem tubules. Different molecules and ions, being of differing size, electrochemical charge, polarity, and so forth, move at different rates within and among cells, and throughout a plant. (Marschner, 1995, which is hereby incorporated by reference in its entirety).

Post-emergence systemic herbicide that will kill the entire plant, and which can be used for all plants generally (not limited to specific species), can offer advantages over conventional, non-systemic, post-emergence "burn-down" herbicides which typically require repeat administration. In some embodiments, a post-emergence systemic herbicide comprises an organic or mineral acid or its salt, and an amount of absorbable macro-nutrient to create systemic nutrient toxicity sufficient to kill the entire plant. It is contemplated that such formulations, in accordance with some embodiments herein, can serve as a post-emergence systemic herbicide with activities on plants in general.

Herbicides

In some embodiments, a class of post-emergence, non-specific herbicide is described. The herbicide can comprise at least one nutrient, which can comprise, consist of, or consist essentially of a "macronutrient" or "micronutrient," The herbicide can comprise as a non-active ingredient at least one penetrant, at least one adjuvant (for example, comprising, consisting of, or consisting essentially of a surfactant and/or humectant), or additional adjuvants to improve the effectiveness of the herbicide. In some embodiments, the herbicide comprises an aqueous formulation. In some embodiments, the herbicide is systemic. In some embodiments, the herbicide is topical (e.g., as a defoliant). The herbicide may also be referred to herein as an "herbicide composition," "herbicidal composition," or the like. It is understood that in accordance with herbicides, kits, and methods herein, nutrients (macronutrients and/or micronutrients) can be provided either by themselves, or as part of a compound. As used herein "nutrient compound" has its customary and ordinary meaning as understood by one of skill in the art in view of this disclosure. It refers to compounds that comprise one or more nutrients, either alone, or in addition to other substances. When the term "nutrient," or a particular nutrient is used herein, it will be understood that the nutrient is contemplated as being present as part of a nutrient compound (a nutrient compound comprising the particular nutrient in the case of the particular nutrient).

As used herein, "macronutrient" has its customary and ordinary meaning as understood by one of skill in the art in view of this disclosure. It refers to a nutrient normally required in relatively large amounts by plants for optimal growth, development, and reproduction. Example macronutrients are shown in Table 1A. In accordance with embodiments herein, a "macronutrient" can comprise an elemental macronutrient or its compound.

As used herein, "micronutrient" has its customary and ordinary meaning as understood by one of skill in the art in view of this disclosure. It refers to a nutrient normally required in relatively small or trace amounts by plants for optimal growth, development, and reproduction. Example macronutrients are shown in Table 1B. selected from, but limited to, that category and consisting of elemental micronutrient or its compound.

TABLE 1A

Example macronutrients in plants. (Havlin, et al. 2014)

| | Nutrient | |
|---|---|---|
| Classification | Name | Symbol |
| Macronutrients | (Hydrogen) | H |
| | (Carbon) | C |
| | (Oxygen) | O |
| | Nitrogen | N |
| | Potassium | K |
| | Calcium | Ca |
| | Magnesium | Mg |
| | Phosphorus | P |
| | Sulfur | S |

TABLE 1B

Example micronutrients in plants. (Havlin, et al. 2014)

| Classification | Nutrient | |
|---|---|---|
| | Name | Symbol |
| Micronutrients | Chlorine | Cl |
| | Iron | Fe |
| | Boron | B |
| | Manganese | Mn |
| | Zinc | Zn |
| | Copper | Cu |
| | Molybdenum | Mo |

Macronutrients and/or micronutrients in herbicide compositions, methods, and kits of embodiments herein can be provided as elemental macronutrients and/or micronutrients, and/or in compounds. Examples of suitable macronutrient compounds suitable for herbicides and kits of some embodiments herein include the compounds shown in Tables 2A-2F. Examples of suitable micronutrient compounds suitable for herbicides and kits of some embodiments herein include the compounds shown in Tables 2G-2N. In some embodiments, a macronutrient comprises, consists of, or consists essentially of H, C, O, N, K, Ca, Mg, P, S, or a combination of the listed items. In some embodiments, a macronutrient comprises, consists of, or consists essentially of H, C, O, N, K, or a combination of the listed items. In some embodiments, a macronutrient comprises, consists of, or consists essentially of H, C, O, N, K, Ca, P, S, or a combination of the listed items. In some embodiments, a macronutrient comprises, consists of, or consists essentially of H, C, O, N, K, Ca, P, S, or a combination of the listed items. In some embodiments, a macronutrient comprises, consists of, or consists essentially of N, K, P, S, or a combination of the listed items. In some embodiments, a micronutrient comprises, consists of, or consists essentially of Cl, Fe, B, Mn, Zn, Cu, Mo, or a combination of the listed items. In some embodiments, a micronutrient comprises, consists of, or consists essentially of Cl, Fe, B or a combination of the listed items. In some embodiments, a micronutrient comprises, consists of, or consists essentially of Cl, Fe, B, Mn, Cu, Mo, or a combination of the listed items. In some embodiments, a micronutrient comprises, consists of, or consists essentially of B, Mn, Zn, Cu, Mo, or a combination of the listed items. In some embodiments, the micronutrient does not comprise Fe, for example chelated iron. As such, the herbicide does not comprise iron, or does not comprise chelated iron in particular.

In some embodiments, the macronutrient is the active herbicidal agent of the herbicide, method or kit. Such herbicidal compositions may include an inactive adjuvant mixture, and have a pH of about 4 to about 7, preferably pH 4.5 to pH 5.5. The herbicide can comprise a mineral and/or organic acid, which can adjust the pH to a suitable value or range as described herein, but such acids are generally not considered an active ingredient, unless the acid is present in concentrations and quantities suitable to function as a burn-down component as described herein. That is, the adjuvant also is not considered an active ingredient. Such macronutrient-containing herbicidal compositions are suitable for all herbicidal uses including crops, ornamental vegetation, rights-of-way, roadsides, and the like. In some embodiments, the macronutrient comprises a macronutrient shown in Table 1A, or a combination of two or more of the macronutrients shown in Table 1A. The macronutrient(s) can be in the form of elemental macronutrients, and/or compounds, for example compounds shown in Tables 2A-2F.

In some embodiments, the micronutrient is the active herbicidal agent of the herbicide, method or kit. Such herbicides may include an inactive adjuvant mixture, and have a pH of about 4 to about 7, preferably pH 4.5 to pH 5.5. The herbicide can comprise a mineral and/or organic acid, which can be useful for pH adjustment, but is not considered an active ingredient, unless the acid is present in concentrations and quantities suitable to function as a burn-down component as described herein. The adjuvant also is not considered an active ingredient. Without being limited by any theory, it is contemplated that small quantities of micronutrient can adversely affect desired plants, for example in run-off. Accordingly, it is contemplated that in some embodiments, such micronutrient-containing herbicidal compositions are suitable for rights-of-way, roadsides, and other arrangements in which crops or ornamental vegetation will not be exposed, or will be minimally exposed to the herbicide. In some embodiments, the micronutrient comprises a micronutrient shown in Table 1B, or a combination of two or more of the micronutrients shown in Table 1B. The micronutrient(s) can be in the form of elemental micronutrients, and/or compounds, for example compounds shown in Tables 2G-2N. In some embodiments, the micronutrient comprises a compound shown in Tables 2G-2N that is not Fe.

In some embodiments, both a macronutrient and a micronutrient are active ingredients of the herbicide, method, or kit. Such herbicides may include an inactive adjuvant mixture, and have a pH of about 4 to about 7, preferably pH 4.5 to pH 5.5. In some embodiments, the pH range is about 4 to about 6.5, or about 4 to about 6, or about 4 to about 5.5, or about 4 to about 5, or about 4.5 to about 7, or about 4.5 to about 6.5, or about 4.5 to about 6, or about 4.5 to about 5.5, or about 4.5 to about 5, or about 5 to about 7, or 0.5 to about 6.5, or about 5 to about 6, or about 5 to about 5.5, or about 6 to about 7. The herbicide can comprise a mineral and/or organic acid, which can be useful for pH adjustment, but is not considered an active ingredient. The adjuvant also is not considered an active ingredient plus an inactive adjuvant mixture. Since such a composition comprises a micronutrient active ingredient, for reasons noted above, without being limited by any theory, it is contemplated that such micronutrient-containing herbicidal compositions are suitable for rights-of-way, roadsides, and other arrangements in which crops or ornamental vegetation will not be exposed, or will be minimally exposed to the herbicide. In some embodiments, the macronutrient comprises a macronutrient shown in Table 1A, or a combination of two or more of the macronutrients shown in Table 1A, and the micronutrient comprises a micronutrient shown in Table 1B, or a combination of two or more of the micronutrients shown in Table 1B. The macronutrient(s) can be in the form of elemental macronutrients, and/or compounds, for example compounds shown in Tables 2A-2F. The micronutrient(s) can be in the form of elemental micronutrients, and/or compounds, for example compounds shown in Tables 2G-2N. In some embodiments, the micronutrient comprises a compound shown in Tables 2G-2N that is not Fe.

In some embodiments, the acid as an inactive component of the herbicide comprises, consists of, or consists essentially of an organic acid or a mineral acid. In some embodiments, the acid of the herbicide comprises, consists of, or consists essentially of a mineral acid. In some embodiments, the acid of the herbicide comprises, consists of, or consists essentially of an organic acid. Additionally, in some embodiments, other pH adjusting agents may be included in the herbicide for the purpose of adjusting the pH to the indicated range, for example acids such as HCl, and/or bases such as NaOH. These pH adjusting agents are not considered active ingredients. As such, it is contemplated that in some embodiments, an acid, or other pH-adjusting agent (e.g. a base) can be present in the herbicide, and is an inactive ingredient of the herbicide.

Kits comprising ingredients for constituting an herbicide as described herein, for example by contacting components of the kit with a suitable quantity of water are also contemplated in some embodiments. In some embodiments, kits comprise the organic acid, at least one nutrient (macronutrient and/or micronutrient), and an adjuvant. These items of the kits can be dissolved and/or diluted in aqueous solvent, such as water (e.g., tap, pond, well, or the like). The items of the kit can be in unit quantities, so that the unit quantities can readily be dissolved and/or diluted in aqueous solvent to yield an herbicide having the molar ratios of nutrient and pH range described herein. In some embodiments, the nutrient or nutrients are the primary active ingredient of the herbicide. In some embodiments, the macronutrient of the kit comprises a macronutrient shown in Table 1A, or a combination of two or more of the macronutrients shown in Table 1A. In some embodiments, the micronutrient of the kit comprises a micronutrient shown in Table 1B, or a combination of two or more of the micronutrients shown in Table 1B. The macronutrient(s) can be in the form of elemental macronutrients, and/or compounds, for example compounds shown in Tables 2A-2F. The micronutrient(s) can be in the form of elemental micronutrients, and/or compounds, for example compounds shown in Tables 2G-2N. In some embodiments, the micronutrient comprises a compound shown in Tables 2G-2N that is not Fe.

In some embodiments, the herbicide comprises or a combination of two or more of the listed nutrients, for example a K compound and a P compound, a K compound and an N compound, a K compound and a Mg compound, a K compound and a S compound, a K compound and a micronutrient, a P compound and an N compound, a P compound and a Mg compound, a P compound and a S compound a P compound and a micronutrient, a S compound and a Mg compound, a S compound and a micronutrient, or a Mg compound and a micronutrient. It is contemplated that suitable K, P, N, S, and Mg compounds can comprise any agriculturally acceptable compounds containing any of K, P, N, S, and Mg. Any agriculturally-acceptable, water-soluble compound can be a suitable source of the nutrient(s) in some embodiments. For example, salts of K, P, Mg, S, and/or N-containing ions can comprise suitable sources of these nutrients in some embodiments. Furthermore, in some embodiments, for the indicated K, P, Mg, S, and/or N-containing ions, the partner anion (or cation) does not comprise a conventional agricultural fertilizer. As such, it is contemplated that in some embodiments, the K compound does not comprise a cation that is a conventional agricultural fertilizer. It is noted that while it can be possible for a "fertilizer" to contain one or more nutrients, the term "fertilizer" is not necessarily interchangeable with "nutrient." For example a commercial fertilizer product may contain a particular macro- or micro-nutrient ion itself, and/or may also contain other substances. Accordingly, application of a dissolved fertilizer does not necessarily teach the application or absorption of an excess of any nutrient. Furthermore, it is contemplated that simply applying dissolved fertilizer products to plants (which, as noted above, can contain substances other than nutrients) can have undesirable toxic effects on soil and water.

The herbicide can have active ingredient of a specific nutrient or combination of nutrients (e.g., a nutrient salt of a nutrient described herein), which can be dissolved in aqueous solution comprising an organic acid at a concentration that achieves an acidity suitable for foliar absorption. Such an acidity can be a pH of about 4 to 7, preferably 4.5 to 7.0, more preferably 4.5 to 5.5. For example, in some embodiments, the herbicide comprises an aqueous formulation having a pH of about 3.5, 4, 4.5, 5, 5.5, 6, 6.5, or 7, including ranges between any two of the listed values. Without being limited by theory, this suitable pH for absorption also minimizes the chemical destruction ("burning") of the plant surface tissues resulting from high alkalinity (high pH) typical of concentrated solutions of nutrient salts. This condition extends the period of time available for absorption of a specific nutrient by leaves and other surface tissues. In some embodiments, the herbicide is configured to have a pH suitable for absorption of the nutrient or nutrients, and further comprises a burn-down component configured to cause destruction of plant tissue after the nutrients or nutrients have been absorbed throughout the plant, for example in the roots. In some embodiments, the burn-down component is part of a single herbicide composition. In some embodiments, the burn-down component is configured for application after absorption of the nutrient or nutrients.

Deliquescence

Absorption of any substance through the layers of the cuticle only occurs from an aqueous solution, while dry nutrients remain unabsorbed (Wojcik, 2004, which is hereby incorporated by reference in its entirety). Accordingly, after a foliar material dries from evaporation on the plant, that sprayed fertilizer or herbicide remains unabsorbed until it is removed by wind, rain or irrigation spray. However, all dry nutrient salts are "hygroscopic" in that they absorb atmospheric water. Some nutrient salts are hygroscopic to the extent that they attain a semi-liquid state simply as a result of being in normally humid air, a condition referred to as "deliquescence". (Shafer and Reed, 1986). The minimal relative humidity at which this re-liquefaction occurs is referred to as the "point of deliquescence" (POD) of the material. Formulations in accordance with some embodiments comprise nutrient salts that are each deliquescent at low relative humidity. Without being limited by theory, when appropriately formulated, deliquescence can also maintain the soluble organic acid component in a liquid state as well in some embodiments. In some embodiments, the herbicide comprises, consists essentially of, or consists of a deliquescent formulation. In some embodiments, following application of the deliquescent formulation on plant surface tissues, for example by spray, the formulation remains in a semi-liquid state for an extended period, typically over several days. And although the material may dry out in the heat of the day following initial spray application, when the humidity attains the modest relative humidity for deliquescence, the active components re-liquefy and absorption into the leaf resumes. Commonly this re-dissolution occurs during the evening, night and early morning, but also can occur during the day if sufficiently humid conditions exist. In some embodiments, the adjuvant mixture may include a "humectant", a category of substances employed to keep things or surfaces moist and thus extend the semi-liquid state necessary for absorption of the active ingredient through the plant surfaces. Examples of potentially suitable humectants include but are not limited to glycerol, sugar, honey, sugar alcohols, and polyethylene glycol. In some embodiments, the humectant comprises, consists essentially of, or consists of a carbohydrate.

Furthermore, as a result of evaporation, the molar concentrations of the active ingredients in the applied formulation will gradually increase. Eventually, the elevated concentration of the nutrient salts and organic acids reach a point where chemical "burning" of the surface tissue will destroy the cuticular layer. This can kill the above-ground absorbing tissue in a similar manner as is caused by conventional "burn-down" herbicides. Accordingly, in some embodiments, absorption of the herbicide persists long enough to allow toxic amounts of nutrient to enter and be translocated throughout the plant and achieve the level sufficient for nutrient disruption before the cuticular layer is damaged to the point it can no longer absorb nutrient. If killed too early, the desired systematic effect of the elevated nutrient will not be achieved and the plant can regenerate from the undamaged tissue below ground. It has been discovered herein that a duration of about 72 hours provides conditions favorable for nutrient absorption sufficient to achieve desired herbicidal results. By formulating the "point of deliquescence" (POD), the absorption rate of the herbicide can be tuned in accordance with some embodiments. Preferably, in some embodiments specific formulations of nutrient salts possessing an appropriately low POD are used, thus allowing the applied formulation to remain in a semi-liquid state on plant surfaces for an extended period, and also resulting in redissolution if evaporation occurs during the day. Accordingly, by formulating the nutrient composition with a low POD, the formulation is retained on the plant surface for 1-5 days, preferably, 2-4 days and most preferably about 72 hours. In some embodiments, the herbicide is formulated to be absorbed for about 3 days. In some embodiments, the herbicide is formulated to be absorbed for about for about 1, 2, 3, 4, or 5 days, including ranges between any two of the listed values, for example about 1-3, 1-4, 1-5, 2-3, 2-4, 2-5, 3-4, 3-5 days.

Nutrient Phtotoxicity

Without being limited by theory, the use of appropriate adjuvants to create a thorough coating of plant surfaces with the herbicidal composition, and to further enhance foliar absorption, creates physical and chemical conditions on the surface tissues of the treated plants that increase the uptake of the nutrient resulting in toxic levels of nutrient sufficient to cause plant death from a process termed "nutrient pytotoxicity". The adjuvants may also include a nitrogen source to further enhance foliar uptake. These nitrogen sources can include but not necessarily be limited to the common commercial fertilizers urea, urea+ammonium nitrate (UAN), ammonium polyphosphate, or ammonium sulfate. (Hager and McGlamery, 1997, which is hereby incorporated by reference in its entirety) Simply put, nutrient phytotoxicity in plants is analogous to the poisoning and death of an animal that can result from the consumption by an animal of excess amounts of a vitamin (for example poisoning from vitamins A, B, or D in humans), or even of a food (death from 1000 marshmallows). In plants a physiologically active mineral required only in small amounts may become toxic or fatal in excess (chlorine and selenium in plants).

Nutrient Content

All nutrients are by definition necessary for the optimal growth and development of a plant, and all nutrients once absorbed and under suitable growth conditions will be distributed appropriately within the plant. The amount of a specific nutrient required for a plant can be relatively large ("macro-nutrients") or minute ("micro-nutrients"). Furthermore, the amounts of each different nutrient can vary from tissue-to-tissue, and throughout the growing season. Without being limited by theory, nutrient disruption within a plant could conceivably result from the excessive absorption of any macro- or micro-nutrient, alone or in combinations. The concept of nutrient disruption as describing toxic infusion of any and all plant nutrients is contemplated in accordance with embodiments herein.

Herbicides of some embodiments herein use a foliar-applied nutrient infusion to create toxic internal concentrations of what are normally life-sustaining nutrient chemicals, for example potassium, nitrogen, phosphorus, sulfur, or magnesium. In some embodiments, the herbicide comprises a macro-nutrient. In some embodiments, the herbicide comprises a micro-nutrient. In some embodiments, the herbicide comprises a macro-nutrient and a micro-nutrient. In some embodiments, the herbicide comprises at least one of potassium, nitrogen, phosphorus, sulfur, magnesium, or a combination of two or more of these, for example, potassium and nitrogen, potassium and phosphorus, potassium and sulfur, potassium and magnesium, or even a combination of potassium and nitrogen and phosphorus and sulfur and magnesium.

Without being limited by theory, it is contemplated that a nutrient content sufficiently high to disrupt metabolism when applied to foliar tissues and absorbed by plants as described herein, is well above nutrient contents of conventional foliar fertilizers in some embodiments herein. In some embodiments, the nutrient content of the herbicide is an order of magnitude above that of a conventional foliar fertilizer. By way of example, a conventional foliar fertilizer may have a nutrient content of about 2%, and the herbicide of some embodiments may have a nutrient content of about 20%. In some embodiments, an herbicide has a nutrient molarity in the order of magnitude of 1 to 2.5 M. An herbicide of some embodiments has a concentration of a nutrient (e.g., $K^+$, $Mg^{2+}$, $Ca^{2+}$, nitrogen, phosphorous, sulfur, or a combination of two or more of these) of about 1.0 M to about 2.5 M. In some embodiments, the nutrient concentration in the herbicide is about 0.5M, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5M, including ranges between any two of the listed values, for example 0.5-2.5M, 0.8-2.2M, 0.9-2.1 M, 1.0-1.8M, 1.0-2.0 M, 1.2-1.8 M, 1.2-2,0 M, and the like. Thus, the herbicides in some embodiments contain several orders of magnitude more nutrient than is contained in foliar fertilizers. For example, in some embodiments, in which the nutrient comprises potassium, the herbicide contains several orders of magnitude more $K^+$ than is contained in foliar K fertilizers. However, if conventional foliar K fertilizer was intended for use as an herbicide and applied at the high molarity of these embodiments, all sprayed plant tissue above the ground would be burned chemically within hours preventing the absorption of sufficient $K^+$ to function as a systemic herbicide, It is the ability of the invention to induce the absorption or high levels of certain nutrients including $K^+$ with delayed chemical burning of plant tissue that differentiates the invention form commercial foliar fertilizer formulations, as well as from conventional burn-down herbicides.

The macro-nutrient potassium (K) was chosen for initial experimentation (see. e.g., Examples 2-7, herein). Potassium (K) has a number of properties that are amenable to being a component of an herbicide in accordance with embodiments herein. Without being limited by theory, reasons include:

1. K is considered a "macronutrient" and is required for a plant's survival. K differs from most other plant nutrients in that it is not a component of chemical compounds in plants. (Havlin et al., 2014, which is hereby incorporated by reference in its entirety) It is typically found only in the form of the $K^+$ ion in solution or bound to negative charges on the surface of various tissues. Consequently, the effects of $K^+$ can be related to ionic strength in plant cells. In this role K is substantially involved in many physiological processes critical to the growth, development and reproduction of all plants. (Taiz et al., 2015)

2. $K^+$ is highly mobile throughout a plant as a consequence of its cationic state, but also as a consequence of the small diameter of $K^+$ relative to other nutrient ions and molecules. (Abou El-Nous, 2002; Borowski and Michalek, 2009; Bukovac and Wittwer, 1957; Christensen, 2005; Marschner, 1995; Mengel, 2002; Wojcik, 2004, each of which is hereby incorporated by reference in its entirety) Following absorption by either roots, or in the case of foliar application by surface tissues, $K^+$ moves rapidly throughout the entire the plant, as well as within individual cells (Marschner, 1986, which is hereby incorporated by reference in its entirety).

3. $K^+$ plays an important role in the efficient absorption of water and dissolved nutrients into roots, and their translocation from roots to the above-ground portions of the plant. $K^+$ is essential for photosynthesis as a result of several functions that include the transfer of radiant energy to chemical energy, production and activity of photosynthetic enzymes, and the maintenance of electroneutrahty during the production of ATP in chloroplasts. (Taiz et al., 2015)

4. $K^+$ is substantially involved in the functioning of over 40 plant enzymes including many involved in energy utilization, respiration, nitrogen metabolism, and the synthesis of starch. After carbon dioxide ($CO_2$) is converted to sugars during photosynthesis, the sugars are translocated to roots, fruits, grains, and tubers using ATP that requires $K^+$ for its synthesis. $K^+$ also is critical for optimal flow of sap and water in both the phloem and xylem. (Havlin et al., 2014; Marschner, 1986; Taiz et al., 2015, each of which is hereby incorporated by reference in its entirety).

5. At the leaf surface, $K^+$ regulates the opening and closing of stomate pores regulating the exchange of oxygen and carbon dioxide with the atmosphere, and regulates the transfer of water from the plant to the atmosphere ("transpiration"). (Taiz et al., 2015) Transpiration creates the force drawing up and distributing water and dissolved nutrients required by the living plant. However, without being limited by theory, excess K in leaves appears to induce turgidity in stomatal guard cells, prolonged stomatal opening, and excessive water loss from uncontrolled transpiration. This in turn leads to a systemic loss of the internal turgor pressure (wilting) required to maintain the plant's upright and functional form. Severe wilting results in irreversible mechanical damage to cells, cessation of normal cell function, complete collapse of the plant, and death. (Taiz, et al., 2015) The role of excess K in this destructive progression has been demonstrated experimentally reported in this application and is contemplated to be useful in herbicide compositions, methods, and kits of various embodiments herein.

Without being limited by theory, mechanisms have been proposed for the manner by which prolonged excess $K^+$ in guard cells is achieved, but this phenomenon is still being studied. For example, it may result from excess $K^+$ ion outside the guard cell's plasma membrane to the extent it interferes with $K^+$ efflux from guard cells required for stomatal closure and control of water loss from the leaf. (Taiz, ibid.)

Without being limited by theory, the high mobility of throughout the plant, together with the high number of chemical, enzymatic, and electrochemical functions for which this nutrient is required for plant metabolism, makes potassium well-suited for functioning in nutrient phytotoxicity in accordance with some embodiments. Loss of turgor pressure is a direct consequence of intentionally induced K toxicity. However, under normal growing conditions direct K toxicity does not often occur. Rather, deleterious effects on plant growth and development are a consequence of inhibition of nutrient uptake by the roots caused by a cation imbalance caused by excess K. This can lead to multiple nutrient deficiencies, most commonly that of nitrogen, but also of magnesium, manganese, and calcium. (McCauley, et al., 2017; Nicholson, 2017, each of which is hereby incorporated by reference in its entirety) This said, to the best of Applicant's knowledge, there is little research or published date related to excessively high levels of K or other nutrients deliberately induced for herbicidal action. Experiments reported in this Application provide evidence supporting toxicity and death of plants as a consequence of high tissue K. Absorption of an amount of K+ sufficiently in excess of that optimal for plant growth and development can kill the entire plant in some embodiments.

K also possesses a number of salutary characteristics not directly related to its physiological role in plants and which further recommended its use in some embodiments herein.

1. Many of the sources of K available are of low toxicity and "Generally Recognized as Safe" (GRAS) to humans by the U.S. Food and Drug Administration. The active ingredients suitable for some embodiments herein are believed to be minimally harmful to the environment when formulated and applied as recommended. Consequently, it is anticipated that a number of herbicide formulations according to embodiments herein will qualify for OMRI (Organic Materials Review Institute) registration and use in organic growing operations.

2. The effects of $K^+$ in the soil and in surface and ground waters are expected to be benign. K is typically bound in soil clay particles in the upper few centimeters of soil, and undergoes limited migration in the soil compared to other nutrients and thus has less potential to reach ground and surface waters. (Havlin et al., 2014; Kurtural, et al., undated; Mengel, 1985, each of which is hereby incorporated by reference in its entirety), Munson and Werner (1963) state that on silt loam or finer textured soils of the west and midwest, leaching of K "will be practically nil."

3. In aquatic and marine systems K is generally present already in sufficient quantities necessary for aquatic life, and is thus not commonly a "limiting nutrient" the addition of which can trigger eutrophication (excessive growth and propagation of aquatic organisms) held back only by the absence of a critical nutrient. (Elser, et al. 2007; Anon., 2016, each of which is hereby incorporated by reference in its entirety). In the event that effective concentrations and/or quantities herbicides of some embodiments do reach surface waters, either by accident or resulting from runoff of K not bound in the surface soils, K is less likely than other macronutrients to promote eutrophication.

4. Herbicides comprising a nutrient, in accordance with some embodiments are less likely to be harmful to non-target plants than conventional herbicides. In some embodiments, effectiveness depends on the application to targeted weeds of a toxic concentration of the herbicide nutrient according to embodiments herein. Below this concentration, as is likely to be the concentration of drift nutrient redeposition, the material is not effective as an herbicide, and as a consequence is less likely to seriously damage non-target plants.

5. Although active ingredients are plant nutrients applied to target weeds at herbicidal concentrations, the amount of the nutrient applied per acre constitutes a small percentage of that nutrient normally applied in a program of maintenance or remedial fertilization, and unlikely to interfere with the goals of a fertilization regimen. However, if desired, the nutrient contribution of the herbicide can be formulated to supplement a small portion of a crop's fertilization requirement for a specific stage of growth and development.

Effective K based nutrient disruptive herbicides theoretically can be prepared from many K-salt and organic acid formulations and these are included under this patent application. Owing to differences among these active components including solubility, hygroscopicity, deliquescence, percentage of K in the salt, and molar mass, certain formulations will be better suited for use as a foliar herbicide. Examples of multiple formulations potentially well suited for use as a nutrient disruptive K herbicide and that are based on the K salts formate, lactate, and acetate are included in this application as examples from among the many potentially suitable nutrient compounds. See Reaction Equations below.

Prepared as an aqueous solution, in some embodiments, the herbicide is applied topically as a spray, typically with an acidity of between pH 4 and pH 7 for the foliar absorption of the K formulations initially used to test and illustrate the effectiveness of herbicides contemplated herein. The acidity selected for a specific herbicidal nutrient formulation is another significant characteristic of herbicides in this Application according to some embodiments, in that the suitable acidity reduces and delays chemical burning of plant tissue resulting from either excessively high alkalinity (high pH), or from excessively high acidity (low pH). These moderate levels of acidity and alkalinity also increase the safety of the herbicide to its users, being typical of the juice acidity of many fresh fruits and vegetables including apples, bananas, cauliflower, cucumbers, cherries, figs and string beans. (USDA, 2007).

Reaction Equations

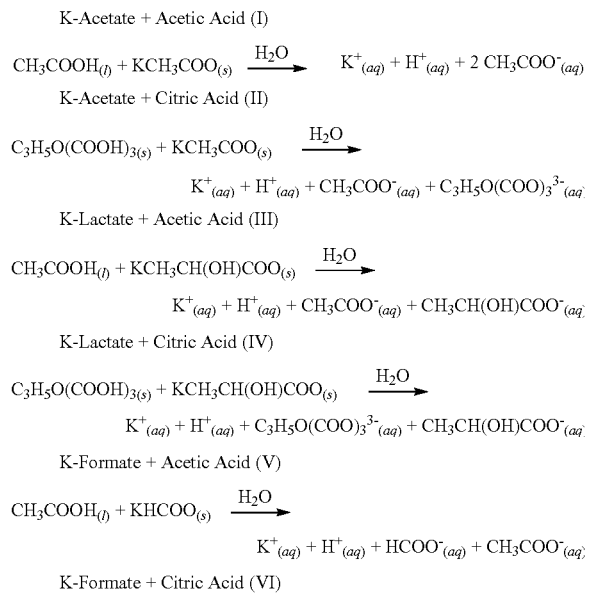

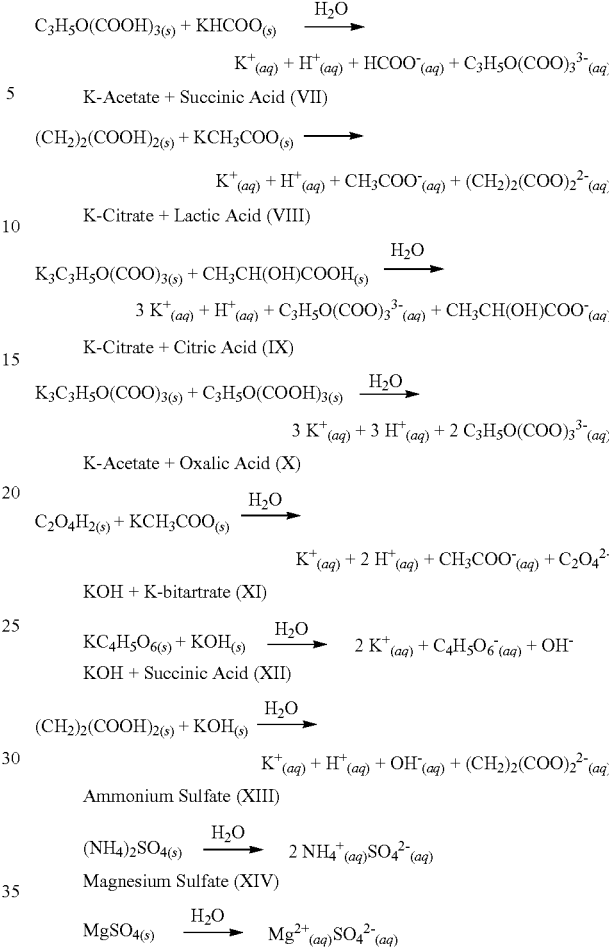

Other K+ compounds suitable in some embodiments include those listed in, though not necessarily limited to, Table 2A, including combinations of any two or more of the compounds in Table 2A. At this time their suitability for the herbicide according to some embodiments, including solubility, molecular weight, deliquescence, safety during handling, stability during storage, and other physical and chemical characteristics has not been fully investigated or tested experimentally. Accordingly, in some embodiments, the herbicide comprises a potassium compound of Table 2A, and thus comprise potassium as the only nutrient. In some embodiments, the herbicide comprises a combination of two or more potassium compounds of Table 2A (Havlin, et al., 2014). Shafer and Reed, 1986 identify potassium sorbate as an example of a potassium compound.

Additional agriculturally acceptable water-soluble K compounds are also contemplated to be suitable K compounds in accordance with some embodiments herein. Table 2A. Additionally, agriculturally acceptable water-soluble compounds containing N, P, S, Mg, and/or micronutrients or trace elements are also contemplated as acceptable sources of nutrients for herbicides in accordance with some embodiments. Tables 2B-2N. in some embodiments, the herbicide, method, or kit comprises a nutrient selected from any of Tables 2A-2N, or two or more of the listed tables (for example, all of Tables 2A-2N). In some embodiments, one or more compounds of Table 2A-2N is solubilized in aqueous solution in an herbicide, method, or kit as described herein. Without being limited by theory, it is noted that the solubility of some of the noted compounds is affected by the pH of the aqueous solution, so that the compound may have a greater solubility at an acidic pH than at a pH of about 7. In some embodiments, an aqueous solution of an herbicide, method, or a kit comprises a solubilizing agent or carrier, for example an amphiphilic molecule (e.g., a detergent) to facilitate the inclusion of one or more compounds of Table 2A-2N in the aqueous solution.

TABLE 2A

Examples of potassium (K) compounds potentially suitable for the herbicide of some embodiments.
Potassium compound K-bicarbonate: $KHCO_3$
K-carbonate: $K_2CO_3$
K-chloride: KCl
K-hydroxide: KOH
K-magnesium sulfate: $K_2SO_4$, $MgSO_4$
K-nitrate: $KNO_3$
K-phosphates: $KRH_2PO_4$, $K_2HPO_4$, $K_3PO_4$, $K_2HPO_4$
K-sulfate: $K_2SO_4$
K-tartrate: $K_2C_4H_4O_6$
K-thiosulfate: $K_2S_2O_3$
K-malate: $K_2(C_2H_4O(COO)_2)$
K-benzoate: $C_7H_5KO_2$
K-polysulfide: $KS_x$

TABLE 2B

Examples of the macronutrient phosphorus (P) compounds potentially suitable for the herbicidal compositions.
Phosphorus compound Superphosphates: $Ca(H_2PO_4)_2$
Monoammonium phosphate: $NH_4H_2PO_4$
Diammonium phosphate: $(NH_4)2 \cdot HPO_4$
Ammonium polyphosphate: $(NH_4)_3PO_4$
Urea ammonium phosphate: $(NH_4)_3HP_2O_7 \cdot NH_4H_2PO_4$
Monopotassium phosphate: $KH_2PO_4$
Dipotassium phosphate: $K_2HPO_4$

TABLE 2C

Examples of the macronutrient nitrogen (N) compounds potentially suitable for the herbicidal compositions.
Nitrogen compound Anhydrous ammonia: $NH_3$
N solutions
Ammonium bicarbonate: $NH_5CO_3$
Ammonium chloride: $NH_4Cl$
Ammonium nitrate: $NH_4NO_3$
Ammonium sulfate: $(NH_4)_2SO_4$
Ammonium thiosulfate: $H_8N_2O_3S_2$
Calcium ammonium nitrate: multiple formulations
Ammonium thiosulfate: $H_8N_2O_3S_2$
Ammonium polyphosphate: $(NH_4)_3PO_4$
Diammonium phosphate:$(NH_4)_2HPO_4$
Monoammonium phosphate: $H_4H_2PO_4$
Urea: $CH_4N_2O$
Urea-ammonium nitrate
Urea-ammonium phosphate
Urea phosphate: $CO(NH_2)_2 \cdot H_3PO_4$
Urea-sulfate: $C_2H_{10}N_4O_6S$
Calcium nitrate: $Ca(NO_3)_2$
Potassium nitrate: $KNO_3$
Sodium nitrate: $NaNO_3$

TABLE 2D

Examples of the macronutrient magnesium (Mg) compounds potentially suitable for the herbicidal compositions.
Magnesium Compound Magnesium sulfate (Epsom salt): $MgSO_4 \cdot 7H_2O$
Langbenite: $K_2SO_4 \cdot 2MgSO_4$
Magnesium chloride: $MgCl_2$
Magnesium nitrate: $Mg(NO_3)_2$
Dolomite: $MgCO_3 \cdot CaCO_3$
Dolomitic limestone: $MgCO_3 \cdot CaCO_3$
Magnesium oxide: MgO
Kieserite: $MgSO_4 \cdot H_2O$
Kainite: $M_2SO_4 \cdot KCl - 3H_2O$
Struvite: $MgNO_4PO_4 \cdot 6H_2O$
K-magnesium sulfate: $K_2SO_4$, $MgSO_4$

TABLE 2E

Examples of the macronutrient calcium (Ca) compounds potentially suitable for the herbicidal compositions.
Calcium compound Calcium carbonate: $CaCO_3$
Dolomite: $MgCO_3 \cdot CaCO_3$
Gypsum: $CaSO_4 \cdot 2H_2O$
Superphosphates: $Ca(H_2PO_4)_2$
Calcium ammonium nitrate: $5Ca(NO_3)_2 \cdot NH_4NO_3$

TABLE 2F

Examples of the macronutrient sulfur (S) compounds potentially suitable for the herbicidal compositions.
Sulfur compound Ammonium polysulfide: $NH_4S_4$
Ammonium sulfate: $(NH_4)_2SO_4$
Ammonium thiosulfate: $H_8N_2O_3S_2$
Calcium polysulfide: $CaS_x$
Ammonium thiosulfate: $H_8N_2O_3S_2$
Ferrous sulfate: $FeSO_4 \cdot H_2O$
Gypsum: $CaSO_4 - 2H_2O$
Magnesium sulfate (Epsom salt): $MgSO_4 \cdot 7H_2O$
K-polysulfide: $KS_x$
K-sulfate: $K_2SO_4$
K-thiosulfate ($K_2S_2O_3$).
Elemental sulfur: $S^0$
Sulfuric acid: $H_2SO_4$
Urea-sulfur: $CO(NH_2)_2 + S$
Urea-sulfuric acid: $CO(NH_2)_2 + H_2SO_4$
Zn sulfate: $ZnSO_4 \cdot H_2O$

TABLE 2G

Examples of the micronutrient iron (Fe) compounds potentially suitable for the herbicidal compositions.
Iron compound Ferrous sulfate: $FeSO_4 \cdot 7H_2O$
Ferric sulfate: $Fe_2(SO_4)_3 \cdot 4H_2O$
Ferrous oxide: FeO
Ferric oxide: $Fe_2O_3$
Ferrous ammonium phosphate: $Fe(NH_4)PO_4 \cdot H_2O$
Ferrous ammonium sulfate: $(NH_4)_2SO4 \cdot FeSO_4 - 6H_2O$
Iron ammonium polyphosphate: $Fe(NH_4)HP_2O_7$

TABLE 2H

Examples of the micronutrient zinc (Zn) compounds potentially suitable for the herbicidal compositions.

Zinc compound

Zn sulfate monohydrate: $ZnSO_4 \cdot H_2O$
Zn oxide: $ZnO$
Zn carbonate: $ZnCO_3$
Zn phosphate: $Zn3(PO_4)_2$
Zn chelates: $Na_2Zn$ EDTA
Zn lignosulfonate
Zn polyflavanoid

TABLE 2I

Examples of the micronutrient copper (Cu) compounds potentially suitable for the herbicidal compositions.

Copper compound

Cu sulfate: $CuSO_4 \cdot 5H_2O$
Cu sulfate monohydrate: $CuSO_4 \cdot H_2O$
Cu acetate: $Cu(CuH_2O_2)_2 \cdot H_2O$
Cu ammonium phosphate: $Cu(NH_4)PO_4 \cdot H_2O$
Copper chelates: $Na_2Cu$ EDTA

TABLE 2J

Examples of the micronutrient manganese (Mn) compounds potentially suitable for the herbicidal compositions.

Manganese compound

Mn sulfate: $MnSO_4 \cdot 4H_2O$
Mn oxide: $MnO$
Mn chloride: $MnCl_2$
Mn chelates: $Na_2Mn$ EDTA
Mn lignosulfonate
Mn polyflavanoid

TABLE 2K

Examples of the micronutrient boron (B) compounds potentially suitable for the herbicidal compositions.

Borax compound

Borax: $Na_2B_4O_7 \cdot 10\ H_2O$
Boric acid: $H_2BO_3$
Colemanite: $Ca_2B_6O_{11} \cdot 5H_2O$
Sodium pentaborate: $Na_2B_{10}O_{16} \cdot 10H_2O$
Sodium tetraborate: $Na_2B_4O_7 \cdot 5H_2O$
Sodium octaborate: $Na_2B_8O_{13} \cdot 4H_2O$

TABLE 2L

Examples of the micronutrient chlorine (Cl) compounds potentially suitable for the herbicidal compositions.

Chlorine compound

Ammonium chloride: $NH_4Cl$
Calcium chloride: $CaCl_2$
Magnesium chloride: $MgCl_2$
Potassium chloride: $KCl$
Sodium chloride: $NaCl$

TABLE 2M

Examples of the micronutrient molybdenum (Mo) compounds potentially suitable for the herbicidal compositions.

Molybdenum compound

Ammonium molybdate: $(NH_4)_6Mo_7O_{24} \cdot 2H_2O$
Sodium molybdate: $Na_2MoO_4 \cdot 2H_2O$
Molybdenum trioxide: $MoO_3$
Mo frits: Mo silicates

TABLE 2N

Examples of other micronutrient potentially suitable for the herbicidal compositions.

Nickel (Ni)
Cobalt (Co)
Silicon (Si)
Selenium: (Se)
Vanadium: (V)

Acidity and Acids

It is contemplated that a pH of about 4 to about 7 is amendable to absorption of the herbicide without acute "burn-down" effects that could otherwise kill the plant before the herbicide is absorbed. In some embodiments, a pH is achieved with a suitable amount of one or more organic acids and/or mineral acids. For example, it is contemplated that to minimize or delay "burn-down" effects, any of a number of weak organic acids and/or mineral acids would be present in quantities sufficient to achieve optimal acidities in the herbicide solution.

The acidity in some embodiments is maintained within the desired range using an acid, for example a mineral acid or an organic donator such as, but not necessarily limited to, formic, acetic, malic, tartaric, lactic or citric acid. Of the organic acids suitable for the herbicide in some embodiments, citric acid is a preferred choice owing to its availability as a dry crystalline solid of high solubility; expected benign environmental effects when sprayed upon exposed soil and upon release to the environment from decaying plant tissue; low cost; and its availability in an "organic" form or as a major component of lemon juice. Acetic acid is another suitable organic acid for similar reasons.

Organic acids potentially suitable for and included in the herbicide for the purpose of adjusting acidity' according to some embodiments are those listed in, but not necessarily limited to, Table 3. At this time the suitability, including solubility, molecular weight, deliquescence, safety during handling, stability during storage, and other physical and chemical characteristics have not been fully investigated experimentally for all potentially suitable organic acids. According, in some embodiments, the herbicide comprises an organic acid of Table 3, or a combination of two or more organic acids of Table 3.

TABLE 3

Organic acids potentially suitable to adjust the acidity of herbicides of some embodiments Acetic acid (ethanoic) ($CH_3COOH$)
Benzoic (Benzenecarboxylic acid ($C_6H_5COOH$)
Butyric (butanoic) acid ($CH_3CH_2CH_2COOH$).
Caproic (hexanoic) acid ($CH_3CH_2CH_2CH_2CH_2COOH$).
Capric (decanoic) acid: $C_{10}H_{20}O_2$
Carbonic (hydroxymethanoic) acid ($H_2CO_3$)
Citric acid ($C_6H_8O_7$)
Formic (methanoic) acid ($CH_2O_2$)

TABLE 3-continued

Organic acids potentially suitable to adjust the acidity
of herbicides of some embodiments Lactic (2-hydroxypropanoic) acid ($C_3H_6O_3$)
Malic (2-hydroxybutanedioic) acid ($C_4H_6O_5$)
Oxalic (ethanedioic) acid ($C_2H_2O_4$)
Propionic (propanoic) acid ($C_3H_6O_2$)
Succinic acid ($C_4H_6O_4$)
Valeric (pentanoic) acid ($C_5H_{10}O_2$)

It is noted that the content of acid (organic and/or mineral) in the herbicide can be tailored to yield a pH in the desired range. It will be appreciated that the pH of an aqueous solution comprising an acid can be estimated based on the dissociation constant of the acid, quantity of acid, and other ions that contribute to acidity, for example using the Henderson-Hasselbalch equation:

$$pH = pK_a + \log_{10}(([A^-]/[HA])) \quad (XV)$$

in which HA and $A^-$ are the respective dissociated acid and conjugate base of the organic acid, and $pK_a$ is the dissociation constant of the acid.

Adjuvants

The herbicide composition in some embodiments is prepared as an aquatic solution. Without being limited by theory, penetration through the waxy surface layer on most plants is difficult for water-based solutions. To facilitate the uptake through the waxy layer, products categorized as "adjuvants" have been developed. Examples of suitable adjuvants for herbicides and kits in some embodiments include surfactants, spreader-stickers, crop oils, anti-foaming compounds, buffering agents, and compatibility agents and humectants, including combinations of two or more of the listed items (See Czarnota and Thomas, 2013; Zollinger, 2014, each of which is hereby incorporated by reference in its entirety). In some embodiments, the herbicide (or kit) includes one or more adjuvants in an amount sufficient to enhance the coating, penetration through plant surfaces, retention of moisture by the herbicide to permit absorption in the plant, and/or overall use of the herbicides described herein. Urea or other nitrogen source in amounts sufficient to enhance the foliar uptake of the herbicide may also be included in the formulation. (See, e.g., Wojcik, 2004). In some embodiments, a humectant in amounts sufficient to contain a liquid or semi-liquid state of the herbicide for a desired duration is also included in the herbicide composition. Without being limited by theory, it is contemplated that the humectant slows the drying of foliar herbicides in accordance with some embodiments herein, so that the active ingredients remain in a liquid longer, thus permitting the active ingredients to be absorbed by the plant for a longer period of time. Examples of humectants suitable for herbicide compositions, methods, and kits of some embodiments herein include, but are not limited to sugars such as glucose, fructose, honey (a combination of fructose and glucose), sucrose (table sugar), and, as well as glycerin, glycerol, sodium hexametaphosphate, a variety of other commercially available products, as well as combinations of two or more of any of the listed items. It is noted that in addition to functioning as a nutrient in some embodiments, Boron can also enhance the uptake of other nutrients such as potassium. Accordingly, in some embodiments, an herbicide composition also includes Boron in amounts sufficient to enhance the uptake of K+ may also be included in the herbicide composition. (Howard et al., 1998, which is hereby incorporated by reference in its entirety). As such, in some embodiments, the herbicide composition, kit, or method comprises Boran as an inactive ingredient, or as an active ingredient and an active ingredient (for example, if K+ is also present).

Examples of suitable adjuvants for herbicides, kits, and methods of some embodiments include, but are not limited to, crop oil concentrate, emulsifiers, penetrants (e.g., emulsified methylated seed oil (MSO), or LI700 penetrant (Loveland Products)), and surfactants (e.g., nonylphenol ethoxylate; benzylcocoalkyldimethyl quaternary ammonium salt; blend of petroleum hydrocarbon, alkyl esters, organic acid and/or mineral acid, and anionic surfactant; C9-C11 alkylpolyglycoside; phosphated alcohol ethoxylate; natural primary alcohol (C12-C16) ethoxylate; di-sec-butylphenol EO-PO block copolymer; polysiloxane-methyl cap; nonylphenol ethoxylate; tridecyl alcohol ethoxylate; tallow amine ethoxylate PEG400, dioleate 99; vegetable or seed oils and their esters; detergents such as sodium dodecyl sulfate), and urea-ammonium nitrate, which can enhance absorption. In some embodiments, the adjuvant further comprises a humectant as described herein. In some embodiments, the humectant, for example a sugar, is present in the composition at a concentration of at least about 0.1M, for example at least about 0.1M, 0.5M, 1M, 1.5M, 2M, 2.5M, 3M, 3.5M, 4M, 4.5M, or 5M, including ranges between any two of the listed values, for example about 0.1M 5M, 0.1M 4M, 0.1M 3M, 0.1M 2M, 0.5M 5M, 0.5M 4M, 0.5M-3M, 0.5M-2M, 1M-5M, 1M-4M, 1M-3M, 1M-2M, 1.5M-5M, 1.5M-4M, 1.5M 3M, or 1.5M 2M. In some embodiments, the adjuvant comprises, consists of, or consists essentially of urea and a silicone surfactant (e.g., WIDESPREAD silicone surfactant, Loveland Products). In some embodiments, the adjuvant comprises, consists of, or consists essentially of urea and a penetrant (e.g., LI700 penetrant, Loveland Products). In some embodiments, the adjuvant comprises, consists of, or consists essentially of canola oil and a detergent (e.g., JOY™ liquid detergent). In some embodiments, the adjuvant comprises, consists of, or consists essentially of a silicone surfactant (e.g., WIDESPREAD® silicone surfactant, Loveland Products) and methylated seed oil (MSO). In some embodiments, the adjuvant comprises, consists of, or consists essentially of a silicone surfactant (e.g., KINETIC® silicone surfactant), urea, and sucrose. In some embodiments, the adjuvant comprises, consists of, or consists essentially of canola oil and a detergent (e.g., JOY™ liquid detergent). In some embodiments, the adjuvant further comprises a humectant, for example a sugar humectant as described herein.

It is contemplated that in preparing formulations of herbicides in some embodiments, one or more adjuvants are combined with dry components and an aqueous solvent at, or shortly preceding the time of intended use. At the time of this patent application, many suitable adjuvants that are approved for agricultural use are available in liquid form including the examples of suitable adjuvants included in the previous paragraph. Dry forms of the silicone surfactant currently exist (Roberts et al. 199), but are not yet approved for agriculture use in North America. Subsequent to approval for agricultural use, it is intended that the dry form be available as an option for incorporation in the formulation of some embodiments herein.

Herbicide Products

The herbicide in accordance with some embodiments herein can be part of, or can be readily prepared from a number of suitable "herbicide products." Accordingly, some embodiments include an herbicide product. Such herbicide products can be available and scaled for consumer and/or commercial use and include, but are not limited to:

Dry product. Some embodiments include a dry packaged product suitable for dissolution in an appropriate volume of water (tap, pond, well, or the like) at or near the time of use. Moreover, such a dry packaged product can comprise at least one nutrient (e.g., a macronutrient such as K, N, S, Mg, or P, and/or a micronutrient such as boron, zinc, molybdenum or iron), an organic or mineral acid, and one or a combination of adjuvants, and can be constituted by the addition of water.

Dry packaged material. Some embodiments include a dry package comprising the nutrient(s) and organic acid(s) for dissolution in an appropriate volume of water (tap, pond, well, or the like), and to which a suitable adjuvant is added at the location and time of use. In some embodiments, the adjuvant comprises a surfactant.

In some embodiment, the dry product or dry package material as described herein is provided in a kit comprising unit quantities of the nutrient, organic or mineral acid, and adjuvant in molar ratio such that dissolving or diluting the nutrient, acid, and adjuvant in a prescribed volume of water will yield an herbicide composition having the nutrient molarities and pH values described herein. In some embodiments, the pH is about 4 to about 7.

Liquid formulation. Some embodiments include a liquid formulation, for example a "ready to use" or "nearly ready to use" formulation. The liquid formulation can be packaged. In some embodiments, the liquid formulation is provided in concentrated form, for dilution in an appropriate volume of water (tap, pond, well, or the like), and to which a suitable liquid adjuvant is added at the location and time of use. As such, the liquid formulation can be accompanied with an adjuvant. In some embodiments, the liquid formulation is provided as a complete liquid formulation of herbicide at concentration for immediate use. Such an herbicide can comprise the nutrient(s) and organic or mineral acid(s), and one or a combination of specified adjuvants.

It is noted that accidental or intentional foliar application of excessive amounts of conventional fertilizer can act as burn-down herbicides. However, this can run the risk of soil contamination, crop damage, and, or entry of undesirable quantities amounts of fertilizer to surface and ground water. For these reasons, the use of conventional fertilizers as herbicides may not be permitted by industry guidelines or government regulations in the United States. In some embodiments, the herbicides are distinct from, and offer additional advantages over burn-down herbicide effects of conventional fertilizers. In some embodiments, the herbicide provides a level of nutrient sufficient to kill weeds, but the amount of the sprayed nutrient reaching the soil directly and the amount of that nutrient released to the soil from decomposed dead weeds, represents a small fraction (estimated 1-2%) of the amount of that same nutrient applied to a crop during normal seasonal soil fertilization through plant roots. Thus, compositions according to embodiments herein are unlikely to interfere with a fertilization regimen. However, such compositions can contribute a minor amount of fertilizer to that program if the seasonally appropriate nutrient is selected as an active component of the herbicide formula. In some embodiments, the herbicide is formulated comprising a combination of nutrients that are appropriate for the control of weeds growing among a crop at a particular stage of crop development and ripening, so that the herbicidal nutrients are also suitable for the crop at that stage of growth development or ripening. For instance, for many crops a potassium-based herbicide formulation may be preferred early in the growing season, a nitrogen-based formulation later in the season. (Johnson, 2016) For a crop requiring Zn fertilization early in the crop's development, a Zn-based herbicidal formulation could be applied in accordance with some embodiments herein.

An additional advantageous feature of some embodiments is the reduced chance of unintended harm to off-target plants resulting from drift of this nutrient-based herbicide. The herbicidal effect derives from the high nutrient concentration of the spray formulation applied to the targeted weeds. Drift to crops which are not the direct target of the herbicide spray will occur at an ineffectively dilute concentration of the herbicide more akin to a foliar fertilizer, and less likely to have harmful effects on the cash crop or desired landscape.

Experiments to date have demonstrated the strong herbicidal effect of various formulas of various embodiments, with complete kills and no regrowth observed in multiple species of monoecious and dicotyledonous plants, in the greenhouse and in the field (see Examples 1-8).

K-based fertilizer products are commonly used in agriculture and gardening for application as a foliar fertilization spray to cash crops, landscapes, and gardens. However, these products must be formulated specifically to avoid tissue damage to the target species, and as a consequence the amount of K+ applied and thus available for absorption and delayed burn-down is far lower than concentrations of the herbicidal formulations according to some embodiments herein (Christensen, 2005). For example, a foliar application of $KNO_3$ or $K_2SO_4$, commonly recommended at 6-10 pounds of product in 100 gallons of water (Havlin, et al., 2014), produces a K foliar fertilizer solution of between 0.07 M and 0.12 M for the $KNO_3$ and between 0.03 M and 0.05 M for the $K_2SO_4$. A foliar application of KCl or $K_2S_2O_3$, commonly in the range of 2-4 pounds of product in 100 gallons of water depending on the crop (Havlin, op cit.), produces a foliar fertilizer solution of between 0.03 M and 0.6 M for the KCl, and between 0.01 M and 0.02 M for the $K_2S_2O_3$.

In contrast, it is contemplated that in some embodiments, it is suitable for the herbicide to have a nutrient molarity at or near the lower end of molarities that effectively disrupt metabolic processes upon absorption by foliar tissues.

In some embodiments, the herbicide preferably has a nutrient nolarity of about 1.5 to about 2.5 molarity, and an acidity of between about pH 4.0 and about pH 7.0 (which can be achieved when required using a suitable organic or mineral acid). Herbicides comprising potassium as an active ingredient in some embodiments are formulated with solution molarities ranging from about 1.5 and about 2.0 (for example, about 1.5, 1.6, 1.7, 1.8, 1.9, and 2.0, including ranges between any two of the listed values), titrated with an organic or mineral acid to an acidity of approximately pH 5.5. Below approximately 1.0 M the treatment does not result in sufficient absorption of K+. Above approximately 2.0 M the treatment appears to damage the cuticle too quickly for optimal K+ uptake. The herbicide can further comprise a suitable amount of adjuvant comprising a liquid penetrant, silicon-based surfactant, or another surfactant, or other components. Without being limited by theory, it is contemplated that the surfactant is recommended for beneficial spreading of the herbicide on plant surfaces. The herbicide can further comprise urea or another nitrogen-based fertilizer. Without being limited by theory, it is contemplated that the urea or nitrogen based fertilizer can enhance absorption of K+. The herbicide can further comprise a suitable amount of humectant comprising a carbohydrate such as a sugar. Without being limited by theory, it is contemplated that the humectant can expand the amount of time that the active ingredient of the herbicide is available for absorption on plant surfaces such as leaves. Examples of herbicides comprising potassium as an active ingredient in accordance with some embodiments are described in Examples 1-7 herein.

Although the nutrients K and N are used as exemplary nutrients for test purposes (see Examples 1-9), additional formulations based on nutrients other than K or N are being tested and similar results are contemplated in accordance with methods and kits of some embodiments herein.

In some embodiments, any of the herbicide compositions described herein further comprises a second herbicide, wherein the second herbicide is a non-nutrient herbicide. Without being limited by theory, it is contemplated that an herbicide comprising, consisting of, or consisting essentially of a nutrient as described herein can be used in conjunction with other classes of herbicide to achieve efficient killing of target plants. In herbicide compositions, kits, and methods of some embodiments, the second (non-nutrient) herbicide comprises, consists of, or consistent essentially of an herbicide shown in Table 3.1, or a combination of two or more of the herbicides of Table 3.1.

TABLE 3.1

| Non-nutrient herbicides | |
|---|---|
| 2,4-D | Imazamox |
| Aminocyclopyrachlor | imazapic |
| Aminopyraild | Imazapyr |
| Bromcil | Metsulfuron |
| Chlorobenil | Penoxsulam |
| Chlorsulfuron | Picloram |
| Clethodim | Prometron |
| Dicamba | Rimsulfuron |
| Diuron | Ropoxycarbazone |
| Endothall | Sethoxydim |
| Flumioxazzin | Simazine |
| Fluroxypyr | Sulfometuron |
| Fusilade | Sulfosulfuron |
| Glufosinate | Tebuthiuron |
| Glyphosate | Terbacil |
| Hexazinone | Triclopyralid |

Methods of Killing Plants

Some embodiments relate to methods of inducing phytotoxic effects in plants which are postemergence (e.g., killing, defolitating, and/or desiccating the plants or portions thereof). Briefly, an aqueous composition, for example an herbicide as described herein, can be applied to foliar portions of the plant. This aqueous composition includes a nutrient. The nutrient can be a macronutrient such as a K compound, a P compound, an N compound, a Mg compound, a Ca compound, a S compound, or a micronutrient such as a Zn compound, a B compound, a Mo compound, an Fe compound. Combinations of nutrients may also be used. The composition can also include at least one organic or mineral acid and one or more specified adjuvants. This combination allows for the nutrient to be absorbed by the plant in quantities that are toxic to the plant. The plant then becomes severely compromised and exhibits phytotoxicity. In some embodiments, the plant dies. In some embodiments, the phytotoxic effects are systemic. In some embodiments, the killing is topical, for example to target undesired growths or shoots (e.g., "suckers") off of an established plant, such as a grape vine or tree. In some embodiments, the herbicide is used as a desiccant, and the plants are desiccated by the herbicide. By way of example, the herbicide can be used as a desiccant for a crop such as cotton, potatoes, or soybeans, for the production of vegetable seeds, or for two or more of these. In some embodiments, the crop is organic. In some embodiments, the herbicide is used as a desiccant for a crop that does not mature until late in the season and stays green, for example in certain European countries and in soybean production in the southern United States. In some embodiments, the herbicide is used to target weeds prior to a grain harvest. Without being limited by theory, the herbicide can cause desiccation of the weeds, and facilitate access to the grain for harvest, for example so that there is less foliar material to damage a combine or become blended with the harvested crop. Herbicides according to some embodiments herein are prepared as aqueous solutions by adding a prescribed amount of a specified nutrient salt in combination with a prescribed amount of a specified acid to a prescribed volume of water. Following dissolution of these materials in the water, a prescribed amount of one or more specified adjuvants is added to complete the mixture. The mixture is then sprayed upon the surface tissue of the targeted weeds in an amount sufficient to thoroughly coat the exposed surfaces of the target plants such as weeds. Without being limited by theory, it is contemplated that thoroughly coating the target plant with the liquid herbicide composition of some embodiments can facilitate absorption of the nutrients in excess as described herein, thus yielding efficient killing. A repeat application can be applied within about fourteen days if weed kill is insufficient for horticultural purposes.

The rate of application of the herbicide for a specific site will be determined by test applications at the sites. However, the estimated application rate in accordance with some embodiments is 20-40 gallons of prepared solution for an acre of coverage, preferably about 30 gallons of prepared solution for an acre of coverage. The amount of the solute to be dissolved in the 20-40 gallons will vary depending on the goals and purposes of the applicator.

For example, when applied as an herbicide protecting a cash crop or landscape vegetation, the selected nutrient and amounts of active and inactive components in the herbicide can be formulated to accommodate or supplement the seasonal fertilizer regimen of the protected vegetation while at the same time achieving the desired level of weed control.

When applied solely for broad herbicidal control, for example in highway medians or rights-of-way, in accordance with some embodiments, a different nutrient and amount of active and inactive component in the herbicide can be selected to achieve the most cost effective herbicidal action.

It has been observed that some herbicides in accordance with some embodiments herein can be administered to monocots (e.g., grass) and dicots, so as to kill the dicots, but not the monocots (see Example 8). Accordingly, in some embodiments, the method comprises administering the herbicide to dicot plants (e.g. weeds) that are disposed among monocot plants (e.g. lawns or turf), so as to kill the dicot plant but not the monocot plants. In some embodiments, the herbicide comprises a nutrient that comprises nitrogen. In some embodiments, the nutrient is provided as a nutrient compound comprising ammonium sulfate. In some embodiments, the ammonium sulfate concentration in the herbicide is about 2M.

It is contemplated that for some applications, once an herbicide has been systemically absorbed by a target plant, it may be desirable to perform a "burn-down" to rapidly eradicate foliar tissues of target plants. The herbicide that has been absorbed systemically (in the roots and the like) will prevent the target plants from growing back after the burn-down. Accordingly, in some embodiments, burn-down is applied after the post-emergence, systemic, non-selective herbicide described herein. In some embodiments, a kit is provided, comprising a systemic, a non-selective herbicide described herein and a burn-down product. Example burn-down products that can be subsequently applied to the target plants or provided in the kit include, but are not limited to, aquatic solution of potassium acetate+pelargonic acid; aquatic solution of potassium nitrate+pelargonic acid; aquatic solution of ammonium nonanoate+citric acid; and/or aquatic solution of ammonium sulfate decanoic acid. Examples of suitable commercial burn-down products for some embodiments include, but are not limited to "Suppress®": Westbridge Agricultural Products, EPA Registration Number 51517-9, the active ingredients of which are caprylic (octanoic) acid (47%) and capric (decanoic) acid (32%); "Scythe®": Dow AgroSciences, EPA Registration Number 62719-529, the active ingredients of which are pelargonic (nonanoic) acid (57.0%) and "other fatty acids [C6-C12" (3%); and "Axxe®": BioSafe Systems, EPA Registration Number 70299-23, the active ingredient of which is ammonium nonanoate (40%), an ammonium salt of pelargonic acid. Accordingly, in some embodiments, a burn-down product comprises on or more of: caprylic (octanoic) acid and capric (decanoic) acid; a composition comprising pelargonic (nonanoic) acid and C6-C12 fatty acids; and a composition comprising ammonium nonanoate, and an ammonium salt of pelargonic acid. In some embodiments, the burn-down product comprises one or more of a composition comprising: caprylic (octanoic) acid (47%) and capric (decanoic) acid (32%); pelargonic (nonanoic) acid (57.0%) and "other fatty acids [C6-C12]" (3%); or ammonium nonanoate (40%) and an ammonium salt of pelargonic acid.

In addition to the items above, the following particular options are set forth:

1. A method of inducing phytotoxicity in a plant, the method comprising administering an aqueous composition to foliar portions of the plant, wherein the aqueous composition comprises:
    at least one nutrient compound selected from the group consisting of: a potassium compound, a phosphorus compound, a nitrogen compound, a magnesium compound, a sulfur compound, a calcium compound, a micronutrient, and a combination of two or more of the listed items, wherein the nutrient compound comprises a nutrient; and
    at least one adjuvant,
    wherein the pH of the aqueous composition is about 4 to about 7,
    thereby administering an excess of the nutrient to the plant,
    whereby the nutrient is absorbed by the plant in excess, thereby inducing phytotoxicity in the plant.
2. The method of option 1, wherein the phytotoxicity comprises killing the plant, the method comprising systemically administering the aqueous solution, thereby killing the plant.
3. The method of option 1, wherein the phytotoxicity is in a portion of the plant, the method comprising topically administering the aqueous solution, thereby inducing topical phytotoxicity in the plant.
4. The method of option 2, wherein the excess nutrient absorbed by the plant causes terminal physiological disruption and killing of the plant.
5. The method of any one of options 1-4, wherein the excess nutrient absorbed by the plant causes opening of stromata of the plant, thereby dessicating the plant.
6. The method of any one of options 1-5, wherein the aqueous composition further comprises an organic acid or a mineral acid.
7. The method of any one of options 1-6, wherein the pH of the composition is about 4.5 to about 5.5.
8. The method of any one of options 1-7, wherein the concentration of the nutrient in the aqueous composition is about 1 M to about 2 M.
9. The method of any one of options 6-8, wherein the aqueous composition comprises the organic acid, and the organic acid is selected from the group consisting of acetic acid, citric acid, lactic acid, formic acid, succinic acid, tartaric acid, malic acid, and oxalic acid.
10. The method of any one of options 6-8, wherein the aqueous composition comprises the mineral acid, for example HCl.
11. The method of any one of options 1-10, wherein the nutrient compound is selected from the group consisting of: potassium acetate, potassium lactate, potassium formate, potassium citrate, and potassium bitartrate, and wherein the nutrient comprises potassium.
12. The method of any one of options 1-11, wherein the nutrient compound is selected from the group consisting of: a potassium compound, a phosphorus compound, a nitrogen compound, a sulfur compound, a calcium compound, a micronutrient, and a combination of two or more of the listed items.
13. The method of any one of options 1-10, wherein the nutrient compound comprises magnesium sulfate, and wherein the nutrient comprises magnesium.
14. The method of any one of options 1-10, wherein the nutrient compound comprises ammonium sulfate, and wherein the nutrient comprises nitrogen.
15. The method of any one of options 1-14, wherein the nutrient compound comprises:
    an ion comprising K, P, N, Mg, S, Ca, or the micronutrient; and
    an oppositely-charged ion, wherein the oppositely-charged ion is not an herbicide in the quantities of the composition.
16. The method of any one of options 1-15, wherein the nutrient compound does not comprise glyphosate.
17. The method of any one of options 1-16, wherein the composition is applied as a water-based spray.
18. The method of any one of options 1-17, wherein the absorption of the nutrient is forestalled for 2-4 days.
19. The method of any one of options 1-18, wherein the composition has a low point of deliquescence (POD), whereby the composition is retained in semi-liquid state on the foliar portion of the plant for 2-4 days.
20. The method of any one of options 1-19, wherein the plant is a dicot.
21. The method of any one of options 1-19, wherein the plant is a monocot.
22. The method of any one of options 1-19, wherein the plant is a dicot, and wherein the plant is disposed among monocots, for example grass, and wherein the monocots are not killed.
23. The method of option 22, wherein the nutrient compound comprises ammonium sulfate.
24. The method of option 23, wherein the nutrient comprises nitrogen at a concentration of at least 2M in the composition.
25. The method of any one of options 1-19, wherein the plant is at least one selected from the group consisting of *Allium ampeloprasum, A. cepa, A. tuberosum, Antirrhinum majus, Brassica oleracea, Calendula officinalis, Calibrachoa* sp., *Celosia* sp., *Cineraria meritima, Chloris aequitrilobia, Cosmos* sp., *Cymbalaria aequitrilobia, Echinochloa* sp., *Festuca* sp., *Fragaria*×

*ananassa, Gallium odoratum, Gazania rigens, Lantana camara, Leucanthemum paludosu, Lobelia erinus, Paludosum, Lobularia maritima, Nemophila menziesii discoidalis, Nicotiana* sp., *Pisum sativum, Portulaca oleracia, Rosmarina officinalis, Santivitalia* sp., *Viola hederacea, Viola×wittockiana, Lolium perenne, Dactylis glomerata, Festuca arundinacea, Trifolium subterraneum, Eschscholzia californica, Collinsia heterophyllia, Mathilda incana, Nemophila maculate* and *Linum lewisii.*

26. The method of any one of options 1-19, wherein the plant is at least one selected from the group consisting of *Allium ampeloprasum, A. cepa, Antirrhinum majus, Brassica oleracea, Calendula officinalis, Calibrachoa* sp., *Celosia* sp., *Cineraria meritima, Cosmos* sp., *Festuca* sp., *Fragaria×ananassa, Gallium odoratum, Gazania rigens, Lantana camara, Leucanthemum paludosu, Paludosum, Lobularia maritima, Nemophila menziesii discoidalis, Nicotiana* sp., *Pisum sativum, Santivitalia* sp., *Viola hederacea, Viola×wittockiana, Lolium perenne, Dactylis glomerata, Festuca arundinacea, Trifolium subterraneum, Eschscholzia californica, Collinsia heterophyllia, Nemophila maculate* and *Linum lewisii.*

27. The method of any one of options 1-26, further comprising a second administration within 14 days of the first administration of the composition.

28. The method of any one of options 1-27, wherein the rate of application of the composition is 20-40 gallons per acre.

29. The method of any one of options 1-28, the composition further comprising a burn down herbicide.

30. The method of option 29, wherein the burn down herbicide comprises an organic acid composition selected from the group consisting of: a composition comprising caprylic (octanoic) acid and capric (decanoic) acid; a composition comprising pelargonic (nonanoic) acid and $C_6$-$C_{12}$ fatty acids; and a composition comprising ammonium nonanoate, and an ammonium salt of pelargonic acid.

31. The method of any one of options 1-30, the composition further comprising a second herbicide, wherein the second herbicide is a non-nutrient herbicide.

32. The method of option 31, wherein the second herbicide comprises an herbicide selected from Table 3.1.

33. A kit comprising:
    a first unit quantity of a nutrient compound selected from the group consisting of: a potassium compound, a phosphorus compound, a nitrogen compound, a magnesium compound, a sulfur compound, a calcium compound, a micronutrient, and a combination of two or more of the listed items, wherein the nutrient compound comprises a nutrient;
    a second unit quantity of organic or mineral acid; and
    an adjuvant,
    wherein a ratio of the first unit quantity to the second unit quantity is configured to achieve a pH of 4 to 7 if the first unit quantity is constituted to a nutrient molarity of 0.5-2.0 in water having a pH of 7.

34. The kit of option 33, wherein the first unit quantity is comprises potassium salt and wherein the potassium salt is potassium citrate and the organic acid is glacial acetic acid, and wherein the ratio of K citrate to glacial acetic acid is about 1 mol:0.7-3.5 mol acetic acid.

35. The kit of option 33 or 34, wherein the nutrient compound is selected from the group consisting of: a potassium compound, a phosphorus compound, a nitrogen compound, a sulfur compound, a calcium compound, a micronutrient, and a combination of two or more of the listed items.

36. The kit of any one of options 33-35, wherein the organic or mineral acid is selected from the group consisting of acetic acid, citric acid, lactic acid, formic acid, succinic acid, tartaric acid, malic acid and oxalic acid.

37. The kit of any one of options 33-36, wherein the first unit quantity is of the potassium compound, and wherein the potassium compound is selected from the group consisting of: potassium acetate, potassium lactate, potassium formate, potassium citrate, and potassium bitartrate.

38. The kit of any one of options 33-37, wherein the first unit quantity is of the nitrogen compound and wherein and the nitrogen compound is ammonium nitrate.

39. The kit of any one of options 33-38, wherein the first unit quantity is of the magnesium compound and wherein the magnesium compound is magnesium sulfate.

40. The kit of any one of options 33-39, wherein the nutrient compound comprises:
    an ion comprising K, P, N, S, Ca, or the micronutrient; and
    an oppositely-charged ion, wherein the oppositely-charged ion is not an herbicide if the first unity quantity is constituted to a nutrient concentration of about 0.5 to 2.0M.

41. The kit of any one of options 33-40, which does not comprise glyphosate.

42. An aqueous herbicide composition comprising;
    at least one nutrient compound selected from the group consisting of: a potassium compound, a phosphorus compound, a nitrogen compound, a magnesium compound, a sulfur compound, a calcium compound, a micronutrient, and a combination of two or more of the listed items, wherein the nutrient compound comprises a nutrient at a concentration of at least about 0.5 M in the aqueous herbicide composition;
    an organic or mineral acid; and
    an adjuvant,
    wherein the composition has a pH of about 4 to about 7.

43. The aqueous herbicide composition of option 42, wherein the organic or mineral acid is selected from the group consisting of: acetic acid, citric acid, lactic acid, formic acid, malic acid, succinic acid, tartaric acid, and oxalic acid.

44. The aqueous herbicide composition of option 42 or 43, wherein the nutrient compound is selected from the group consisting of: a potassium compound, a phosphorus compound, a nitrogen compound, a sulfur compound, a calcium compound, a micronutrient, and a combination of two or more of the listed items.

45. The aqueous herbicide composition of any one of options 42-44, wherein the nutrient compound is a potassium salt selected from the group consisting of: potassium acetate, potassium lactate, potassium formate, potassium citrate, and potassium bitartrate.

46. The aqueous herbicide composition of any one of options 42-44, wherein the nutrient compound is a nitrogen compound and wherein and the nitrogen compound is ammonium sulfate.

47. The aqueous herbicide composition of option 42 or 43, wherein the nutrient is magnesium and wherein the magnesium compound is magnesium sulfate.

48. The aqueous herbicide composition of any one of options 42-47, wherein the nutrient is at a concentration of about 0.5 M-2.5 M.

49. The aqueous herbicide composition of option 42 or 48, wherein the nutrient is potassium citrate and the organic or mineral acid is glacial acetic acid, and wherein the ratio of potassium citrate to glacial acetic acid is about 1 mol:0.7-3.5 mol acetic acid.

50. The aqueous herbicide composition of any one of options 42-49, wherein the nutrient compound comprises:
an ion comprising K, P, N, S, Ca, or the micronutrient; and
an oppositely-charged ion, wherein the oppositely-charged ion is not an herbicide in the quantities of the composition.

51. The aqueous herbicide composition of any one of options 42-50 which does not contain glyphosate.

52. The aqueous herbicide composition of any one of options 42-51, wherein the adjuvant comprises a surfactant.

53. The aqueous herbicide composition of any one of options 52-52, wherein the adjuvant comprises a humectant.

54. A container containing 0.5 liters to 10 liters of the aqueous herbicide composition of any one of options 42-53.

55. A method of preparing an herbicidal composition comprising:
contacting a nutrient compound wherein the nutrient compound comprises a nutrient, and wherein the nutrient compound is selected from the group consisting of: a potassium compound, a phosphorus compound, a nitrogen compound, a magnesium compound, a micronutrient, and a combination of two or more of the listed items, with water to a nutrient concentration of at least 0.5 M, thereby forming an aqueous nutrient solution;
adjusting the pH of the aqueous nutrient solution to about 4 to about 7 with an organic or mineral acid; and
contacting an adjuvant with the aqueous nutrient solution,
thereby preparing an herbicidal composition.

56. The method of option 55, wherein the organic or mineral acid is selected from the group consisting of acetic acid, citric acid, lactic acid, formic acid, malic acid, succinic acid, tartaric acid, and oxalic acid.

57. The method of option 55 or 56, wherein said adjusting the pH of the aqueous nutrient solution adjusts the pH to about 4.5 to 5.5.

58. The method of any one of options 55-57, wherein the nutrient concentration is about 0.5M to 2.5M.

59. The method of any one of options 55-58, wherein the nutrient compound is selected from the group consisting of: a potassium compound, a phosphorus compound, a nitrogen compound, a micronutrient, and a combination of two or more of the listed items 60. The method of any one of options 55-59, wherein the nutrient is potassium and the potassium salt is selected from the group consisting of potassium acetate, potassium lactate, potassium formate, potassium citrate, and potassium bitartrate.

61. The method of any one of options 55-60, wherein the nutrient is nitrogen and the nitrogen compound is ammonium nitrate.

62. The method of any one of options 55-61, wherein the nutrient is magnesium and the magnesium compound is magnesium sulfate.

63. The method of any one of options 1-32, wherein the nutrient comprises a micronutrient, and wherein the plant is positioned in a right-of-way, road-sides, or in the absence of crop or ornamental vegetation.

64. The method of any one of options 1-32, wherein the nutrient comprises a macronutrient, and wherein the plant is positioned in the presence of a crop or ornamental vegetation.

65. The method of any one of options 1-32 or 55-62 wherein the adjuvant comprises a surfactant, a humectant, or both.

66. The method of any one of options 1-32 or 55-66, wherein inducing phoytotoxicity in the plant comprises systemic and topical phytotoxicity.

67. The method of any one of options 1, 3-32, or 55-66, wherein the phytotoxicity comprises dessication of the plant.

68. The method of option 67, wherein the plant is a crop that matures late in the season and stays green.

69. The method of option 67 or 68, wherein the plant is selected from the group consisting of cotton, potatoes, soybeans, or a vegetable for the production of seeds.

70. The method of option 67, wherein the dessication is prior to the harvest of a grain crop in proximity to the plant.

71. The method of any one of options 1, 2, 4-32, or 55-66, wherein the phytotoxicity comprises burn-down activity.

72. The method of any one of options 1-32 or 55-71, wherein the nutrient compound does not comprise chelated iron.

73. The method of any one of options 1-32 or 55-71, wherein the nutrient compound does not comprise iron.

74. The kit of any one of options 33-41 wherein the adjuvant comprises a surfactant, a humectant, or both.

75. The kit of any one of options 33-41 or 74, wherein the nutrient compound does not comprise chelated iron.

76. The kit of any one of options 33-41 or 74, wherein the nutrient compound does not comprise iron.

77. The aqueous herbicide composition of any one of options 42-53, wherein the nutrient compound does not comprise chelated iron.

78. The aqueous herbicide composition of any one of options 42-53, wherein the nutrient compound does not comprise iron.

79. The aqueous herbicide composition of option 53, the method of option 65, or the kit of option 74, wherein the humectant comprises a sugar selected from the group consisting of dextrose, fructose, sucrose, or a combination of any of these.

EXAMPLES

Example 1

Experimental Design and Summary of Trials 6, 7, 14-17, 21, 22, 30, 31-A, 31-B, 32-A, 32-B, 41-A, 41-B, 44, 47, 50, 54, 56, and 64

Current and past scientific and agricultural research examining the uptake of nutrients and their physiological functions has focused on levels of nutrient appropriate for growth and development of healthy plants. Although there is a literature pertaining to the harmful effects of excessive nutrient levels, no published articles have been uncovered addressing the foliar application of plant nutrients specifically as herbicides. To support this application, greenhouse experiments have been performed to test the effectiveness of herbicidal formulations both as burn-down formulations and those based upon the nutrient phytoxicity" hypothesis. These greenhouse experiments include "bracket trials" in which test formulations are prepared with concentrations and combinations of ingredients hypothesized to range between an upper excessive and a lower ineffective concentration. Greenhouse trials also are used to determine the relative effectiveness of various combinations of nutrient salt, acidifier, and the adjuvant ingredients used to maximize the absorption of active ingredients. Greenhouse trials include young ornamental monocot and dicot plants, ornamentals of the same taxonomic family or genus of field weeds, and true field weeds grown from seed. Promising formulations from the greenhouse are then tested in the field on natural mixes of field weeds to verify effectiveness in a practical scenario.

Sources of K for the experimental formulations include a variety of both commercial fertilizers and sources of K not generally used in agricultural practice. Data resulting from these tests demonstrated that when applied in suitable amounts and concentrations, at suitable acidity, with suitable adjuvants, the herbicide in accordance with some embodiments herein was effective at killing the target plants in greenhouse and field experiments.

Tables 4A-4C below shows the various species of plants that were tested and references the test numbers in which they were used.

TABLE 4A

Greenhouse trial plants with reference numbers for data tables, and trials in which each species was used.

| | Scientific Name | Common name | Test #'s Used |
|---|---|---|---|
| 1. | *Allium ampeloprasum* | Leek "American Flag" | 31 |
| 1a. | *Allium tuberosum* | Garlic chive | 57 |
| 2. | *Allium cepa* | Onion "Torpedo Red" | 32, 33, 41 |
| 3. | *Antirrhinum majus* | Snapdragon | 6, 7, 17, 27, 29, 41, 56 |
| 4. | *Brassica oleracea* | Broccoli "Marathon" | 30 |
| 5. | *Brassica oleracea* | Kale "Dinosaur" | 31, 44, 47, 57, 63, 64 |
| 6. | *Brassica oleracea* | Cabbage "Red Jewel" | 32, 33 |
| 7. | *Calendula officinalis* | Common marigold "Bonanza Yellow" | 8, 8A, 9, 13 |
| 8. | *Calibrachoa* sp. | Million bells | 19 |
| 9. | *Celosia* sp. | Woolflower | 17, 18 |
| 9a. | *Chloris virgata* | Feather fingergrass | 56 |
| 10. | *Cineraria meritima* | Dusty miller "Silver Dust" | 8, 8A, 9, 10, 12, 13, 14, 15, 16, 17, 18, 19, 27, 29, 54 |
| 11. | *Cosmos* sp. | Cosmos | 30, 41 |
| 11a. | *Cymbalaria aequitriloba* | Cymbalaria | |
| 11b. | *Dichondra repens* | Dichondra | 44, 47 |
| 11c. | *Echinochlora* | Barnyard grass | 56 |
| 12. | *Festuca* sp. | Fescue (grass) | 16 |
| 13. | *Fragaria x ananassa* | Strawberry "Eversweet" | 20, 21, 22, 23, 24, 25, 26, 26, 47 |
| 14. | *Gallium odoratum* | Sweet woodruff | 6, 7 |
| 15. | *Gazania rigens* | "Beda" | 20, 21, 22, 25, 26, 27 |
| 16. | *Lantana camara* | White | 30, 31 |
| 17. | *Leucanthemum paludosum* | Paludosum daisy | 32 |
| 17a. | *Lobelia crinus* | Lobelia | 54 |
| 18. | *Lobularia maritima* | Alyssum "AlicePurple" | 32, 33 |
| 18a. | *Matthiola incana* | Double-flowered stock | 58, 63, 64 |
| 19. | *Nemophila menziesii discoidalis* | Baby blue eyes | 6, 7, 20, 21, 22, 25, 26 |
| 20. | *Nicotiana* sp. | | 19 |
| 21. | Pasture blend 1 (P1)* | | 8, 8A, 9, 10, 12, 13, 14, 15, 16, 18, 22, 25, 26, 27, 29, 30 |
| 22. | Pasture blend 2 (P2)** | | 8, 8A, 9, 10, 12, 14, 15, 16, 17, 19, 20, 21, 23, 24, 31, 32, 41, 44, 47, 57, 62, 64 |
| 23. | *Pisum sativum* var. *saccharatum* | Snow pea | 31 |
| 23a | *Portulaca olerace* | Common purslane | 54 |
| 23a. | *Rosmarina officinalis* | Rosemary | 44, 47, 57, 63, 64 |
| 24. | *Santivitalia* sp. | Creeping zinnia "Compact Yellow Ice" | 7 |
| 25. | *Viola hederacea* | Viola "Australian Violet" | 8, 8A, 10, 12 |
| 26. | *Viola x wittockiana* | Viola "Sugarplum" | 6, 8A, 56, 63, 64 |

*Pasture blend #1: < 6 weeks since germination.
**Pasture blend #2: > 6 weeks since germination

TABLE 4B

"Pasture" Seed Blend for Greenhouse Trials.

| Scientific Name | Common name | Proportion |
|---|---|---|
| Lolium perenne | Perennial ryegrass | 40% |
| Dactylis glomerata | Perennial bunchgrass | 16% |
| Festuca arundinacea | Tall fescue (grass) | 12% |
| Trifolium subterraneum | Subterranean clover | 24% |
| Eschscholzia californica | California poppy | 2% |
| Collinsia heterophyllia | Purple Chinese houses | 2% |
| Nemophila maculata | Five spot | 2% |
| Linum lewisii | Blue flax | 2% |
|  |  | 100% |

These results include broad herbicidal effect on a variety of grasses and broad-leaf plants. The composition of "Pasture" Seed Blend is provided in Table 4B which is a mixture of three common pasture grasses grown in California, one subterranean clover, and four common California wildflowers. As noted in Table 4B above, Pasture blend #1 are tested at less than 6 weeks after germination as a simulation of young weeds. Pasture blend #2 represents plants tested at more than 6 weeks since germination as a simulation of mature weeds.

The majority of greenhouse trials conducted date have been of one basic design:

1. Samples of different species of flowering plant and grass are exposed to different formulations of the herbicide in accordance with some embodiments, prepared in a range of concentrations, in combination with potentially suitable adjuvants, and applied as an aquatic spray. Experimental plants are purchased either from a local nursery, grown from ornamental and weed seed packs, or grown from seeds of a custom blend prepared specifically for this project and listed in Table 4B. The experimental variable in a typical test is the molar mass concentration of the nutrient salt being examined. Other factors including pH, nitrogen source, and the amount and composition of surfactant or penetrant are constants within a trial except when one of these factors is itself the variable of interest in the experiment. Experiments are controlled unless irrelevant for a particular test.

2. Standard techniques to reduce experimental error are employed including use of controls; standard spray application pressures; standardized growing conditions, growing medium, containers, and source irrigation water; and preparation and shipping of samples for laboratory analysis according to required standard laboratory protocols.

3. Plants are sprayed with the experimental formulation, always in late afternoon (greenhouse tests), or in early morning (field tests), are observed over as many as several weeks, and their visible state of decline scored by the same examiner on a 9 points system relying on visual effects of toxicity. (Table 5.)

TABLE 5

| Toxicity Scoring | |
|---|---|
| Observation | Score |
| No visible effect: Plant essentially identical to control. | 1.0-1.5 0-1.5* |
| Slight effect: Leaf tips desiccated; flowers if present wilted. | 2.00-2.5 |
| Strong effect: Portions of leaf beyond tip desiccated; stems desiccated; some browning. | 3.0-3.5 |

TABLE 5-continued

| Toxicity Scoring | |
|---|---|
| Observation | Score |
| Severe effect: All leaves and flowers if present desiccated and browned. Little or no green tissue visible. | 4.0-4.5 |
| Dead: Completely wilted and lodged; no green tissue (assigned only after four days of Score 4). | 5.0 |

*In later greenhouse trials with weeds, 9-point scoring was converted to 10-point scoring as more consistent with industry practice. "No visible effect" scoring was changed from "1.0-1.5" to "0-1.5"

Scores of half-value are, also used: 0, 0.5, 1.0, 1.5, 2.0, 2.5, etc.

4. The estimated successful herbicidal effectiveness of a formulation was determined from a combination of averaged and cumulative scores of 4.0 to 5.0 observed approximately 14 days or longer after application: "All leaves and flowers if present desiccated, browned, wilted, and stems or blades lodged; no green tissue visible; no regrowth from roots visible."

The observed effects were both short-term within a week or so following application of the herbicide, and long-term of two weeks or more with no visible recovery of the treated plants from roots presumably killed as well by the foliar application of the herbicide.

Tables 6A and 6B, below, describe the test parameters and results of tests of foliar herbicides in accordance with some embodiments herein. Tables 6A and 6B, below, summarize the experimental parameters and results of the tests that yielded suitable herbicidal effects, including Test Number, Active Nutrient, Formulation Code, Molarity of Nutrient, Toxicity Score, and reference numbers of plant species used in each test. Active nutrients tested were potassium (K) or nitrogen (N). The molarity of the active ingredient ranged from 1.0 to 2.0 M for potassium, 2.0 M for nitrogen, 1.0-2.0M for zinc. The experimental pH ranged from 4.02 to 7.75. It is noted that hyphenated test identifiers (e.g. 31-A, 31-B) may also be identified herein without the hyphen (e.g. 31A, 31B). For ease of review, Tables 6A and 6B are depicted merged into a single table in landscape form in FIG. 7. The references to the Figure and/or Example numbers shown in Table 6A are not exhaustive, and are merely provided for quick reference.

The data presented in Tables 6A and 6B are interpreted as follows: The "Trial Number, Sample Number" refers to experimental descriptions and results in the Project Lab Books, Volumes 1 and 2, "Notes" are any comments clarifying the indicated trial. The "Active Nutrient" refers to the primary nutrient that was the focus of the Trial, for instance Potassium, Nitrogen, or Zinc. The "Solution Formulation" keys to the chemical reaction equations presented listed in Formulas (I)-(XIV) above that describe the herbicidal solutions used in the test. All trials are carried out using solutions of known concentration of the Active Nutrient measured in Moles/Liter of water. Table 6B: Where necessary, the acidity of the Trial solution is adjusted to a desired pH (solution pH) with the addition of mineral or organic acid ("Acid Added/ L"). The number of days after application of an herbicidal solutions to the plants used in that test, combined with the Herbicidal. Effect Score (Table 5), is indicated as follows: "5/4.5" indicates that 5 days following the application of the test solution, the plants to which the spray was applied yielded an average visual effect score of 4.5 ("severe-to-fatal" tissue damage to the plant"). A note of 14/5.0 would indicate an average effects score of 5 ("death of entire plant") at day 14 for that particular test.

1) Using Trial 32A Sample 1 (S-1) as an example, the nutrient tested in that experiment was Potassium (K) present as a solution of K-acetate acidified with citric acid. 2) K-acetate was present in a 2.0 molar (196 g/L) concentration for the first experiment, acidified with 100 g of citric acid to a pH of 5.01, As indicated on the table, 1.5 M and 1.0M were also used in Trial 32A. 3) Results for Trial 32A (the "Score"; refer to Table 5) are shown to be as follows: "3/3.7" means that 3 days after spray application of solution 32-A, an average toxicity score of 3.7 was observed; "5/4.3" that on day 5, an average score of 4.3 was observed; "9/4.2" that on day 9 an average score of 4.2 was observed, and "15/4.5" that on day 15 an average score of 4.5 was observed. As noted, Trial 32A ended on Day 1.5. 4) Plants used in Trial 32-A are 18 (Alyssum), 17 (Paludosum daisy), 6 ("Red Jewel" cabbage), 2 onion ("Torpedo Red"), and 22 (Pasture blend #2). (Refer to Tables 4A-C for identification on plant test species).

TABLE 6A

Summary of trial results (part I)

Figure 2:
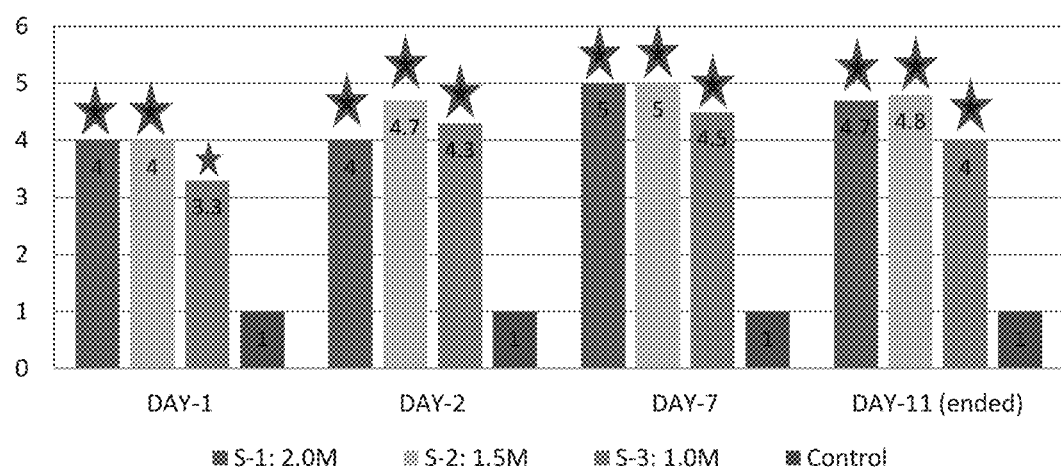
FIG. 2 depicts the average toxicity scores for the three plants used in Trial 14, which tested an embodiment of an herbicide composition and method of using the same. The plants were numbered 21, 22, and 10, corresponding to Pasture Blend 1, Pasture blend 2 and *Cineraria meritima* (Dusty miller "Silver Dust" refer to Tables 4A and 4B for plant species identification). Solution 1 (S-1) corresponds to a 2.0 molar solution of potassium acetate, pH 5.28 achieved with 30% acetic acid, and the inactive adjuvants urea and WIDESPREAD® silicone surfactant (Loveland Products). S-2 is a similar solution of 1.5 molarity, pH 5.29. S-3 is a similar solution of 1.0 molarity, pH 5.29. (Refer to Tables 6A and 6B for trial solutions, details and results). Results of Trial 14 indicate excellent phytotoxic effects ranging from 4.0 to 5.0 ("severe-to-fatal") between Day 1 and Day 7 at a solution concentration of 2.0M; toxicity levels of from 4.0 and 4.8 between Day 1 and Day 11 at a concentration of 1.5M; and between 4.3 and 4.0 between Day 2 and Day 11 at a concentration of 1.0M. Controls sprayed only with water and a proprietary adjuvant mixture showed no effects.
Figure 3:
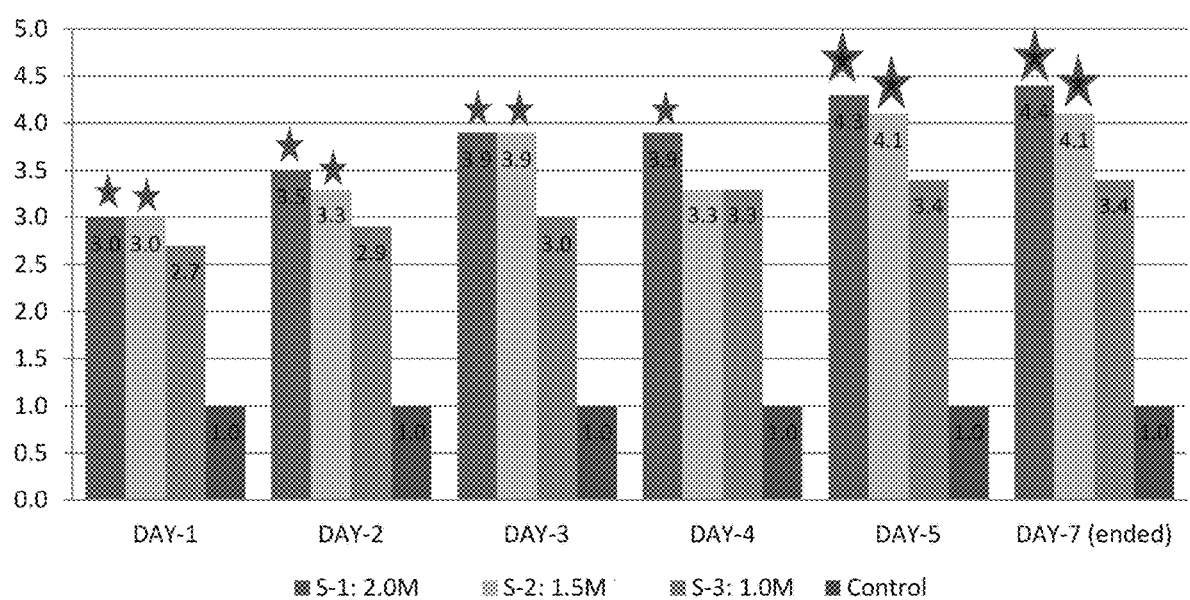
FIG. 3 depicts the average toxicity scores for the three plants used in Trial 22, which tested an embodiment of an herbicide composition and method of using the same, The plants were numbered 13, 15, and 19, corresponding to Pasture Blend 2, *Fragariaxananassa* (Strawberry "Eversweet"), *Gazania rigens* (Gazania "Beda"), and *Nemophila menziesii discoidalis* (Baby blue eyes refer to Tables 4A and 4B for plant species identification). Solution 1 (S-1) corresponds to a 2.0 molar solution of potassium acetate, pH 5.01 achieved with succinic acid, and the inactive adjuvants urea and WIDESPREAD® silicone surfactant (Loveland Products). S-2 is a similar solution of 1.5 molarity, pH 5.00. S-3 is a similar solution of 1.0 molarity, pH 4.98. (Refer to Tables 6A and 6B for trial solutions, details and results). Results of Trial 22 indicate excellent phytotoxic effects of 4.3 and 4.4 ("severe-to-fatal") resulted at Day 5 and Day 7 at a solution concentration of 2.0M, and of 4.1 on Day 5 and Day 7 at a solution concentration of 1.5 M. A 1.0M solution achieved reduced phytotoxic effect. Controls sprayed with water only and a proprietary adjuvant mixture showed no effects.

| Trial #, Sample # | Ref. to Example # and Figure # | Notes | Active Nutrient | Solution Formulation |
|---|---|---|---|---|
| T6, S1 | | Greenhouse trial | Potassium (K) | K-citrate, plus adjuvants |
| T6, Control 1 | | | None | H20 only |
| T7, S2 | | Greenhouse trial | Potassium (K) | K-citrate, plus adjuvants |
| T7, Control 1 | | | None | H20 + adjuvants |
| T7, Control 2 | | | None | H20 only |
| T13, S1 | Example 3, FIG. 1 | Greenhouse trial | Potassium (K) | K-citrate + citric acid as freeze-dried lemon juice, plus adjuvants |
| T13, S2 | Example 3, FIG. 1 | | Potassium (K) | K-citrate + citric acid as freeze-dried lemon juice, plus adjuvants |
| T13, Control | Example 3, FIG. 1 | | None | H2O + adjuvants |
| T14, S1 | Example 4, FIG. 2 | Greenhouse trial. Test 14, 15 and 16 have same actives, diff. adjuvants | Potassium (K) | K-acetate + glacial acetic acid, plus adjuvants |
| T14, S2 | Example 4, FIG. 2 | | " | K-acetate + glacial acetic acid, plus adjuvants |
| T14, S3 | Example 4, FIG. 2 | | " | K-acetate + glacial acetic acid, plus adjuvants |
| T14, Control 1 | Example 4, FIG. 2 | | None | H20 + adjuvants |
| T14, Control 2 | Example 4, FIG. 2 | | None | H20 only |
| T15, S1 | | Greenhouse trial. Test 14, 15 and 16 have same actives, diff. adjuvants | Potassium (K) | K-acetate + glacial acetic acid, plus adjuvants |
| T15, S2 | | | " | K-acetate + glacial acetic acid, plus adjuvants |
| T15, S3 | | | " | K-acetate + glacial acetic acid, plus adjuvants |
| T15, Control 1 | | | None | H20 + adjuvants |
| T15, Control 2 | | | None | H20 only |
| T16, S1 | | Greenhouse trial. Test 14, 15 and 16 have same actives, diff. adjuvants | Potassium (K) | K-acetate + glacial acetic acid, plus adjuvants |
| T16, S2 | | | " | K-acetate + glacial acetic acid, plus adjuvants |
| T16, Control 1 | | | None | H20 + adjuvants |
| T16, Control 2 | | | None | H20 only |
| T22, S1 | Example 6, FIG. 3 | Greenhouse trial. | Potassium (K) | K-acetate + succinic acid, plus adjuvants |
| T22, S2 | Example 6, FIG. 3 | | " | |
| T22, Control 1 | Example 6, FIG. 3 | | None | H20 + adjuvants |
| T30, S-1 | | Greenhouse trial. | " | K-acetate + citric acid, plus adjuvants |
| T30, S-2 | | | " | K-acetate + citric acid, plus adjuvants |
| T30, S-3 | | | " | K-acetate + citric acid, plus adjuvants |

TABLE 6A-continued

Summary of trial results (part I)

| Trial #, Sample # | Ref. to Example # and Figure # | Notes | Active Nutrient | Solution Formulation |
|---|---|---|---|---|
| T30, S-4 | | | " | K-acetate + citric acid, plus adjuvants |
| T30, S-5 | | | " | K-acetate + citric acid, plus adjuvants |
| T30, S6 | | | " | K-acetate + citric acid, plus adjuvants |
| T30, Control 1 | | | None | H20 + adjuvants |
| T30, Control 2 | | | None | H20 + adjuvants |
| T31-A, S-1. Test 31 solutions split for 31 A & 31 B | Example 5, FIG. 4A | Greenhouse trial. Tests 31-A and 31-B have same actives, diff. adjuvants | Potassium (K) | K-acetate + citric acid, plus adjuvants |
| T31-A, S-2 | Example 5, FIG. 4A | | | K-acetate + citric acid, plus adjuvants |
| T31-A, S-3 | Example 5, FIG, 4A | | | K-acetate + citric acid, plus adjuvants |
| T31-A, Control "A" | Example 5, FIG. 4A | | | H20 + adjuvants |
| T31-B, S-1 | Example 5, FIG. 4B | Greenhouse trial. Tests 31-A and 31-B have same actives, diff. adjuvants | Potassium (K) | K-acetate + citric acid in sol'n plus adjuvants |
| T31-B, S-2 | Example 5, FIG. 4B | | | K-acetate + citric acid in sol'n plus adjuvants |
| T31-B, S-3 | Example 5, FIG. 4B | | | K-acetate + citric acid in sol'n plus adjuvants |
| T31-B, Control "B" | Example 5, FIG. 4B | | | H20 + adjuvants |
| T32-A, S-1 Test 32 solutions split for 32 A & 32 B | | Greenhouse trial. Tests 32-A and 3B-B have same actives, diff. adjuvants | Potassium (K) | K-acetate + citric acid in sol'n plus adjuvants |
| T32-A, S-2 | | | | K-acetate + citric acid in sol'n plus adjuvants |
| T32-A, S-3 | | | | K-acetate + citric acid in sol'n plus adjuvants |
| T32-A, Control "A" | | | | H20 + adjuvants |
| T32-B, S-1 | | Greenhouse trial. Tests 32-A and 3B-B have same actives, diff. adjuvants | Potassium (K) | K-acetate + citric acid in sol'n plus adjuvants |
| T32-B, S-2 | | | | K-acetate + citric acid in sol'n plus adjuvants |
| T32-B, S-3 | | | | K-acetate + citric acid in sol'n plus adjuvants |
| T32-B, Control "B" | | | | H20 + adjuvants |
| T41-A, S-1 | Example 8, FIG. 5 | Greenhouse trial. Tests 41-A and 41-B have same actives, diff. adjuvants | Nitrogen | Ammonium sulfate + adjuvants |
| T41-A, S-1 Control | Example 8, FIG. 5 | | | H20 + adjuvants |
| 41-B, S-2 | Example 8, FIG. 5 | Greenhouse trial. Tests 41-A and 41-B have same actives, diff. adjuvants | Nitrogen | Ammonium sulfate + adjuvants incl. MSO |
| T41-B, S-2 Control | Example 8, FIG. 5 | | | H20 + adjuvants |

TABLE 6A-continued

Summary of trial results (part I)

Figure 12:
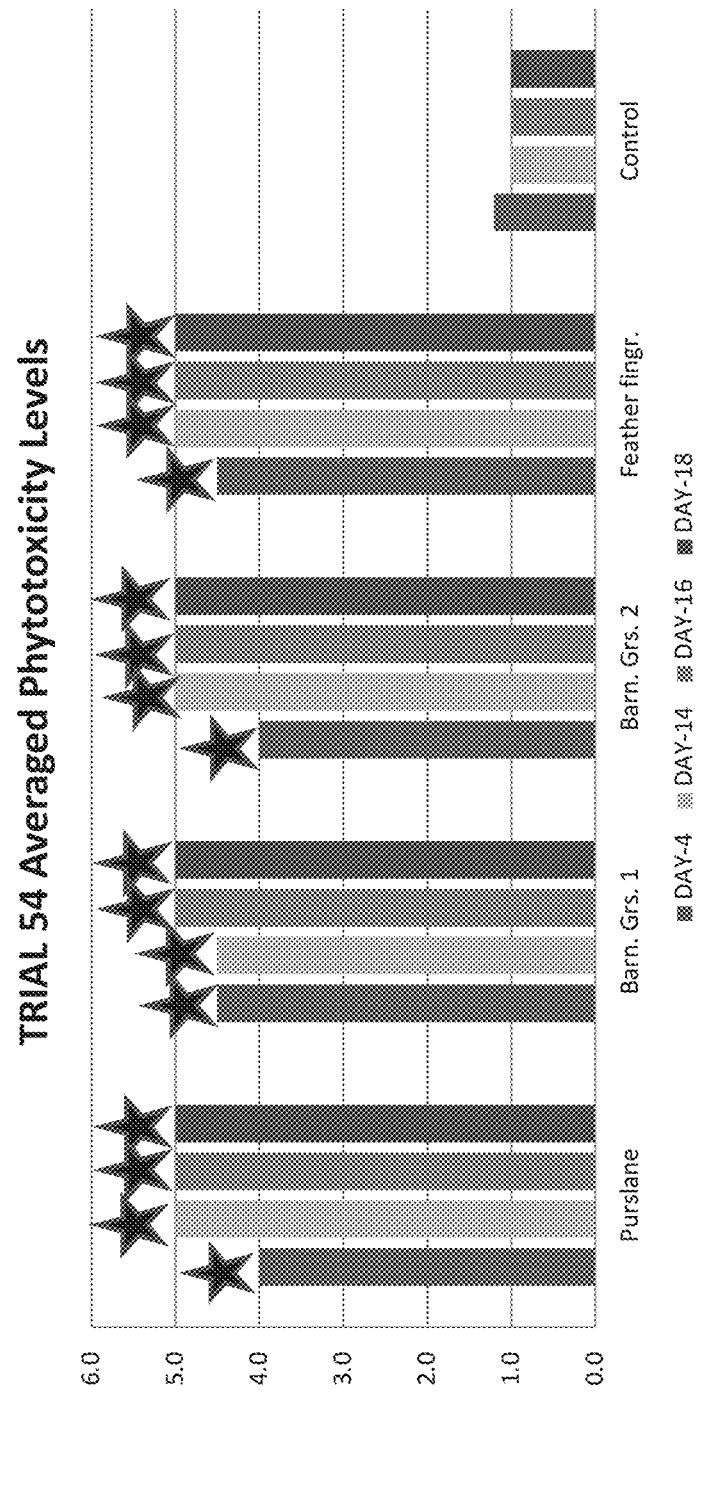
FIG. 12 is a graph showing the average toxicity scores for the plants tested in Trial 54 in which the herbicide was K-acetate; molarity 2.0, proprietary adjuvant mix. Results of Trial 54: 2.5 molar solution yielded excellent phytotoxic control of all weeds of between 4.0 to 5.0 at Day 14 through Day 18, the conclusion of the test. At Day 4 strong to excellent phytotoxic control of the weeds was observed.
Figure 13:
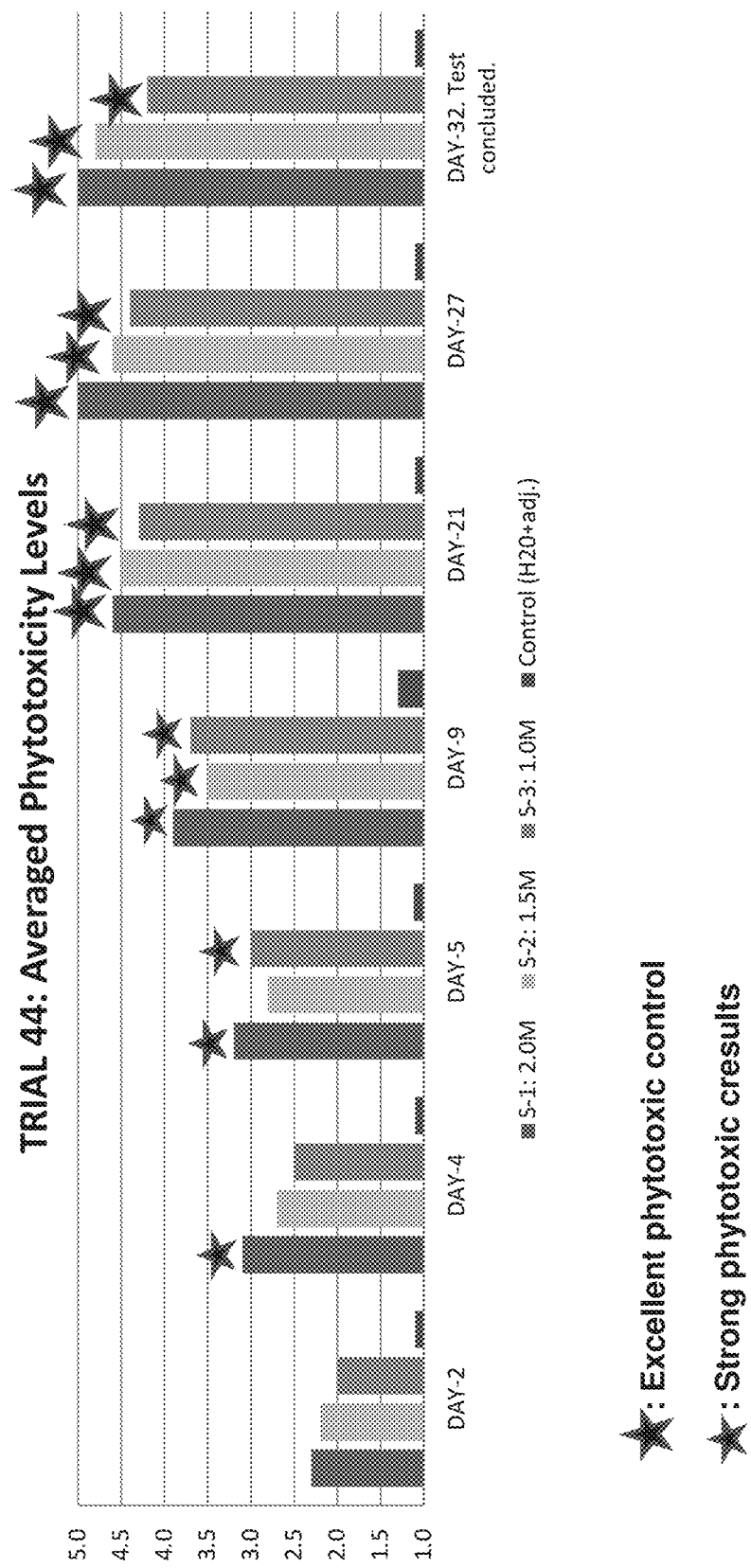
FIG. 13 is a graph showing the average toxicity scores for the plants tested in Trial 44 in which the herbicide was $ZnSO_4$; molarity 2.0, 1.5, 1.0; proprietary adjuvant mix. Results of Trial 44: 2.0 molar solution yielded strong control of 3.9 at Day 9, and excellent control of 4.6 through 5.0 at Day 21 through Day 32. 1.5 and 1.0 molar solutions yielded excellent controls of approximately 4.5 each at Day 21 through Day 32, the conclusion of test.

| Trial #, Sample # | Ref. to Example # and Figure # | Notes | Active Nutrient | Solution Formulation |
|---|---|---|---|---|
| T44, S-1 | Example 18, FIG. 13 | | Zinc | ZnSO4 |
| T44, S-2 | Example 8, FIG. 5 | | " | " |
| T44, S-3 | Example 8, FIG. 5 | | " | " |
| T44, Control | Example 8, FIG. 5 | | None | None |
| T47, S-1 | Example 14, FIG. 8 | | Potassium (K) | K-acetate + glacial acetic acid plus adjuvants |
| T47, S-2 | Example 14, FIG. 8 | | " | K-acetate + glacial acetic acid plus adjuvants |
| T47, S-3 | Example 14, FIG. 8 | | " | K-acetate + glacial acetic acid plus adjuvants |
| T47, S-4 | Example 14, FIG. 8 | | " | K-acetate + glacial acetic acid plus adjuvants |
| Control | Example 14, FIG. 8 | | " | K-acetate + glacial acetic acid plus adjuvants |
| T50, S-1 | Example 19, FIG. 11 | Field test on mature weeds. | Potassium (K) | K-acetate + citric acid, plus adjuvants |
| T50, S-2 | Example 19, FIG. 11 | | " | K-acetate + citric acid, plus adjuvants |
| T50, S-3 | Example 19, FIG. 11 | | " | K-acetate + citric acid, plus adjuvants |
| T50, S-4 Control 1 | Example 19, FIG. 11 | | " | K-acetate + citric acid, plus adjuvants |
| T50, S-5 Control 2 | Example 19, FIG. 11 | | None | None |
| T54. Purslane | Example 20, FIG. 12 | Greenhouse trial. | Potassium (K) | K-acetate + citric acid |
| T54. Bnyrd grass 1 | Example 20, FIG. 12 | | " | " |
| T54. Brnyrd grass 2 | Example 20, FIG. 12 | | " | " |
| T54, Feather fingergrass | Example 20, FIG. 12 | | " | " |
| T54. Control | Example 20, FIG. 12 | | None | None |
| T56, S-1 | Example 16, FIG. 10 | Greenhouse trial. | Potassium (K) | K-acetate + citric acid, plus adjuvants |
| T56, Control | Example 20, FIG. 12 | | None | None |
| T64, S-2 | Example 17, FIG. 14 | Greenhouse trial. | Boron (B) | Disodium octaborate tetrahydrate |
| T64, Control | Example 17, FIG. 14 | | " | None |

TABLE 6B

Summary of trial results (part II)

| Trial #, Sample # | Adjuvants | Active Nutrient: M-Mass/Trial Molarity | Acid Added/L | Solution pH | Days Post Application/ Ave Score. BOLD indicates excellent phytotoxic control (e.g., "severe" or "killed" test plants) | Plant Species in Trial |
|---|---|---|---|---|---|---|
| T6, S1 | Buffer-PS | 306.395; 2.1 | 0.0 | 7.73 | 11/4.3; 22/4.0 (end) | 21, 22, 26, 19, 3, 14 |
| T6, Control 1 | None | None | None | est. 6.5 | 11/1.0 (end) | 21, 22, 26, 19, 3, 14 |
| T7, S2 | Widespread | 306.395; 1.0 | 0.0 | 7.75 | 10/4.2; 20/4.8 (end) | 21, 22, 3, 19, 14, 24 |
| T7, Control 1 | None | None | None | 7.62 | 10/1.0; 20/1.0 (end) | 21, 22, 3, 19, 14, 24 |
| T7, Control 2 | Widespread | None | None | 6.36 | 10/2.3; 20/NR (end) | 21, 22, 3, 19, 14, 24 |
| T13, S1 | Widespread and MSO | 306.395; 1.5 | 345 g | 5.91 | 11/4.3 (end) | 21, 7, 10 |

TABLE 6B-continued

Summary of trial results (part II)

| Trial #, Sample # | Adjuvants | Active Nutrient: M-Mass/Trial Molarity | Acid Added/L | Solution pH | Days Post Application/ Ave Score. BOLD indicates excellent phytotoxic control (e.g., "severe" or "killed" test plants) | Plant Species in Trial |
|---|---|---|---|---|---|---|
| T13, S2 | Widespread and MSO | 306.395; 1.0 | NR | 5.90 | 11/4.0 (end) | 21, 7, 10 |
| T13, Control | Widespread and MSO | None | None | NR | 13/1.0 (end) | 21, 7, 10 |
| T14, S1 | Urea and Widespread | 98.14; 2.0 | 100 ml | 5.28 | 1/4.0; 2/4.0; 4/4.0; 7/5.0; 11/4.7; 15/4.8; 22/4.8 (end) | 21, 22, 10 |
| T14, S2 | Urea and Widespread | 98.14; 1.5 | 128 ml | 5.29 | 1/4.0; 2/4.7; 4/4.0; 7/5.0; 11/4.8; 15/4.8; 22/5.0 (end) | 21, 22, 10 |
| T14, S3 | Urea and Widespread | 98; 1.0 | 64 ml | 5.29 | 2/4.3; 4/4.7; 7/4.5; 11/4.0; 15/4.2; 22/3.7 (end) | 21, 22, 10 |
| T14, Control 1 | Urea and Widespread | None | None | NR | 1/1.0; 2/1.0; 7/1.3; 11/1.3; 15/1.0; 22/1.0 (end) | 21, 22, 10 |
| T14, Control 2 | None | None | None | NR | 1/1.0; 2/1.0; 7/1.0; 11/1.0; 15/1.0; 22/1.0 (end) | 21, 22, 10 |
| T15, S1 | Urea, Widespread and MSO | 98.14; 2.0 | 200 ml | est'd 5.28 | 1/4.0; 2/4.0; 9/4.7; 10/4.7; 22/5.0 (end) | 21, 22, 10 |
| T15, S2 | Urea, Widespread and MSO | 98.14; 1.5 | 100 ml | est'd 5.29 | 2/4.0; 9/4.3; 22/4.7 (end) | 21, 22, 10 |
| T15, S3 | Urea, Widespread and MSO | 98.14; 1.0 | 64 ml | est'd 5.29 | 2/4.2; 9/3.7; 22/4.0 (end) | 21, 22, 10 |
| T15, Control 1 | Urea, Widespread and MSO | None | None | NR | 2/3.3; 9/1.0; 22/1.0 (end) | 21, 22, 10 |
| T15, Control 2 | None | None | None | NR | 2/1.0; 9/1.0; 22/1.0 (end) | 21, 22, 10 |
| T16, S1 | Urea + MSO | 98.14; 2.0 | 200 ml | est'd 5.28 | 2/4.0; 5/4.7; 8/4.7; 20/4.3; 33/4.3 (end) | 21, 10, 12 |
| T16, S2 | " | 147; 1.5 | 128 ml | est'd 5.29 | 2/3.7; 5/4.7; 8/4.3; 20/4.7; 33/4.7 (end) | 21, 10, 12 |
| T16, Control 1 | " | None | None | NR | 5/1.0; 8/1.0; 20/1.0; 33/NR (end) | 21, 10, 12 |
| T16, Control 2 | None | None | None | NR | 5/1.0; 8/1.0; 20/1.0; 33/NR (end) | 21, 10, 12 |
| T22, S1 | Urea + Widespread | 98.14; 2.0 | 66 g | 5.01 | 1/3.0; 2/3.5; 4/3.9; 5/4.3; 7/4.4 (end) | 22, 15, 13, 19 |
| T22, S2 | Urea + Widespread | 98.14; 2.0 | 40 g | 5.01 (est'd) | 1/3.0; 2/3.3; 5/4.1; 4/3.3; 5/4.1; 7/4.1 (end) | 22, 15, 13, 19 |
| T22, Control 1 | Urea + Widespread | None | None | NR | 1/1.0; 2/1.0; 4/1.0; 5/1.0; 7/1.0 (end) | 22, 15, 13, 19 |
| T30, S-1 | Urea + Widespread | 98.14; 2.0 | 150 g | 4.05 | ` | 21, 4, 16, 11 |
| T30, S-2 | Urea + Widespread | 98.14; 1.5 | NR | 4.02 | 1/3.7; 3/3.6; 5/4.0 (end) | 21, 4, 16, 11 |
| T30, S-3 | Urea + Widespread | 98.14; 1.0 | 70 g | 4.02 | 1/3.5; 3/3.6; 5/4.0 (end) | 21, 4, 16, 11 |
| T30, S-4 | Urea + Widespread | 98.14; 2.0 | 1 g | 6.98 | 1/3.4; 3/3.4; 4/4.3 (end) | 21, 4, 16, 11 |
| T30, S-5 | Urea + Widespread | 98.14; 1.5 | 0.5 g | 6.80 | 1/3.4; 3/3.3; 5/3.4 (end) | 21, 4, 16, 11 |
| T30, S6 | Urea + Widespread | 98.14; 1.0 | <0.5 g | 7.03 | 1/3.0; 3.0; 5/3.0 (end) | 21, 4, 16, 11 |

TABLE 6B-continued

Summary of trial results (part II)

| Trial #, Sample # | Adjuvants | Active Nutrient: M-Mass/Trial Molarity | Acid Added/L | Solution pH | Days Post Application/ Ave Score. BOLD indicates excellent phytotoxic control (e.g., "severe" or "killed" test plants) | Plant Species in Trial |
|---|---|---|---|---|---|---|
| T30, Control 1 | Urea + Widespread | None | None | 4.00 | 1/1.0; 3/1.0; 5/1.0 (end) | 21, 4, 16, 11 |
| T30, Control 2 | Urea + Widespread | None | None | 7.00 | 1/1.0; 3/1.0; 5/1.0 (end) | 21, 4, 16, 11 |
| T31-A, S-1. Test 31 solutions split for 31 A & 31 B | Urea + Widespread | 98.14; 2.0 | 50 g | 5.01 | 1/3.6; 2/3.6; 3/3.8; 6/4.1; 8/3.8; 31/4.1 (end) | 2, 5, 23, 16, 22 |
| T31-A, S-2 | Urea + Widespread | 98.14; 1.5 | 29.5 g | 5.00 | 1/3.4; 2/3.6; 3/3.6; 6/3.9; 8/3.7; 30/3.9 (end) | 2, 5, 23, 16, 22 |
| T31-A, S-3 | Urea + Widespread | 98.14; 1.0 | 25.0 g | 4.97 | 1/3.2; 2/3.3; 3/3.4; 4/3.5; 8/3.2; 30/4.0 (end) | 2, 5, 23, 16, 22 |
| T31-A, Control "A" | Urea + Widespread | 0; 0 | 24 g | 5.00 | 1/1.1; 2/1.3; 3/1.0; 6/NR; 8/NR; 30/NR (end) Note: Onion (Plant "2") in Tests 31 A & B was only slightly affected by the formula; all other plants were severely effected or killed. | 2, 5, 23, 16, 22 |
| T31-B, S-1 | Urea + LI-700 | 98.14; 2.0 | 29.5 g | 5.01 | 1/3.5; 2/3.8; 3/4.0; 4/4.2; 8/4.3; 30/4.3 (end) | 2, 5, 23, 16, 22 |
| T31-B, S-2 | Urea + LI-700 | 98.14; 1.5 | 25.0 g | 4.97 | 1/3.5; 2/3.6; 3/3.5; 4/4.1; 8/4.4; 30/4.4 (end) | 2, 5, 23, 16, 22 |
| T31-B, S-3 | Urea + LI-700 | 98.14; 1.0 | 24 g | 5.00 | 1/3.1; 2/3.4; 3/3.4; 4/3.7; 8/3.6; 30/2.7 (end) | 2, 5, 23, 16, 22 |
| T31-B, Control "B" | Urea + LI-700 | 0; 0 | 24 g | 5.00 | 1/1.1; 2/1.3; 3/1.0; 6/NR; 8/NR; 30/NR (end) Note: Onion (Plant #2) in Tests 31 A & B was only slightly affected by the formula; al other plants were severely effected or killed. | 2, 5, 23, 16, 22 |
| T32-A, S-1 Test 32 solutions split for 32 A & 32 B | Urea + Widespread less than Test 31A | 98.14; 2.0 | 50 g | 5.01 (est'd) | 3/3.7; 5/4.3; 9/4.5; 15/4.5 (end) | 18, 17, 6, 2, 22 |
| T32-A, S-2 | Urea + Widespread less than Test 31A | 98.14; 1.5 | 29.5 g | 5.00 (est'd) | 3/3.7; 5/4.3; 9/4.6; 15/4.6 (end) | 18, 17, 6, 2, 22 |
| T32-A, S-3 | Urea + Widespread less than Test 31A | 98.14; 1.0 | 25.0 g | 4.97 (est'd) | 3/3.5; 5/3.9; 9/4.3; 15/4.4 (end) | 18, 17, 6, 2, 22 |

TABLE 6B-continued

Summary of trial results (part II)

| Trial #, Sample # | Adjuvants | Active Nutrient: M-Mass/Trial Molarity | Acid Added/L | Solution pH | Days Post Application/ Ave Score. BOLD indicates excellent phytotoxic control (e.g., "severe" or "killed" test plants) | Plant Species in Trial |
|---|---|---|---|---|---|---|
| T32-A, Control "A" | Urea + Widespread less than Test 31A | 0; 0 | 24 g | NR | 3/1.0; 5/NR; 9/NR; 15/NR (end) | 18, 17, 6, 2, 22 |
| T32-B, S-1 | Urea + LI-700 less than Test 31B | 98.14; 2.0 | 50 g | 5.01 (est'd) | 3/3.7; 5/4.1; 9/4.2; 15/4.1 (end) | 18, 17, 6, 2, 22 |
| T32-B, S-2 | Urea + LI-700 less than Test 31B | 98.14; 1.5 | 29.5 g | 5.00 test'd) | 3/3.7; 5/4.4; 9/4.6; 15/4.6 (end) | 18, 17, 6, 2, 22 |
| T32-B, S-3 | Urea + LI-700 less than Test 31B | 98.14; 1.0 | 25.0 g | 4.97 (est'd) | 3/3.8; 5/4.0; 9/4.3; 15/4.4 (end) | 18, 17, 6, 2, 22 |
| T32-B, Control "B" | Urea + LI-700 less than Test 31B | 0; 0 | 24 g | NR | 3/1.0; 5/NR; 9/NR; 15/NR (end) | 18, 17, 6, 2, 22 |
| T41-A, S-1 | Widespread | 132.14; 2.0 | 0.0 | 5.50 | Monocots: 3/3.0; 7/2.5; 12/3.0, 18/2.5, 23/2.3 (end) Dicots: 3/4.0; 7/4.0; 12/4.3; 18/4.3; 23/5.0 (end) Note: Dicots killed, monocots not. | 2, 22, 10, 3 |
| T41-A, S-1 Control | MSO only | 0; 0 | 0.0 | 7.80 | Mono. and Dicot.: 3/1.0; 7/1.0; 12/1.0; 18/1.0; 23/1.0 (end) | 2, 22, 10, 3 |
| 41-B, S-2 | Widespread + MSO | 264; 2.0 | 0.0 | 5.50 | Monocots: 3/3.0; 7/2.8; 12/3.0, 18/2.5, 23/2.3 (end) Dicots: 3/4.0; 7/4.0; 12/4.3, 18/4.5; 23/5.0 (end) Note: Dicots killed, monocots not. | 2, 22, 10, 3 |
| T41-B, S-2 Control | MSO only | 0; 0 | 0.0 | NR | Mono. and Dicot.: 3/1.0; 7/1.0; 12/1.0; 18/1.0; 23/1.0 (end) | 2, 22, 10, 3 |
| T44, S-1 | Widespread + MSO | 179.47; 2.0 | 0.0 | 5.10 | 2/2.3; 4/3.1; 5/3.2; 9/3.9; 21/4.6; 27/5.0; 32/5.0 (end) | 6-A, 11-B, 21, 23-B |
| T44, S-2 | Widespread + MSO | 67; 1.5 | 0.0 | 5.46 | 2/2.7; 4/3.0; 5/2.8; 9/3.5; 21/4.5; 27/4.6; 32/4.8 (end) | 6-A, 11-B, 21, 23-A |
| T44, S-3 | Widespread + MSO | 45; 1.0 | 0.0 | 5.64 | 2/2.0; 4/2.5; 5/3.0; 9/3.7; 21/4.3; 27/4.4; 32/4.2 (end) | 6-A, 11-B, 21, 23-A |
| T44, Control | Widespread + MSO | 0.0 | 0.0 | NR | 2/1.0; 4/1.0; 5/1.3; 9/1.3; 21/1.0; 27/1.0; 32/1.0 (end) | 6-A, 11-B, 21, 23-A |
| T47, S-1 | Widespread + MSO | 98; 2.5 | 35.0 | 5.04 | 2/3.8; 5/4.5; 9/4.8; 14/4.9 (end) | 5, 11b, 13, 22b, 23b, |

TABLE 6B-continued

Summary of trial results (part II)

| Trial #, Sample # | Adjuvants | Active Nutrient: M-Mass/Trial Molarity | Acid Added/L | Solution pH | Days Post Application/ Ave Score. BOLD indicates excellent phytotoxic control (e.g., "severe" or "killed" test plants) | Plant Species in Trial |
|---|---|---|---|---|---|---|
| T47, S-2 | Widespread + MSO | 98; 2.0 | 25.0 g | 5.05 | 2/3.7; 5/4.0; 9/4.8; 14/4.8 (end) | 5, 11b, 13, 22b, 23 b, |
| T47, S-3 | Widespread + MSO | 98; 1.5 | 18.0 | 5.03 | 2/3.6; 5/4.5; 9/4.8; 14/5.0 (end) | 5, 11b, 13, 22b, 23b, |
| T47, S-4 | Widespread + MSO | 98; 1.0 | <18 | 5.07 | 2/3.7; 5/4.4; 9/4.8; 14/4.8 (end) | 5, 11b, 13, 22b, 23b, |
| Control | Widespread + MSO | 0.0 | 0.0 | 7.04 | 2/1.0; 5/1.0; 9/1.0; 14/1.0 (end) | 5, 11b, 13, 22b, 23b, |
| T50, S-1 | Canola oil and "Joy" detergent | 98.14; 2.5 | 300 g | 5.00 | 3/2.8; 10/2.8 (end) | Mature field weeds |
| T50, S-2 | Canola oil and "Joy" detergent | 98.14; 2.0 | 300 g | 5.00 | 3/3.6; 10/3.6 (end) | Mature field weeds |
| T50, S-3 | Canola oil and "Joy" detergent | 98.14; 1.5 | 300 g | 5.00 | 3/3.5; 10/3.4 (end) | Mature field weeds |
| T50, S-4 Control 1 | Canola oil and "Joy" detergent | 0; 0 | 0.0 | 7.00 | 3/0.1; 10/0.4 (end) | Mature field weeds |
| T50, S-5 Control 2 | None | 0; 0 | 0.0 | 7.00 | 3/0.1; 10/0.1(end) | Mature field weeds |
| T54. Purslane | Kinetic, DyneAmic, UAN | 98.14; 2.0 | 29 g | 5.04 | 4/4.0; 14/5.0; 16/5.0; 18/5.0 (end) | 23A |
| T54. Brnyrd grass 1 | Kinetic, DyneAmic, UAN | " | " | " | 4/4.5; 14/4.5; 16/5.0; 18/5.0 (end) | 11C |
| T54. Brnyrd grass 2 | Kinetic, DyneAmic, UAN | " | " | " | 4/4.0; 14/5.0; 16/5.0; 18/5.0 (end) | 11C |
| T54. Feather fingergrass | Kinetic, DyneAmic, UAN | " | " | " | 4/4.5; 14/5.0; 16/5.0; 18/5.0 (end) | 9A |
| T54. Control | Kinetic, DyneAmic, UAN | 0; 0 | 0; 0 | | 4/1.0; 14/1.0; 16/1.0; 18/1.0 (end) | 23A, 11C, 9A |
| T56, S-1 | Kinetic, urea, and humectant (sucrose) | 98.14; 1.5 | 34 g | 5.52 | 3/3.9; 4/4.0; 7/4.3; 10/4.8; 12/5.0; 15/5.0 (end) | 26, 3, 10, 17A |
| T56, Control | None | 0; 0 | 0.0 | NR | 3/1.1; 4/1.1; 7/1.1; 10/1.1; 12/1.1; 15/1.1 (end) | 26, 3, 10, 17A |
| T64, S-2 | Kinetic, urea, sucrose | 412.5; 0.5 | 0.0 | est'd 7.78 | 12/4.3; 34/4.6 | 5, 18a, 22, 23b, 26 |
| T64, Control | Kinetic, urea, sucrose | 0; 0 | 0.0 | est'd 7.0 | 12/1.0; 34/1.0 | 5, 18a, 22, 23b, 26 |

The observed effects of Trial 32A were both short-term with complete burn-down of tissues above-ground several days following application of the herbicide, and long-term with virtually no recovery of the treated plants from roots presumably killed as well by the foliar application of the herbicide.

Example 2

Summary of Toxicity Scores for Trials

Table 7 summarizes only those tests that produced excellent phytotoxic effects of 4.0 to 5.0. Trials using formulations that did not produce the desired effects are not presented in Table 7, nor are results within a specific trial using molarities too weak to produce an herbicidal effect. Interpretation of the information in Table 7 would be as follows, using the data stream for Trial 14 on that table as an example.

For example, Trial Number 14 (see Example for additional details) examined the effects of herbicides that comprised K-acetate; molarity 2.0 ("T14, S1"), 1.5 ("T14, S2"), 1.0 ("T14, S3"); pH approx. 5.3 by glacial acetic acid, and a proprietary adjuvant mix. Shown are the average toxicity scores for the three plants tested in Trial 14 (21,22,10 corresponding to Pasture Blend 1 and 2 and *Cineraria meritima* (Dusty miller "Silver Dust") (ref. Tables 4A and 4B) (See also Example 4; Table 9; and FIG. 2). S-1 corresponds to the highest concentration of active nutrient tested, S-3 corresponds to the lowest concentration of nutrient tested and S-2 represents an intermediate level. The column "Days Post Application/Ave. Score" presents the toxicities at 7, 11, 15 and 22 days after application of the herbicide solution S-1, S-2, S-3, and two controls.

TABLE 7

Results and summary of score at test completion

| Trial Number, Sample # | Active Component and Acidifier | Days Post Application/ Ave. Score |
|---|---|---|
| T6, S1 | K-citrate only | 11/4.3; 22/4.0 (end) |
| T6, Control 1 | H20 + adjuvants | 11/1.0 (end) |
| T6, Control 2 | H20 only | 11/1.0 (end) |
| T7, S2 | K-citrate | 10/4.2; 20/4.8 (end) |
| T7, Control 1 | H20 + adjuvants | 10/1.0; 20/1.0 (end) |
| T7, Control 2 | H20 only | 10/2.3; 20/NR (end) |
| T13, S1 | K-citrate + citric acid as freeze-dried lemon juice | 13/4.3 (end) |
| T13, S2 | K-citrate + citric acid as freeze-dried lemon juice | 13/4.0 (end) |
| T13, Control | H20 + adjuvants | |
| T14, S1 | K-acetate + glacial acetic acid | 7/5.0; 11/4.7; 15/4.8; 22/4.8 (end) |
| T14, S2 | K-acetate + glacial acetic acid | 7/5.0; 11/4.8; 15/4.8; 22/5.0 (end) |
| T14, S3 | K-acetate + glacial acetic acid | 7/4.5; 11/4.0; 22/3.7 (end) |
| T14, Control 1 | H20 + adjuvants | 7/1.3; 11/1.3; 15/1.0; 22/1.0 (end) |
| T14, Control 2 | H20 only | 7/1.0; 11/1.0; 15/1.0; 22/1.0 (end) |
| T15, S1 | K-acetate + glacial acetic acid | 2/4.0; 8/4.7; 10/4.7; 22/5.0 (end) |
| T15, S2 | K-acetate + glacial acetic acid | 2/4.0; 9/4.7; 22/4.7 (end) |
| T15, S3 | K-acetate + glacial acetic acid | 2/4.2; 9/4.3; 22/4.0 (end) |
| T15, Control 1 | H20 + adjuvants | 2/1.0; 9/1.0; 22/1.0 (end) |
| T15, Control 2 | H20 only | 2/1.0; 9/1.0; 22/1.0 (end) |
| T16, S1 | K-acetate + glacial acetic acid | 5/4.7; 8/4.7; 20/4.3; 33/4.3 (end) |
| T16, S2 | K-acetate + glacial acetic acid | 5/4.7; 8/4.3; 20/4.7; 33/4.7 (end) |
| T16, Control 1 | H20 + adjuvants | 5/1.0; 8/1.0; 20/1.0; 33/NR (end) |
| T16, Control 2 | H20 only | 5/1.0; 8/1.0; 20/1.0; 33/NR (end) |
| T17, S1 | K-acetate + glacial acetic acid | 3/4.6; 4/4.6; 15/4,8; 28/4.6 (end) |
| T17, S2 | K-acetate + glacial acetic acid | 3/4.0; 15/4.6; 28/4.6 (end) |
| T17, S3 | K-acetate + glacial acetic acid | 3/4.1; 15/4.5; 28/4.6 (end) |
| T17, Control 1 | H20 + adjuvants | 3/1.0; 15/1.0; 28/1.0 (end) |
| T17, Control 2 | H20 only | 3/1.0; 15/1.0; 28/1.0 (end) |
| T17, Control 3 | H20 + adjuvants | 3/1.0; 15/1.3; 28/1.0 (end) |
| T22, S1 | K-acetate + succinic acid | 1/3.0; 2/3.5; 4/3.9; 7/4.4 (end) |
| T22, S2 | K-acetate + succinic acid | 1/3.3; 2/3.3; 4/3.3; 7/4.1 (end) |
| T22, Control 1 | H20 + adjuvants | 1/1.0; 2/1.0; 4/1.0; 7/1.0; 17/1.0 (end) |
| T30, S1 | K-acetate + citric acid | 1/3.6; 3/3.6; 5/4.5 (end) |
| T30, S1 | K-acetate + citric acid | 1/3.7; 3/3.6; 5/4.0 (end) |
| T30, S1 | K-acetate + citric acid | 1/3.5; 3/3.6; 5/4.0 (end) |
| T30, Control 1 | H20 + adjuvants | 1/1.0; 3/1.0; 5/1.0 (end) |
| T31-A, S-1. Trial 31 solutions split for 31 A & 31 B | K-acetate + citric acid | 1/3.6; 2/3.6; 3/3.8; 6/4.1; 8/4.1; 30/4.1 (end) |
| T31-A, S-2 | K-acetate + citric acid | 1/3.4; 2/3.6; 3/3.6; 6/3.9; 8/3.7; 30/4.1 (end.) |
| T31-A, S-3 | K-acetate + citric acid | 1/3.2; 2/3.3; 3/3.4; 4/3.5; 8/3.8; 30/4.0 (end) |
| T31-A, Control "A" | H20 + adjuvants #1 | 1/1.1; 2/1.3; 3/1.0; 6/NR; 8/NR; 30/NR (end) |
| T31-B, S-1 | K-acetate + citric acid | 1/3.5; 2/3.8; 3/4.0; 4/4.2; 8/4.3; 30/4.3 (end) |
| T31-B, S-2 | K-acetate + citric acid | 1/3.5; 2/3.6; 3/3.5; 4/4.1; 8/4.4; 30/4.4 (end) |
| T31-B, S-3 | K-acetate + citric acid | 1/3.1; 2/3.4; 3/3.4; 4/3.7; 8/3.6; 30/3.0 (end) |

TABLE 7-continued

Results and summary of score at test completion

| Trial Number, Sample # | Active Component and Acidifier | Days Post Application/ Ave. Score |
|---|---|---|
| T31-B, Control "B" | H20 + adjuvants #2 | 1/1.1; 2/1.3; 3/1.0; 6/NR; 8/NR; 30/NR(end) |
| T32-A, S-1 Trial 32 solutions split for 32 A & 32 B | K-acetate + citric acid | 3/3.7; 5/4.3; 9/4.5; 15/4.5 (end test) |
| T32-A, S-2 | K-acetate + citric acid | 3/3.7; 5/4.3; 9/4.6; 15/4.6 (end test) |
| T32-A, S-3 | K-acetate + citric acid | 3/3.5; 5/3.9; 9/9/4.3; 15/4.4 (end test) |
| T32-A, Control "A" | H20 + adjuvants #1 | 3/1.0; 5/NR; 9/NR; 15/NR (end test) |
| T32-B, S-1 | K-acetate + citric acid | 3/3.7; 5/4.1; 9/4.2; 15/4.1 (end test) |
| T32-B, S-2 | K-acetate + citric acid | 3/3.7; 5/4.4; 9/4.6; 15/4.6 (end test) |
| T32-B, S-3 | K-acetate + citric acid | 3/3.8; 5/4.0; 9/4.3; 15/4.4 (end test) |
| T32-B, Control "B" | H20 + adjuvants #2 | 3/1.0; 5/NR; 9/NR; 15/NR (end test) |
| 41-A, S-1 | Ammonium sulfate | 3/2.8; 7/3.5; 12/3.5, 18/3.4, 23/3.6 (end) |
| T41-A, S-1 Control | H20 + adjuvants #1 | 3/1.0; 7/1.0; |
| 41-B, S-2 | Ammonium sulfate | Monocots: 3/3.0; 7/2.8; 12/3.0, 18/2.5, 41./2.3 (end) Dicots: 3/3.0; 7/2.8; 12/3.0, 18/2.5, 41/2.3 (end) |
| T41-B, S-2 Control | H20 + adjuvants #2 | Mono. and Dicot.: 3/1.0; 7/1.0; 12/1.0; 1.8/1.0; 23/1.0 (end) |

Note:
Onion (Plant #2) in Trials 31 A & B was only slightly affected by the formula; all other plants were severely affected or killed.

Example 3

Trial 13 Results: K-Citrate+Citric Acid as Lemon Juice

In Trial 13, the herbicides comprised K-citrate and lemon juice. In particular, the herbicide was formulated with K-citrate; molarity 1.5, 1.0, 0.5; pH approx. 5.9 by freeze dried lemon juice; proprietary adjuvant mix. Ref. Lab-1, p. 109. Test plants (ref. Tables 4A and 4B): P 1, 7, 10. The results of Trial 13 are shown in FIG. 1 and Table 8.

TABLE 8

Trial 13 results by solution and molarity

| Herbicide Solution | DAY-2 | DAY-3 | DAY-9 | DAY-11 (ended) |
|---|---|---|---|---|
| S-1: 1.5M* | 3.3 | 3.0 | 3.8 | 4.3 |
| S-2: 1.0M* | 3.0 | 3.3 | 3.8 | 4.0 |
| S-3: 0.5M | 1.7 | 2.3 | 2.3 | 2.7 |
| Control (H2O) + adj. | 1.0 | 1.0 | 1.0 | 1.0 |

*Bold, italicized toxicity values indicate "severe-to-fatal" toxicity levels.

Results of Trial 13 (refer to FIG. 1): Excellent phytotoxic contact of 4.3 ("severe-to-fatal") resulted at Day 11 at a solution of 1.5M, and of 4.0 ("severe") at Day 11 at a solution of 1.0M. Controls showed no visible effect by Day 11 when test was concluded.

Example 4

Trial 14 Results: K-Acetate+Glacial Acetic Acid

In Trial 14, the herbicides comprised K-acetate; molarity 2.0, L5, 1.0; pH approx. 5.3 by glacial acetic acid, and a proprietary adjuvant mix. Ref. Lab-1, p. 113. Test plants (ref. Tables 4A and 4B): P1, P2, P10.

Table 9 and FIG. 2 show the average toxicity scores for the three plants tested in Trial 14 (21,22 [corresponding to Pasture Blend 1 and 2] and 10 Cineraria meritima (Dusty miller "Silver Dust"). S-1 corresponds to the highest concentration of active nutrient tested, S-3 corresponds to the lowest concentration of nutrient tested and S-2 represents an intermediate level.

TABLE 9

Trial 14 Post-application averaged toxicity scores (1-5)

| | DAY-1 | DAY-2 | DAY-7 | DAY-11 (ended) |
|---|---|---|---|---|
| S-1: 2.0M | 4.0 | 4.0 | 5.0 | 4.7** |
| S-2: 1.5M | 4.0 | 4.7 | 5.0 | 4.8** |
| S-3: 1.0M | 3.3 | 4.3 | 4.5 | 4.0** |
| Control | 1.0 | 1.0 | 1.0 | 1.0 |
| | DAY-1 | DAY-2 | DAY-7 | DAY-11 (ended) |

**Bold values indicate "severe-to-fatal" toxicity levels.

Results of Trial 14: As shown in FIG. 2 and Table 9, excellent phytotoxic effects of 4.0 and 4.7 ("severe-to-fatal") resulted at Day 1 and Day 11 at a solution concentration of 2.0M; of 4 and 4.8 at Day 1 and Day 11 at a concentration of 1.5M; and at 4.3 and 4.0 at Day 7 and Day 11 at a concentration of 1.0M. Controls sprayed with water and adjuvant mix only showed no effects.

Example 5

Trials 31A & B Results: K-Acetate+Citric Acid

In Trial 31A, the herbicides comprised K-acetate; molarity 2.0, 1.5, 1.0; pH approx. 5.0 by citric acid; proprietary adjuvant mix A. Ref. Lab-1, p. 195. Test plants (ref. Tables 4A and 4B): P2, 1, 5, 16, 23.

In Trial 31B, the herbicides comprised K-acetate; molarity 2.0, 1.5, 1.0; pH approx. 5.0 by citric acid; and proprietary adjuvant mix B. Ref. Lab-1, p. 195. Test plants (ref. Tables 4A and 4B): P2, 1, 5, 16, 23.

Figure 4A:
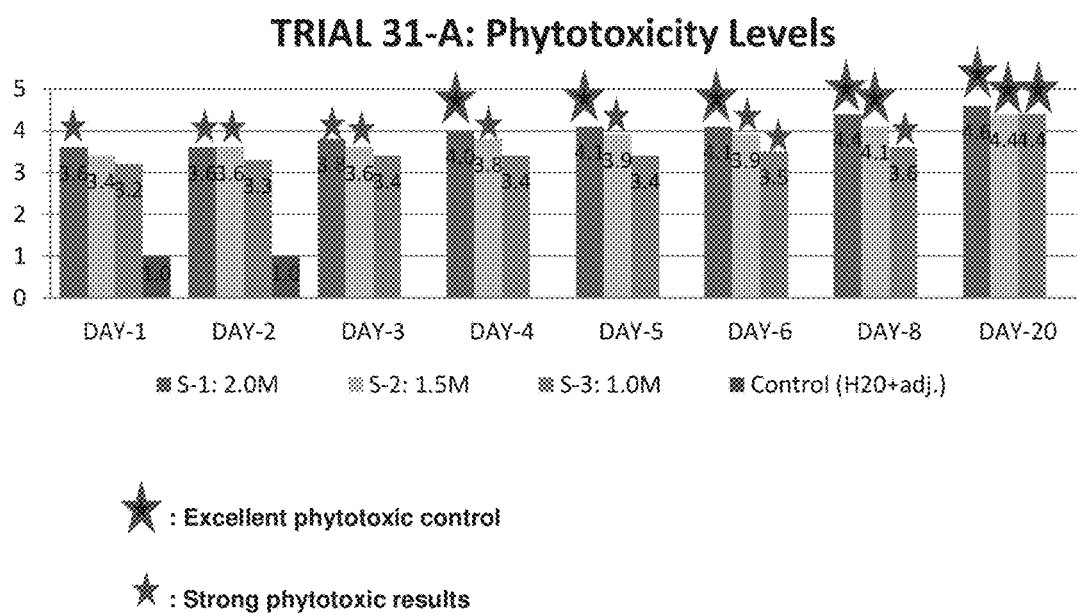
FIGS. 4A and 4B depict the average toxicity scores for the plants used in Trial 31A and Trial 31B, which tested an embodiment of an herbicide composition and method of using the same in both 31A and 31B. The plants were numbered 22, 1, 5, 16, and 23, corresponding to Pasture Blend 2, *Brassica oleracea* (var. Kale "Dinosaur"), *Lantana camara* (White Lantana), and *Pisum sativum* var. *saccharatum* (Snow pea) (Refer to Tables 4A and 4B for plant species identification). The only difference between Trials 31A and 31B was the composition of the proprietary adjuvant mix employed for each trial. The adjuvants for the "A" series were urea and WIDESPREAD silicone surfactant (Loveland Products). The adjuvants for the "B" series were urea and LI700 penetrant (Loveland Products). Solution 1 A & B (S-1A, S-1B) correspond to a 2.0 molar solution of potassium acetate, pH 5.01 achieved with citric acid. S-2 is a similar solution of 1.5 molarity, pH 5.00. S-3 is a similar solution of 1.0 molarity, pH 4.97. fur to Tables 6A and 6B for trial solutions, details and results). Results of Trial 31-A indicate excellent phytotoxic effects of from 4.0 to 4.6 ("severe-to-fatal") resulted at Day 4 through Day 20 at a solution concentration of 2.0M; of from 4.1 to 4.4 at Day 8 through Day 20 at a concentration of 1.5M; and at 4.4 by Day 20 at a solution concentration of 1.0M. Controls sprayed with water and adjuvant mixture were removed for laboratory analysis after Day 2, but showed no visible effects at that time. Results of Trial 31-B indicate excellent phytotoxicity levels of 4.2 to 4.6 ("severe-to-fatal") resulted at Day 6 through Day 20 at a solution concentration of 2.0M; of from 4.1 to 4.9 at Day 6 through Day 20 at a solution concentration of 1.5M; and of 4.0 through 4.1 at Day 8 through Day 20 at a solution concentration of 1.0M. Controls sprayed with a proprietary adjuvant mixture were removed for laboratory analysis after Day 2, but showed no visible effects at that time. Without being limited by theory, there appears to be little difference between the effectiveness of the two silicone surfactants compound in Trials 31A and 31B.
Figure 4B:
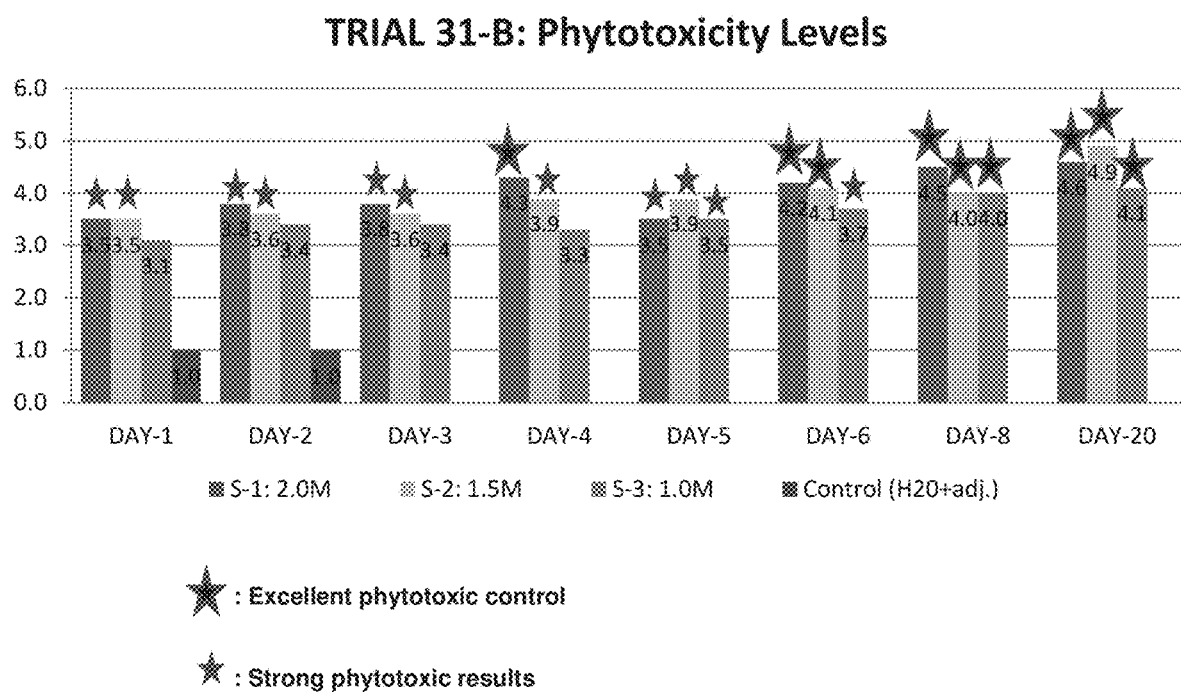

Table 10A and FIG. 4A show results for Trial 31A. Table 10B and FIG. 4B show results for Trial 31B, including average toxicity levels for 5 plants tested using potassium as the nutrient. As can be seen from the Table, at day 4, toxicity levels were severe-to-fatal for the highest concentration tested of 2.0 M. By day 8, all plants were at severe-to-fatal toxicity levels for all concentrations tested (1.0 to 2.0 M). These results are shown graphically in FIG. 2. Excellent toxicity levels of 4.2 to 4.6 ("severe-to-fatal") resulted at Day 6 through Day 20 at a solution concentration of 2.0M; of from 4.1 to 4.9 at Day 6 through Day 20 at a solution concentration of 1.5M; and of 4.0 through 4.1 at a solution concentration of 1.0M. Plants tested were Pasture Blend 2 (Tables 4A-B), *Allium ampeloprasum*, Leek "American Flag", *B. oleracea*, Kale "Dinosaur", *Lantana camara*, White, and *Pisum sativum* var. *saccharatum*, Snow pea.

Results of Trial 31A: Excellent phytotoxic control of from 4.0 to 4.6 ("severe-to-fatal") resulted at Day 4 through Day 20 at a solution concentration of 2.0M; of from 4.1 to 4.4 at Day 8 through Day 20 at a concentration of 1.5M; and at 4.4 by Day 20 at a solution concentration of 1.0M. Controls were removed for laboratory analysis after Day 2, but showed no visible effects at that time.

Results of Trial 31B: Excellent phytotoxic control of 4.2 to 4.6 ("severe-to-fatal") resulted at Day 6 through Day 20 at a solution concentration of 2.0M; of from 4.1 to 4.9 at Day 6 through Day 20 at a solution concentration of 1.5M; and of 4.0 through 4.1 at a solution concentration of 1.0M. Controls were removed for laboratory analysis after Day 2, but showed no visible effects at that time.

Example 6

Trial 22 K-Acetate+Succinic Acid

In Trial 22, the herbicides comprised K-acetate; molarity range 1.0-2.0; pH approx. 5.0 with succinic acid; proprietary adjuvant mix.

Table 11 shows the average toxicity scores for the three plants tested in Trial 22 (22,15,13, 19 corresponding to Pasture Blend 2, *Gazania rigens* ("Beda"), *Fragaria×ananassa* (Strawberry "Eversweet"), and *Nemophila menziesii discoidalis* (Baby blue eyes). S-1 corresponds to the highest concentration of active nutrient tested, S-3 corresponds to the lowest concentration of nutrient tested and S-2 represents an intermediate level. The data are graphically presented below in FIG. 3.

TABLE 10A

Trial 31A Post-Application Averaged Toxicity Levels (1-5)
Test plants (See Tables 4A and 4B): P2, 1, 5, 16, 23.

| Sample Molarity ↓ | DAY-1 | DAY-2 | DAY-3 | DAY-4 | DAY-5 | DAY-6 | DAY-8 | DAY-20 |
|---|---|---|---|---|---|---|---|---|
| S-1: 2.0M ** | 3.6 | 3.6 | 3.8 | *4.0* | *4.1* | *4.1* | *4.4* | *4.6* |
| S-2: 1.5M ** | 3.4 | 3.6 | 3.6 | 3.8 | 3.9 | 3.9 | *4.1* | *4.4* |
| S-3: 1.0M ** | 3.2 | 3.3 | 3.4 | 3.4 | 3.4 | 3.5 | 3.6 | *4.4* |
| Control (H20 + adj.)* | 1.0 | 1.0 | | | | | | |

*Controls and Samples 5-A and B removed for lab for analysis at Day 2.
** Bold, italicized toxicity values indicate "severe-to-fatal" toxicity levels.

TABLE 10B

Trial 31B Post-Application Averaged Toxicity Levels (1-5)
Test plants (See Tables 4A and 4B): P2, 1, 5, 16, 23.

| Sample Molarity ↓ | DAY-1 | DAY-2 | DAY-3 | DAY-4 | DAY-5 | DAY-6 | DAY-8 | DAY-20 |
|---|---|---|---|---|---|---|---|---|
| S-1: 2.0M ** | 3.5 | 3.8 | 3.8 | *4.3* | 3.5 | *4.2* | *4.5* | *4.6* |
| S-2: 1.5M ** | 3.5 | 3.6 | 3.6 | 3.9 | 3.9 | *4.1* | *4.0* | *4.9* |
| S-3: 1.0M ** | 3.1 | 3.4 | 3.4 | 3.3 | 3.5 | 3.7 | *4.0* | *4.1* |
| Control (H20 + adj.)* | 1.0 | 1.0 | | | | | | |

*Controls and Samples 5-A and B removed for lab for analysis at Day 2.
** Bold, italicized toxicity values indicate "severe-to-fatal" toxicity levels.

TABLE 11

Trial 22 Post-Application Averaged Toxicity Levels (1-5)
Test plants used were P2, 13, 15, 19 (Tables 4A-B)

| Composition Tested | DAY-1 | DAY-2 | DAY-3 | DAY-4 | DAY-5 | DAY-7 (ended) |
|---|---|---|---|---|---|---|
| S-1: 2.0M** | 3.0 | 3.5 | 3.9 | 3.9 | *4.3* | *4.4* |
| S-2: 1.5M** | 3.0 | 3.3 | 3.9 | 3.3 | *4.1* | *4.1* |
| S-3: 1.0M | 2.7 | 2.9 | 3.0 | 3.3 | 3.4 | 3.4 |
| Control | 1.0 | 1.0 | 1.0 | 1.0 | 1.0 | 1.0 |

**Bold, italicized toxicity values indicate "severe-to-fatal" toxicity levels.

Results of Trial 22: Excellent phytotoxic control of 4.3 and 4.4 ("severe-to-fatal") resulted at Day 5 and Day 7 at a solution concentration of 2.0M, and of 4.1 on Day 5 and Day 7 at a solution concentration of 1.5M. A 1.0M solution achieved strong phytotoxic results on Days 3-7. Controls sprayed with water and adjuvant mix only showed no effects.

Example 7

Trial 25: K-Acetate+Glacial Acetic Acid

In Trial 25, the herbicides comprised K-acetate at molarity 1.5; acidity adjusted with glacial acetic acid to approximately pH 4.3, 5.0, 6.0, and 7.0, proprietary adjuvant mix. Test plants (ref. Tables 4A and 4B): P-1, 14, 12, 19.

Figure 6:
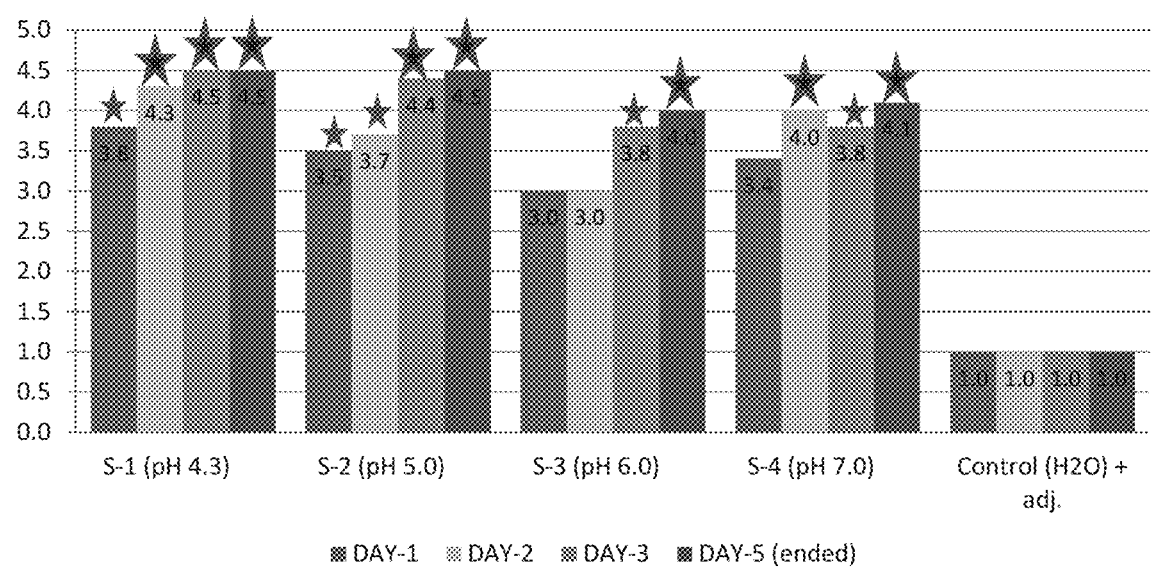
FIG. 6 depicts toxicity scores for the four plants tested in Trial 25, which tested an embodiment of an herbicide composition and method of using the same. The plants were numbered 22, 15, 13, and 19, corresponding to mixed monocotyledonous and dicotyledonous Pasture Blend 2, *Gazania rigens, Fragraria×ananassa* (Strawberry "Eversweet"), and *Nemophila menziesii discoidalis* (Baby Blue Eyes). Trial 25 examined the effects of a single 1.5 molar solution of potassium acetate at four acidities of pH 4.3 (Solution 1), pH 5 (Solution 2), pH 6 (Solution 3), and pH 7 (Solution 4). Adjuvants for each solution were identical and consisted of WIDESPREAD (Loveland Products) Solution 1 (S-1) corresponds to a 2.0 molar solution of potassium acetate, pH 5.01 achieved with succinic acid, and the inactive adjuvants urea and WIDESPREAD silicone surfactant (Loveland Products). Results of Trial 25: All solutions resulted in "severe-to-fatal" effects by termination of the test at Day 5. The most toxic of these results was observed at pH 4.3 and pH 5.0. However, the phytotoxic responses at pH 5.0 and 6.0 showed a more gradual increase over days 1-3. This is desired as it allows more time for absorption through the cuticulars layers prior to burning.

As shown in FIG. 6, and below in Table 12, the results of Trial 25 indicated excellent phytotoxic effects ("severe-to-fatal") at test conclusion on Day 5 with solutions at pH 4.3 and 5.0.

TABLE 12

Trial 25 Results
Test plants (ref. Table 4): P-1, 15, 13, 19

| Composition Tested | DAY-1 | DAY-2 | DAY-3 | DAY-5 (ended) |
|---|---|---|---|---|
| S-1 (pH 4.3)** | 3.8 | *4.3* | *4.5* | *4.5* |
| S-2 (pH 5.0)** | 3.5 | 3.7 | *4.4* | *4.5* |
| S-3 (pH 6.0)** | 3.0 | 3.0 | 3.8 | *4.0* |
| S-4 (pH 7.0)** | 3.4 | *4.0* | 3.8 | *4.1* |
| Control (H2O) + adj. | 1.0 | 1.0 | 1.0 | 1.0 |

**Bold, italicized toxicity values indicate "severe-to-fatal" toxicity levels.

Results of Trial 25: Highest excellent phytotoxic effects ("severe-to-fatal") resulted at test conclusion on Day 5 with solutions at pH 4.3 and 5.0.

Example 8

Trial 41: Ammonium Sulfate

In Trial 41, the herbicide comprised. Ammonium sulfate ([NH$_4$]$_3$ SO$_4$]; molarity 2.0; unadjusted pH approx. 5.5. Proprietary adjuvant mixes A (S-1) and B (S-2). Ref. Lab-2, p. 27. Test plants (ref. Tables 4A and 4B): P2, 2, 3, 10.

Excellent toxicity levels ("severe-to-fatal") resulted by test conclusion at Day 23 at solutions "B" concentration of 2.0M for Plant 3 and 10. Plants P-2 and 2 were considerably less responsive. Controls sprayed with water and adjuvant mix only showed no effects. Results are shown in FIG. 5 and Table 13.

TABLE 13

Trial 41 Averages Toxicities for S-2B and H$_2$O control (results for monocots "M" and dicots "D")

| | DAY-3 | | DAY-7 | | DAY-12 | | DAY-18 | | Day-23 | |
|---|---|---|---|---|---|---|---|---|---|---|
| | M | D | M | D | M | D | M | D | M | D |
| S-1 | 3.0 | *4.0* | 2.5 | *4.0* | 3.0 | *4.3* | 2.5 | *4.3* | 2.3 | *5.0* |
| S-2 * | 3.0 | *4.0* | 2.8 | *4.0* | 3.0 | *4.3* | 2.5 | *4.3* | 2.3 | *5.0* |
| Control (H2O) + adj. | 1.0 | 1.0 | 1.0 | 1.0 | 1.0 | 1.0 | 1.0 | 1.0 | 1.0 | 1.0 |

* Bold, italicized toxicity values indicate "severe-to-fatal" toxicity levels.

In Table 13, M refers to monocots and "D" refers to dicots.

Results of Trial 41:: For broadleaf (dicotyledonous) species of Sample S-1 at 2.0 Molar concentration, excellent phytotoxic effects from 4.0 to 5.0 ("severe-to-fatal") resulted from Day 3 through trial conclusion at Day 23. For grass and liliaceae (monocotyledonous, "M") species of Sample S-2 at 2.0 Molar concentration initial moderate effect of spray had decreases to 2.3 ("slight"). Controls sprayed with only water and adjuvant mix showed no effects. Dicots ("D") included in the Pasture 2 samples of S-1 and S-2 were all dead by Day 7, but data are not included in this graph.

Example 9

Herbicides Comprising Nitrogen Compounds

An aqueous solution comprising the active component ammonium sulfate [(NH$_4$)$_2$SO$_4$], and the non-active components citric acid [C$_6$H$_8$O$_7$] and a surfactant, is prepared by dissolving the ammonium sulfate and citric acid in water and adding the surfactant, and then sprayed onto weeds growing in soil. The aqueous solution has herbicidal effects on the weed plants.

Example 10

Herbicides Comprising Nitrogen Compounds

An aqueous solution comprising the active component ammonium nitrate [NH$_4$NO$_3$] and the non-active components citric acid [C$_6$H$_8$O$_7$] and a surfactant is prepared by dissolving the active and non-active components in water and adding the surfactant, and then sprayed onto weeds growing in soil. The aqueous solution has herbicidal effects on the weed plants.

Example 11

Herbicides Comprising Magnesium Compounds

"An aqueous solution comprising the active component magnesium nitrate [Mg(NO$_3$)$_2$], and the non-active components citric acid [C$_6$H$_8$O$_7$] and a surfactant, is prepared by dissolving the active and non-active components in water and adding the surfactant, and then sprayed onto weeds growing in soil. The aqueous solution has herbicidal effects on the weed plants.

Example 12

Herbicides Comprising Calcium Compounds

An aqueous solution comprising the active component calcium nitrate [Ca(NO$_3$)$_2$], and the non-active components citric acid [$C_6H_8O_7$] and a surfactant, is prepared by dissolving the active and non-active components in water and adding the surfactant, and then sprayed onto weeds growing in soil. The aqueous solution has herbicidal effects on the plant.

Example 13

Herbicides Comprising Micronutrients

Aqueous herbicidal compositions are prepared and applied to plants as described in Example 1, except that a micronutrient salt, Zn sulfate monohydrate: $ZnSO_4$—$H_2O$, is substituted for the potassium salt. Toxicity scoring is performed as described in Table 7. After a period of 3-30 days, plant death is observed.

Example 14

Trial 47: Potassium Acetate

In Trial 47, the herbicides comprised K-acetate; molarity range from 1.0-2.5; pH 5.03-5.05 with glacial acetic acid; proprietary adjuvant mix. Ref. Lab-2, p. 42. Test plants (ref Tables 4A and 4B): 5, 11b, 13, 22, 23b Table 14 shows the average toxicity scores for the four plants tested in Trial 47 (5, 11b, 13, 22, 23b) corresponding to *Brassica oleracea* (Kale), *Dichondra repens* (Dichondra), *Fragaria×ananassa* (Strawberry) Pasture Blend 2, and *Rosemarina officinalis* (Rosemary). S-1 corresponds to the highest concentration of active nutrient tested, S-4 corresponds to the lowest concentration of nutrient tested, and S-1 and 2 represent intermediate levels. The data are graphically presented below in FIG. 8.

TABLE 14

Trial 47 Post-Application Averaged Toxicity Levels (1-5)

|  | DAY-2 | DAY-5 | DAY-9 | DAY-14 |
|---|---|---|---|---|
| S-1 (2.5M)* | 3.8 | *4.5* | *4.8* | *4.9* |
| S-2 (2.0M)* | 3.7 | *4.0* | *4.8* | *4.8* |
| S-3 (1.5M)* | 3.6 | *4.3* | *4.8* | *5.0* |
| S-4 (1.0M)* | 3.7 | *4.4* | *4.8* | *4.8* |
| Control (H2O) + adj. | 1.0 | 1.0 | 1.0 | 1.0 |

**Bold, italicized toxicity values indicate "severe-to-fatal" toxicity levels.

Results of Trial 47: Excellent phytotoxic control of 4.5, 4.8 and 4.9 ("severe-to-fatal") resulted at Days 5, 9, to the conclusion of the trial at 14 at a solution concentration of 2.5M, of 4.0, 4.8, and 5.0 on Days 5, 9, and 14, at a solution concentration of 1.5M, and 4.3 through 4.4, 4.4, and 4.8 at a concentration of 1.0M. Controls sprayed with water and adjuvant mix only showed no phytotoxic effects.

Example 15

Trial 46—Mono-potassium Phosphate

In Trial 46, the herbicide comprised Mono-potassium phosphate ($KH_2PO_4$); molarity 2.0, and 1.0, approx. pH 4.1 without acid addition. Adjuvants comprised WIDESPREAD silicone surfactant and MSO. Test plants (ref. Table 4A) were P2, 5, 11a, 13.

Excellent phytotoxic effects ("severe-to-fatal") resulted at Days 8 through 18 for 1.0M and 1.5M solutions as shown in FIG. 9 and Table 15.

TABLE 15

Trial 46 - Averaged toxicities

|  | DAY-2 | | DAY-8 | | DAY-13 | | DAY-18 | | Avg. | |
|---|---|---|---|---|---|---|---|---|---|---|
|  | M | D | M | D | M | D | M | D | M | D |
| S- 2 (1.5M)* | 2.0 | 3.5 | 1.5 | *5.0* | 1.5 | *5.0* | 1.5 | *5.0* | 1.6 | *4.6* |
| S- 3 (1.0M)* | 2.0 | 3.5 | 1.5 | *5.0* | 2.0 | *5.0* | 1.5 | *5.0* | 1.8 | *4.6* |
| Control (H2O) + adj. | 1.0 | 1.0 | 1.0 | 1.0 | 1.0 | 1.0 | 1.0 | 1.0 | 1.0 | 1.0 |

*Bold, italicized toxicity values indicate "severe-to-fatal" toxicity levels.

In Table 15, "M" refers to monocots and "D" refers to dicots.

Results of Trial 46: Excellent phytotoxic control ("Severe-to-fatal") was observed from applications of both 2.0 and 1.5 molar test solution at Day 8 through Day 18, but only for broadleaf samples (divots). There was minimal effect during this period for the same solutions applied to the grasses in P-2. Controls appeared unaffected.

Example 16

Trial 56: Potassium Acetate

In Trial 56, the herbicide comprised. K-acetate; molarity of 1.5; pH 5.52 with citric acid; proprietary adjuvant mix. Ref. Lab-2, p. 69. Test plants (ref Tables 4A and 4B): 26, 3, 10, 11a.

Table 16 shows the average toxicity scores for the four plants tested (26, 3, 10, 11a) corresponding to *Viola×wittockiana*, (Viola), *Antirrhinum majus*, (Snapdragon), *Cineraria meritima*, (Dusty miller), and *Cymbalaria aequitriloba* (*Cymbalaria*). (Common purslane), *Echinochloa* (Barnyard grass), and *Chloris virgats* (Feather fingergrass). All plants were sprayed with a solution concentration of 1.5M. The Control solution was water only. The data are graphically presented below in FIG. 10. 1.5 molarity yielded strong phytotoxic control at Day 3, and excellent phytotoxic control at Day 4 through Day 15 and conclusion of trial.

TABLE 16

Trial 56 Post-Application Averaged Toxicity Levels (1-5)

| Sample Molarity | DAY-3 | DAY-4 | DAY-7 | DAY-10 | DAY-12 | Day-15 |
|---|---|---|---|---|---|---|
| S-1: 1.5M | 3.9 | *4.0* | *4.3* | *4.8* | *5.0* | *5.0* |
| Control (H20) | 1.1 | 1.1 | 1.1 | 1.1 | 1.1 | 1.1 |

** Bold, italicized toxicity values indicate "severe-to-fatal" toxicity levels.

Results of Trial 56: Excellent phytotoxic control of from 4.0 to 5.0 ("severe-to-fatal") resulted at Day 4 through the conclusion of the trial on Day 15 at the solution concentration of 1.5M. Controls sprayed with water only showed no phytotoxic effects.

Example 17

Trial 64: Disodium Octaborate Tetrahydrate

In Trial 64, the herbicide comprised disodium octahorate tetrahydrate ($Na_2B_8O_{13}$.4H2O) (Solubor®); molarity 0.5, pH 7.78. Kinetic®, urea, and sucrose adjuvants. Trial plants (ref. Table 4A) were 5, 18a, 22, 23b, 26.

Excellent phytotoxic control at 0.5 molarity was observed of all broadleaf species in the trial at Days 12 through 34, the conclusion of the trial. Partial control during this period was observed among the grass species in the trial. Results are shown in FIG. 14 and Table 17.

TABLE 17

Trial 64 Post-Application Averaged Phytooxicity Levels (1-5)

| S-2. 0.5 molar | DAY-12 | DAY-34 |
|---|---|---|
| Pasture Mix 2 | 3.0 | 2.8 |
| *Rosemarina off.* | 4.5 | 5.0 |
| *Viola x wittockiana* | 4.5 | 5.0 |
| *Brassica oleracea* (Kale) | 4.5 | 5.0 |
| *Matthiola incana* (Stock) | 5.0 | 5.0 |

Example 18

Trial 44: Zinc Sulfate

In Trial 44, the herbicides comprised $ZnSO_4$; molarity range from 1.0-2.0; pH 5.10-5.64 with no acid addition; proprietary adjuvant mix. Ref. Lab-2, p. 33. Test plants (ref Tables 4A and 4B): 22, 2, 10, 3.

Table 18 shows the average toxicity scores for the four plants tested in Trial 44 (22, 2, 10, 3) corresponding to Pasture Blend 2, *Allium cepa* (Onion), *Cineraria maritima* (Dusty miller) and *Antirrhinum majus* (Snapdragon). S-1 corresponds to the highest concentration of active nutrient tested, S-3 corresponds to the lowest concentration of nutrient tested and S-2 represents an intermediate level. The data are graphically presented in FIG. 13. In Trial 44, 2.0 molar solution yielded strong control of 3.9 at Day 9, and excellent control of 4.6 through 5.0 at Day 21 through Day 32. 1.5 and 1.0 molar solutions yielded excellent controls of approximately 4.5 each at Day 21 through Day 32, the conclusion of trial.

TABLE 18

Trial 44 Post-Application Averaged Toxicity Levels (1-5)

| Sample Molarity | DAY-2 | DAY-4 | DAY-5 | DAY-9 | DAY-21 | DAY-27 | DAY-32. Trial concluded. |
|---|---|---|---|---|---|---|---|
| S-1: 2.0M | 2.3 | 3.1 | 3.2 | 3.9 | *4.6* | *5.0* | *5.0* |
| S-2: 1.5M | 2.2 | 2.7 | 2.8 | 3.5 | *4.5* | *4.6* | *4.8* |
| S-3: 1.0M | 2.0 | 2.5 | 3.0 | 3.7 | *4.3* | *4.4* | *4.2* |
| Control (H20 + adj.) | 1.1 | 1.1 | 1.1 | 1.3 | 1.1 | 1.1 | 1.1 |

** Bold, italicized toxicity values indicate "severe-to-fatal" toxicity levels.

Results of Trial 44: Excellent phytotoxic control of 4.6 to 5.0 ("severe-to-fatal") resulted at Day 21 through the conclusion of the trial at Day 32 at a solution concentration of 2.0M, of 4.5 through 4.8 on Days 21 through Day 32 at a solution concentration of 1.5M, and of 4.3, 4.4, and 4.2 on Days 521 through 32 at a concentration of 1.0M. Controls sprayed with water and adjuvant mix only showed no phytotoxic effects.

Example 19

Trial 50: Potassium Acetate, Mature Field Weeds

In Trial 50, the herbicides comprised K-acetate; molarity range from 1.5, 2.0 and 2.5; 5.0 with citric acid; proprietary adjuvant mix. Ref. Lab-2, p. 48. Test plants were mature field weeds.

Table 19 shows the average toxicity scores for the field weeds. S-1 corresponds to the highest concentration of active nutrient tested, S-3 corresponds to the lowest concentration of nutrient tested, and S-2 represent an intermediate level. The data are graphically presented below in FIG. 11.

TABLE 19

Trial 50 Post-Application Averaged Toxicity Levels (1-5)

| Sample Molarity | DAY-3 | DAY-10 |
|---|---|---|
| S-1: 2.5M | 2.8 | 2.8 |
| S-2: 2.0M | 3.6 | 3.6 |
| S-3: 1.5M | 3.5 | 3.4 |
| Control-1 (H20 + adj.) | 0.1 | 0.4 |
| Control-2 (H20) | 0.1 | 0.1 |

Results of Trial 50: Strong phytotoxic control of 3.6 resulted at Day 3 and the conclusion of the trail at Day 10 at a solution concentration of 2.0M, reduced phytotoxic results of 2.8 were observed on Days 3 and 10 at a solution concentration of 2.5M. Controls sprayed with water and adjuvant mix only showed no phytotoxic effects.

Example 20

Trial 54: Potassium Acetate and Young Weeds in Greenhouse

In Trial 54, the herbicide comprised K-acetate; molarity of 2.0; pH 5.04 with citric acid; proprietary adjuvant mix. Ref. Lab-2, p.65. Test plants (ref Tables 4A and 4B): 23A, 11C, 9A. Height of plants used in this trial was approximately 4-8".

Table 20 shows the average toxicity scores for the three weeds tested (54, 23A, 11C, 9A) corresponding to *Portulaca olerace* (Common purslane), *Echinochloa* (Barnyard grass), and *Chloris virgats* (Feather fingergrass). All ple solution of 2.0M and pH 5.04. Control solutions were water only. The data are graphically presented below in FIG. 12.

TABLE 20

Trial 54 Post-Application Averaged Toxicity Levels (1-5)

| Sample Molarity | DAY-4 | DAY-14 | DAY-16 | DAY-18 |
|---|---|---|---|---|
| Purslane | *4.0* | *5.0* | *5.0* | *5.0* |
| Barn. Grs. 1 | *4.5* | *4.5* | *5.0* | *5.0* |
| Barn. Grs. 2 | *4.0* | *5.0* | *5.0* | *5.0* |

TABLE 20-continued

Trial 54 Post-Application Averaged Toxicity Levels (1-5)

| Sample Molarity | DAY-4 | DAY-14 | DAY-16 | DAY-18 |
|---|---|---|---|---|
| Feather fingr. | 4.5 | *5.0* | *5.0* | *5.0* |
| Control | 1.2 | 1.0 | 1.0 | 1.0 |

** Bold, italicized toxicity values indicate "severe-to-fatal" toxicity levels.

Results of Trial 54: Excellent phytotoxic control of from 4.0 to 5.0 ("severe-to-fatal") resulted at Day 4 through the conclusion of the trial on Day 18 at the solution concentration of 2.0M. Controls sprayed with water only showed no phytotoxic effects.

Without being limited by theory, it is contemplated that that by definition plants typically require only very small quantities of micronutrient. Micronutrients are useful in accordance with some embodiments, for example when zinc (Zn) and boron (B) formulations are applied for herbicidal action on crops requiring Zn and/or B supplements for growth and development. In contrast, applications will not be of interest that could result in toxic quantities of residual micronutrients in the soil used to grow crops or landscape vegetation. However, in some embodiments, compositions comprising micronutrients are useful for rights-of-way, road-sides, or where a crop or ornamental vegetation will not be affected.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended, in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

REFERENCES

The following references are hereby incorporated by reference in their entireties.

Abou El-Nour, E. A. A. 2002 Can supplemented potassium foliar feeding reduce the recommended soil potassium? Pak. J. Biol. Sci. 5(3):259-262.

Abouziena, H. F. A., A. A. M. Omar, S. D. Sharma and M. Singh. 2009. Efficacy comparison of some new natural-product herbicides for weed control in two growth stages. Weed Manag. Tech. 23:431-437.

Anonymous, 2016. Eutrophication. Wikipedia. accessible on the world wide web at en.wikipedia.org/wiki/Eutrophication Berndt, G. F. 1987. Efficiency of foliar sprays as influenced by the inclusion of adjuvants. Res. Devlop. Agric. 4(3): 129-139.

Borowski, E. and S. Michalek. 2009. The effect of foliar feeding of potassium salts and urea in spinach on gas exchange, leaf yield and quality. ACTA Agrobotanica 62(1): 155-162)

Bukovac, M. J. and S. H. Wittwer. 1957. Absorption and mobility of foliar applied nutrients. Plant Physiol. 32(5): 428-435.

Christensen, L. P. 2005. Foliar fertilization in vine mineral nutrient management programs. In Soil Environment and Vine Mineral Nutrition. Amer. Soc. Enol. and Viticul. Pages 83-90.

Christensen, L. Peter and William L. Peacock. 2000. Mineral Nutrition and Fertilization. Ch 14. In Raisin Production Manual. Univ. Calif., Ag. And Nat'l Res. Communication Serv.: 102-114.

Czamota, Mark and Paul Thomas. 2013. Using Surfactants, Wetting Agents, and Adjuvants in the Greenhouse. Univ. Georgia Coop. Extn., Athens, Ga. Pub. B-1309. 10 pp.

Elser, J. J, M. E. S. Bracken, E. E. Cleland, D. S. Gruner, W. S. Harpole, H. Hillebrand, J. T. Ngai, E. W. Seabloom., J. B. Shurin and J. S. Smith. 2007. Global analysis of nitrogen and phosphorus limitation of primary producers in freshwater, marine and terrestrial ecosystems. 2007. Ecology Letters. 10: 8 pp.

Hager, Aron and Marshal McGlamery. 1997. Principles of Postemergence Herbicides. Univ. of Ill. Coop. Eaten. Servo Urbana, Ill. 4-pp.

Havlin, J. L., S. L. Tilsdale, W. E. Nelson, and J. D. Beaton. 2014. Soil Fertility and Fertilizers. An Introduction to Nutrient Management. 8th ed. Pearson Prentice Hall, Upper Saddle River, N. J. 516 pp Howard, D. D., C. O. Gwathmey and C. E. Sams. 1998. Foliar feeding of cotton: evaluating potassium sources, potassium solution buffering, and boron. Agron. J.: 740-746

Johnson, Bob. 2016. Pay attention to timing when applying fertilizer. In Feb. 3, 2016 issue AgAlert. Calif. Farm Bur. Pub: 11-13.

Kutural, S. K., J. G. Strang, and C. Smigell. Undated. Fertilization of Grapevines. HortFact 3104, Univ. Kentucky, Coll. Ag., Coop. Eaten. Serv. 6 pp.

Marschner, H. 1995. Mineral Nutrition of Higher Plants. $2^{nd}$ ed. Academic Press. London. 674 pp.

McCauley, Ann, Clain Jones, and Jeff Jacobsen. 2011 (reprinted). Nutrient Management: A Self-Study Course from the Montana State Extension Service Continuing Education Series. Nut. Mgt. Module No. 9. 16 pp Mengel, K. 2002. Alternative or complementary role of foliar supply in mineral nutrition. 2002 Proc. Int. Symp. on Foliar Nutrition. Acta Hort. 594: 33-47

Mengel, K. 1985. Dynamics and availability of major nutrients in soils. Adv. Soil Sci. 2: 63-131

Munson, R. D, and W. L. Nelson. 1963. Movement of applied potassium in soils. J. Agri. Food Chem. 11(3): 193-201

Nicholson, Joseph. 2017. What happens when plants get too much potassium? Article accessible on the world wide web at www.hunker.com Oosterhuis, Derrick. 2009. Foliar fertilization: the mechanisms and magnitude of nutrient uptake. In Fluid Fertilizer Foundation Proc. Feb. 15-17, 2009. 4 pp Roberts, J. R., A. K. Underwood, A. Clark, R. E. Mack, J. M. Thomas and G. C. Volgas. 1997. Dry concentrate (DC) spray adjuvants. In Pesticides Formulations and Application Systems: Vol. 17. ASTM STP 1328. G. R. Goss, M. J. Hopkinson and H. M. Collins, eds. American Society for Testing and Materials: 257-266.

Shafer, W. E. and D. W. Reed. 1986. The foliar absorption of potassium from organic and inorganic potassium carriers, J. Plant Nutri. 9(2): 143-157

Smith-Fiola, Deborah and Stanton Gill. 2014. Iron-Based Herbicides: Alternative Materials for Weed Control in Landscapes and Lawns. Univ. Md. Extension. 4 pp Taiz, L., E. Zeiger, I. M. Moller and A. Murphy. 2015 Plant Physiology and Development. 6 ed. Sinauer Assoc., Sunderland, Mass. USA. 761 pp.+appendices U.S. Food and Drug Administration. 2007. Approximate pH of foods and food products. Accessible on the world wide web at www.foodscience.caes.uga.edu/extension/documents/fdaapproximatephoffoodslacf-phs.pdf.

Wojcik, Pawel. 2004. Uptake of mineral nutrients from foliar fertilization (review). J. Fruit and Ornamental Pl. Res. 12 (spec ed.): 201-218

Zollinger, Rich. Spray Adjuvants: The Rest of the Story. CWSS Res. Data Update & News, January 2014. 5 pp.

What is claimed is:

1. A method of inducing phytotoxicity in a plant, the method comprising administering an excess of nutrient in an aqueous composition to foliar portions of the plant, wherein the aqueous composition comprises:
   at least one nutrient compound comprising a micronutrient; and
   at least one adjuvant,
   wherein the pH of the aqueous composition is about 4 to about 7,
   wherein the excess of nutrient is an amount effective to be absorbed systemically by the plant and cause systemic terminal physiological disruption in the plant,
   whereby the excess of micronutrient is absorbed systemically by the plant, thereby inducing systemic phytotoxicity in the plant, thereby killing the plant.

2. The method of claim 1, wherein the excess of micronutrient absorbed by the plant causes opening of stromata of the plant, thereby desiccating the plant.

3. The method of claim 1, wherein the aqueous composition further comprises an organic acid or a mineral acid.

4. The method of claim 1, wherein the pH of the composition is about 4.5 to about 5.5.

5. The method of claim 1, wherein the concentration of the micronutrient in the aqueous composition is about 1 M to about 2 M.

6. The method of claim 1, wherein the aqueous composition further comprises an organic acid, and the organic acid is selected from the group consisting of acetic acid, citric acid, lactic acid, formic acid, succinic acid, tartaric acid, malic acid, and oxalic acid.

7. The method of claim 1, wherein the nutrient compound comprises:
the micronutrient; and
an oppositely-charged ion, wherein the oppositely-charged ion is not an herbicide in the quantities of the composition.

8. The method of claim 1, wherein the composition has a low point of deliquescence (POD), whereby the composition is retained in semi-liquid state on the foliar portion of the plant for 2-4 days.

9. The method of claim 1, further comprising a second administration within 14 days of the first administration of the composition.

10. The method of claim 1, further comprising administering a burn down herbicide to the plant.

11. The method of claim 10, wherein the burn down herbicide comprises an organic acid composition selected from the group consisting of: a composition comprising caprylic (octanoic) acid and capric (decanoic) acid, a composition comprising pelargonic (nonanoic) acid and $C_6$-$C_{12}$ fatty acids, and a composition comprising ammonium nonanoate, and a composition comprising an ammonium salt of pelargonic acid.

12. The method of claim 1, wherein the adjuvant comprises a surfactant, a humectant, or both.

13. The method of claim 12, wherein the humectant comprises a sugar selected from the group consisting of dextrose, fructose, sucrose, or a combination of any of these.

14. The method of claim 1, wherein the concentration of the nutrient in the aqueous composition is about 0.5 M to about 5 M.

15. The method of claim 1, wherein the micronutrient is selected from the group consisting of Cl, Fe, B, Mn, Cu, and Mo, or a combination of the listed items.

* * * * *

UNITED STATES PATENT AND TRADEMARK OFFICE
CERTIFICATE OF CORRECTION

| | |
|---|---|
| PATENT NO. | : 10,595,534 B2 |
| APPLICATION NO. | : 16/193312 |
| DATED | : March 24, 2020 |
| INVENTOR(S) | : David A. Cobb |

It is certified that error appears in the above-identified patent and that said Letters Patent is hereby corrected as shown below:

On the Title Page

In Column 2, item (72), Abstract, Line 2, delete "phyotoxicity" and insert --phytotoxicity--.

In Column 2, item (72), Abstract, Line 8, delete "phytoxicity" and insert --phytotoxicity--.

On page 2, in Column 1, item (56), Other Publications, Line 27, delete "enwikipedia." and insert --en.wikipedia.--.

On page 2, in Column 1, item (56), Other Publications, Line 36, delete "III" and insert --Ill--.

On page 2, in Column 1, item (56), Other Publications, Line 40, delete "al,," and insert --al.,--.

In the Specification

In Column 1, Line 9, delete "62/609137," and insert --62/609,137,--.

In Column 1, Line 52, delete "dessicating" and insert --desiccating--.

In Column 1, Line 62, delete ""Gramazone","" and insert --"Gramoxone",--.

In Column 2, Line 45, delete "phoytotoxicity" and insert --phytotoxicity--.

In Column 2, Line 46, delete "phyotoxicity." and insert --phytotoxicity.--.

In Column 3, Line 15, delete "chealated" and insert --chelated--.

In Column 3, Line 44, delete "meritima" and insert --maritima--.

In Column 3, Lines 44-45, delete "aequitrilobia" and insert --aequitriloba--.

Signed and Sealed this
Twenty-fifth Day of August, 2020

Andrei Iancu
*Director of the United States Patent and Trademark Office*

In Column 3, Line 46, delete "Gallium" and insert --Galium--.

In Column 3, Line 47, delete "paludosu," and insert --paludosum,--.

In Column 3, Line 50, delete "oleracia," and insert --oleracea,--.

In Column 3, Line 50, delete "Rosmarina" and insert --Rosmarinus--.

In Column 3, Line 50, delete "Santivitalia" and insert --Sanvitalia--.

In Column 3, Line 51, delete "wittockiana," and insert --wittrockiana,--.

In Column 3, Line 53, delete "heterophyllia," and insert --heterophylla,--.

In Column 3, Line 58, delete "meritima" and insert --maritima--.

In Column 3, Line 59, delete "Gallium" and insert --Galium--.

In Column 3, Line 60, delete "paludosu," and insert --poludasu,--.

In Column 3, Line 62, delete "Santivitalia" and insert --Sanvitalia--.

In Column 3, Line 63, delete "wittockiana," and insert --wittrockiana,--.

In Column 3, Line 65, delete "heterophyllia," and insert --heterophylla,--.

In Column 5, Line 41, delete "herein," and insert --herein.--.

In Column 5, Line 54, delete "solution," and insert --solution.--.

In Column 5, Line 63, delete "in some" and insert --In some--.

In Column 5, Line 67, after "composition" insert --.--.

In Column 6, Line 12, delete "meritima" and insert --maritima--.

In Column 6, Line 23, delete "effect)" and insert --effect--.

In Column 6, Line 33 (approx.), delete "meritima" and insert --maritima--.

In Column 6, Line 52, delete "same," and insert --same.--.

In Column 6, Line 53, delete "13," and insert --22, 13,--.

In Column 7, Line 21, delete "fur to" and insert --(Refer to--.

CERTIFICATE OF CORRECTION (continued)
U.S. Pat. No. 10,595,534 B2

In Column 7, Line 49, delete "meritima" and insert --maritima--.

In Column 7, Line 49, delete "(Dusty" and insert --Dusty--.

In Column 8, Line 4, delete "Fragraria" and insert --Fragaria--.

In Column 8, Line 29, delete "2." and insert --2,--.

In Column 8, Line 29, delete "Fragraria" and insert --Fragaria--.

In Column 8, Line 30, delete "Rosmarina" and insert --Rosmarinus--.

In Column 8, Line 52, delete "Fragraria" and insert --Fragaria--.

In Column 9, Line 7, delete "wittockiana," and insert --wittrockiana,--.

In Column 9, Line 13, delete "Trial 56," and insert --Trial 56.--.

In Column 10, Line 40, delete "unharmed," and insert --unharmed.--.

In Column 10, Line 42, delete "2014) The" and insert --2014). The--.

In Column 10, Line 65, delete "at," and insert --al.,--.

In Column 10, Line 67, delete "entirety)" and insert --entirety).--.

In Column 12, Line 9, delete ""micronutrient,"" and insert --"micronutrient."--.

In Column 12, Line 48, delete "1B." and insert --1B--.

In Column 17, Line 39, delete "Phtotoxicity" and insert --Phytotoxicity--.

In Column 17, Lines 46-47, delete "pytotoxicity"." and insert --phytotoxicity".--.

In Column 17, Line 53, delete "entirety)" and insert --entirety).--.

In Column 18, Line 44, delete "1.2-2,0 M," and insert --1.2-2.0M,--.

In Column 18, Line 55, delete "herbicide," and insert --herbicide.--.

In Column 19, Line 3, delete "entirety)" and insert --entirety).--.

In Column 19, Line 9 (approx.), delete "2015)" and insert --2015).--.

In Column 19, Line 13 (approx.), delete "El-Nous," and insert --El-Nour,--.

In Column 19, Line 17, delete "entirety)" and insert --entirety).--.

In Column 19, Line 29, delete "electroneutrahty" and insert --electroneutrality--.

In Column 19, Line 45, delete "2015)" and insert --2015).--.

In Column 19, Line 55, delete "2015)" and insert --2015).--.

In Column 20, Line 1, delete "of" and insert --of $K^+$--.

In Column 20, Line 17 (approx.), delete "entirety)" and insert --entirety).--.

In Column 20, Line 46, delete "entirety)," and insert --entirety).--.

In Column 22, Line 62, delete "in some" and insert --In some--.

In Column 23, Table 2A, Line 23, delete "$KRH_2PO_4$," and insert --$KH_2PO_4$,--.

In Column 23, Table 2C, Line 59 (approx.), delete "phosphate:(" and insert --phosphate: (--.

In Column 24, Table 2D, Line 9, delete "Langbenite:" and insert --Langbeinite:--.

In Column 24, Table 2D, Line 17, delete "$M_2SO_4$" and insert --$MgSO_4$--.

In Column 24, Table 2D, Line 19 (approx.), delete "Mg $SO_4$" and insert --$MgSO_4$--.

In Column 24, Table 2G, Line 64 (approx.), delete "$(NH_4)_2SO4$" and insert --$(NH_4)_2SO_4$--.

In Column 25, Table 2H, Line 17 (approx.), delete "polyflavanoid" and insert --polyflavonoid--.

In Column 25, Table 2J, Line 42 (approx.), delete "polyflavanoid" and insert --polyflavonoid--.

In Column 26, Line 35 (approx.), delete "organic donator" and insert --organic H+ donator--.

In Column 26, Line 45 (approx.), delete "acidity'" and insert --acidity--.

In Column 26, Table 3, Line 62 (approx.), delete "(Benzenecarboxylic" and insert --Benzenecarboxylic--.

In Column 28, Lines 25-26, delete "0.1M 5M, 0.1M 4M, 0.1M 3M, 0.1M 2M, 0.5M 5M, 0.5M 4M," and insert --0.1M-5M, 0.1M-4M, 0.1M-3M, 0.1M-2M, 0.5M-5M, 0.5M-4M,--.

In Column 28, Line 28, delete "1.5M 3M, or 1.5M 2M." and insert --1.5M-3M, or 1.5M-2M.--.

In Column 30, Line 42, delete "nolarity" and insert --molarity--.

CERTIFICATE OF CORRECTION (continued)
U.S. Pat. No. 10,595,534 B2

In Column 31, Table 3.1, Line 28 (approx.), delete "Aminopyraild" and insert --Aminopyralid--.

In Column 31, Table 3.1, Line 29 (approx.), delete "Bromcil" and insert --Bromacil--.

In Column 31, Table 3.1, Line 30 (approx.), delete "Chlorobenil" and insert --chlorobenzyl--.

In Column 31, Table 3.1, Line 33 (approx.), delete "Ropoxycarbazone" and insert --Propoxycarbazone--.

In Column 31, Table 3.1, Line 35 (approx.), delete "Flumioxazzin" and insert --Flumioxazin--.

In Column 31, Line 44, delete "defolitating," and insert --defoliating,--.

In Column 33, Line 8, delete "sulfate decanoic" and insert --sulfate + decanoic--.

In Column 33, Line 17, delete "[C6-C12]"" and insert --[$C_6$-$C_{12}$]"--.

In Column 33, Line 23, delete "C6-C12" and insert --$C_6$-$C_{12}$--.

In Column 33, Line 29, delete "[C6-C12]"" and insert --[$C_6$-$C_{12}$]"--.

In Column 33, Line 64, delete "dessicating" and insert --desiccating--.

In Column 34, Line 65, delete "meritima," and insert --maritima,--.

In Column 34, Line 66, delete "aequitrilobia," and insert --aequitriloba,--.

In Column 35, Line 1, delete "Gallium" and insert --Galium--.

In Column 35, Line 2, delete "paludosu," and insert --poludasu,--.

In Column 35, Line 5, delete "oleracia," and insert --oleracea,--.

In Column 35, Line 5, delete "Rosmarina" and insert --Rosmarinus--.

In Column 35, Line 5, delete "Santivitalia" and insert --Sanvitalia--.

In Column 35, Line 6, delete "wittockiana," and insert --wittrockiana,--.

In Column 35, Lines 8-9, delete "heterophyllia," and insert --heterophylla,--.

In Column 35, Line 9, delete "Mathilda" and insert --Matthiola,--.

In Column 35, Line 15, delete "meritima" and insert --maritima--.

In Column 35, Line 16, delete "Gallium" and insert --Galium--.

CERTIFICATE OF CORRECTION (continued)
U.S. Pat. No. 10,595,534 B2

In Column 35, Lines 17-18, delete "paludosu," and insert --poludasu,--.

In Column 35, Line 20, delete "Santivitalia" and insert --Sanvitalia--.

In Column 35, Line 20, delete "wittockiana," and insert --wittrockiana,--.

In Column 35, Line 23, delete "heterophyllia," and insert --heterophylla,--.

In Column 35, Line 56, delete "second." and insert --second--.

In Column 36, Line 24, delete "N, S," and insert --N, Mg, S,--.

In Column 37, Line 12 (approx.), delete "N, S," and insert --N, Mg, S,--.

In Column 37, Line 59, delete "items" and insert --items.--.

In Column 38, Line 16, delete "phoytotoxicity" and insert --phytotoxicity--.

In Column 38, Line 17, delete "phyotoxicity." and insert --phytotoxicity.--.

In Column 38, Line 19, delete "dessication" and insert --desiccation--.

In Column 38, Line 26, delete "dessication" and insert --desiccation--.

In Column 39, Line 6, delete "phytoxicity"" and insert --phytotoxicity"--.

In Columns 39-40, Table 4A, Line 16, delete "meritima" and insert --maritima--.

In Columns 39-40, Table 4A, Line 21, delete "Echinochlora" and insert --Echinochloa--.

In Columns 39-40, Table 4A, Line 25, delete "Gallium" and insert --Galium--.

In Columns 39-40, Table 4A, Line 29, delete "crinus" and insert --erinus--.

In Columns 39-40, Table 4A, Line 30, delete ""AlicePurple"" and insert --"Alice Purple"--.

In Columns 39-40, Table 4A, Line 44, delete "olerace" and insert --oleracea--.

In Columns 39-40, Table 4A, Line 45, delete "23a." and insert --23b.--.

In Columns 39-40, Table 4A, Line 45, delete "Rosmarina" and insert --Rosmarinus--.

In Columns 39-40, Table 4A, Line 46, delete "Santivitalia" and insert --Sanvitalia--.

In Columns 39-40, Table 4A, Line 50, delete "wittockiana" and insert --wittrockiana--.

In Columns 39-40, Table 4A, Line 51, delete "gemination." and insert --germination--.

In Column 41, Table 4B, Line 10, delete "heterophyllia" and insert --heterophylla--.

In Column 41, Line 26, delete "conducted date" and insert --conducted to date--.

In Column 41, Table 5, Line 63, delete "2.002.5" and insert --2.00-2.5--.

In Column 42, Line 14, delete "are, also" and insert --are also--.

In Column 42, Line 50, delete "1 and 2," and insert --1 and 2.--.

In Column 42, Line 63, delete "Herbicidal." and insert --Herbicidal--.

In Column 43, Line 8, delete "5.01," and insert --5.01.--.

In Column 44, Line 6, delete "1.5. 4)" and insert --15.4)--.

In Columns 43-44, Table 6A, Line 8, delete "H20" and insert --$H_2O$--.

In Columns 43-44, Table 6A, Line 11, delete "H20" and insert --$H_2O$--.

In Columns 43-44, Table 6A, Line 12, delete "H20" and insert --$H_2O$--.

In Columns 43-44, Table 6A, Line 19, delete "H2O" and insert --$H_2O$--.

In Columns 43-44, Table 6A, Line 30, delete "H20" and insert --$H_2O$--.

In Columns 43-44, Table 6A, Line 32, delete "H20" and insert --$H_2O$--.

In Columns 43-44, Table 6A, Line 43, delete "H20" and insert --$H_2O$--.

In Columns 43-44, Table 6A, Line 44, delete "H20" and insert --$H_2O$--.

In Columns 43-44, Table 6A, Line 51, delete "H20" and insert --$H_2O$--.

In Columns 43-44, Table 6A, Line 52, delete "H20" and insert --$H_2O$--.

In Columns 43-44, Table 6A, Line 57, delete "H20" and insert --$H_2O$--.

In Columns 43-44, Table 6A, Line 59, delete """ and insert --Potassium (K)--.

In Columns 45-46, Table 6A-continued, Line 12, delete "H20" and insert --$H_2O$--.

In Columns 45-46, Table 6A-continued, Line 13, delete "H20" and insert --$H_2O$--.

In Columns 45-46, Table 6A-continued, Line 23, delete "FIG, 4A" and insert --FIG. 4A--.

In Columns 45-46, Table 6A-continued, Line 24, delete "H20" and insert --$H_2O$--.

In Columns 45-46, Table 6A-continued, Line 36, delete "H20" and insert --$H_2O$--.

In Columns 45-46, Table 6A, Line 48, delete "H20" and insert --$H_2O$--.

In Columns 45-46, Table 6A-continued, Line 60, delete "H20" and insert --$H_2O$--.

In Columns 45-46, Table 6A-continued, Line 68, delete "H20" and insert --$H_2O$--.

In Columns 45-46, Table 6A-continued, Line 76, delete "H20" and insert --$H_2O$--.

In Columns 47-48, Table 6A-continued, Line 6, delete "ZnSO4" and insert --$ZnSO_4$--.

In Columns 47-48, Table 6A-continued, Line 34, delete "T54." and insert --T54,--.

In Columns 47-48, Table 6A-continued, Line 36, delete "T54." and insert --T54,--.

In Columns 47-48, Table 6A-continued, Line 36, delete "Bnyrd" and insert --Barnyard--.

In Columns 47-48, Table 6A-continued, Line 38, delete "T54. Brnyrd" and insert --T54, Barnyard--.

In Columns 47-48, Table 6A-continued, Line 42, delete "T54." and insert --T54,--.

In Columns 53-54, Table 6B-continued, Line 17, delete "test'd)" and insert --(est'd)--.

In Columns 55-56, Table 6B-continued, Line 34, delete "T54." and insert --T54,--.

In Columns 55-56, Table 6B-continued, Line 37, delete "T54." and insert --T54,--.

In Columns 55-56, Table 6B-continued, Line 38, delete "Brnyrd" and insert --Barnyard--.

In Columns 55-56, Table 6B-continued, Line 40, delete "T54." and insert --T54,--.

In Columns 55-56, Table 6B-continued, Line 41, delete "Brnyrd" and insert --Barnyard--.

In Columns 55-56, Table 6B-continued, Line 43, delete "T54." and insert --T54,--.

In Column 55, Line 55, delete "ettects" and insert --effects--.

In Column 56, Line 64, delete "(21,22, 10" and insert --21, 22, 10--.

In Column 56, Line 66, delete "meritima" and insert --maritima--.

In Columns 57-58, Table 7, Line 5, delete "H20" and insert --$H_2O$--.

In Columns 57-58, Table 7, Line 6, delete "H20" and insert --$H_2O$--.

In Columns 57-58, Table 7, Line 8, delete "H20" and insert --$H_2O$--.

In Columns 57-58, Table 7, Line 9, delete "H20" and insert --$H_2O$--.

In Columns 57-58, Table 7, Line 16, delete "H20" and insert --$H_2O$--.

In Columns 57-58, Table 7, Line 23, delete "H20" and insert --$H_2O$--.

In Columns 57-58, Table 7, Line 24, delete "H20" and insert --$H_2O$--.

In Columns 57-58, Table 7, Line 31, delete "H20" and insert --$H_2O$--.

In Columns 57-58, Table 7, Line 32, delete "H20" and insert --$H_2O$--.

In Columns 57-58, Table 7, Line 37, delete "H20" and insert --$H_2O$--.

In Columns 57-58, Table 7, Line 38, delete "H20" and insert --$H_2O$--.

In Columns 57-58, Table 7, Line 39, delete "15/4,8;" and insert --15/4.8;--.

In Columns 57-58, Table 7, Line 45, delete "H20" and insert --$H_2O$--.

In Columns 57-58, Table 7, Line 46, delete "H20" and insert --$H_2O$--.

In Columns 57-58, Table 7, Line 47, delete "H20" and insert --$H_2O$--.

In Columns 57-58, Table 7, Line 52, delete "H20" and insert --$H_2O$--.

In Columns 57-58, Table 7, Line 59, delete "H20" and insert --$H_2O$--.

In Columns 57-58, Table 7, Line 63, delete "(end.)" and insert --(end) --.

In Columns 57-58, Table 7, Line 67, delete "H20" and insert --$H_2O$--.

In Columns 59-60, Table 7-continued, Line 4, delete "H20" and insert --$H_2O$--.

In Columns 59-60, Table 7-continued, Line 13, delete "H20" and insert --$H_2O$--.

In Columns 59-60, Table 7-continued, Line 20, delete "H20" and insert --$H_2O$--.

In Columns 59-60, Table 7-continued, Line 23, delete "H20" and insert --$H_2O$--.

CERTIFICATE OF CORRECTION (continued)
U.S. Pat. No. 10,595,534 B2

In Columns 59-60, Table 7-continued, Line 25, delete "41./2.3" and insert --41/2.3--.

In Columns 59-60, Table 7, Line 28, delete "H20" and insert --$H_2O$--.

In Columns 59-60, Table 7-continued, Line 29, delete "1.8/1.0;" and insert --18/1.0;--.

In Column 59, Table 8, Line 51, delete "H20" and insert --$H_2O$--.

In Column 60, Line 45, delete "L5, 1.0;" and insert --1.5, 1.0;--.

In Column 60, Line 49, delete "(21,22" and insert --(21, 22--.

In Column 60, Line 50, delete "meritima" and insert --maritima--.

In Columns 61-62, Table 10A, Line 8, delete "(H20" and insert --($H_2$0--.

In Columns 61-62, Table 10B, Line 8, delete "(H20" and insert --($H_2$0--.

In Column 62, Line 28, delete "(22,15,13, 19" and insert --22, 15, 13, 19--.

In Column 63, Line 58, delete "comprised." and insert --comprised--.

In Column 64, Line 16, delete "Trial 41 ::" and insert --Trial 41 :--.

In Column 65, Line 26, delete "23b" and insert --23b.--.

In Column 65, Line 31, delete "Rosemarina" and insert --Rosmarinus--.

In Column 66, Line 18, delete "(divots)." and insert --(dicots).--.

In Column 66, Line 25 (approx.), delete "comprised." and insert --comprised--.

In Column 66, Lines 30-31, delete "wittockiana," and insert --wittrockiana,--.

In Column 66, Line 32, delete "meritima," and insert --maritima,--.

In Column 66, Line 34, delete "virgats" and insert --virgata--.

In Column 66, Table 16, Line 45, delete "Day-15" and insert --DAY-15--.

In Column 66, Table 16, Line 48, delete "(H20)" and insert --($H_2O$)--.

In Column 66, Line 62, delete "4H2O)" and insert --4$H_2O$)--.

In Column 66, Line 63, delete "pH 7.78." and insert --pH $\cong$ 7.78.--.

In Column 67, Table 17, Line 6, delete "Phytooxicity" and insert --Phytotoxicity--.

In Column 67, Table 17, Line 9, delete "Rosemarina" and insert --Rosmarinus--.

In Column 67, Table 17, Line 10, delete "wittockiana," and insert --wittrockiana,--.

In Columns 67-68, Table 18, Line 9, delete "(H20" and insert --($H_2O$--.

In Column 67, Line 65, delete "2.5; 5.0" and insert --2.5; pH 5.0--.

In Column 68, Table 19, Line 17, delete "(H20" and insert --($H_2O$--.

In Column 68, Table 19, Line 18, delete "(H20)" and insert --($H_2O$)--.

In Column 68, Line 54, delete "olerace" and insert --oleracea--.

In Column 68, Line 55, delete "virgats" and insert --virgata--.

In Column 70, Line 8, delete "more or" and insert --more" or--.

In Column 70, Line 20, delete "intended," and insert --intended--.

In Column 71, Lines 19-20, delete "Eutrophication" and insert --Eutrophication.--.

In Column 71, Line 27, delete "155-162)" and insert --155-162).--.

In Column 71, Line 39, delete "Czamota," and insert --Czamota--.

In Column 71, Line 43, delete "Seabloom.," and insert --Seabloom,--.

In Column 71, Line 49, delete "Eaten. Servo" and insert --Exten. Serv.--.

In Column 71, Line 54, delete "516 pp" and insert --516 pp.--.

In Column 71, Line 57, delete "740-746" and insert --740-746.--.

In Column 71, Line 63, delete "Eaten." and insert --Exten.--.

In Column 72, Line 2, delete "16 pp" and insert --16 pp.--.

In Column 72, Line 5, delete "33-47" and insert --33-47.--.

In Column 72, Line 7, delete "63-131" and insert --63-131.--.

In Column 72, Line 8, delete "D," and insert --D.--.

CERTIFICATE OF CORRECTION (continued)
U.S. Pat. No. 10,595,534 B2

In Column 72, Line 10, delete "193-201" and insert --193-201.--.

In Column 72, Line 13, delete "www.hunker.com" and insert --www.hunker.com.--.

In Column 72, Line 16, delete "4 pp" and insert --4 pp.--.

In Column 72, Line 25, delete "143-157" and insert --143-157.--.

In Column 72, Line 28, delete "4 pp" and insert --4 pp.--.

In Column 72, Line 31, delete "pp.+appendices" and insert --pp.+appendices.--.

In Column 72, Line 38, delete "201-218" and insert --201-218.--.